US012266425B1

(12) United States Patent
Robins et al.

(10) Patent No.: US 12,266,425 B1
(45) Date of Patent: Apr. 1, 2025

(54) T CELL RECEPTOR SEQUENCES DIAGNOSTIC FOR COVID-19 AND RELATED COMPOSITIONS

(71) Applicant: Adaptive Biotechnologies Corporation, Seattle, WA (US)

(72) Inventors: Harlan S. Robins, Seattle, WA (US); Mark Klinger, Seattle, WA (US); Thomas M. Snyder, San Bruno, CA (US)

(73) Assignee: Adaptive Biotechnologies Corporation, Seattle, WA (US)

( * ) Notice: Subject to any disclaimer, the term of this patent is extended or adjusted under 35 U.S.C. 154(b) by 387 days.

(21) Appl. No.: 17/343,541

(22) Filed: Jun. 9, 2021

Related U.S. Application Data

(60) Provisional application No. 63/111,387, filed on Nov. 9, 2020, provisional application No. 63/055,877, filed on Jul. 23, 2020, provisional application No. 63/037,563, filed on Jun. 10, 2020.

(51) Int. Cl.
*G16B 30/00* (2019.01)
*A61K 39/00* (2006.01)

(52) U.S. Cl.
CPC .......... *G16B 30/00* (2019.02); *A61K 39/4611* (2023.05)

(58) Field of Classification Search
CPC ...................................................... G16B 30/00
See application file for complete search history.

(56) References Cited

U.S. PATENT DOCUMENTS

| | | | |
|---|---|---|---|
| 5,858,358 | A | 1/1999 | June et al. |
| 5,883,223 | A | 3/1999 | Gray |
| 6,352,694 | B1 | 3/2002 | June et al. |
| 6,534,055 | B1 | 3/2003 | June et al. |
| 6,692,964 | B1 | 2/2004 | June et al. |
| 6,797,514 | B2 | 9/2004 | Berenson et al. |
| 6,867,041 | B2 | 3/2005 | Berenson et al. |
| 6,887,466 | B2 | 5/2005 | June et al. |
| 6,905,680 | B2 | 6/2005 | June et al. |
| 6,905,681 | B1 | 6/2005 | June et al. |
| 6,905,874 | B2 | 6/2005 | Berenson et al. |
| 7,067,318 | B2 | 6/2006 | June et al. |
| 7,144,575 | B2 | 12/2006 | June et al. |
| 7,172,869 | B2 | 2/2007 | June et al. |
| 7,175,843 | B2 | 2/2007 | June et al. |
| 7,232,566 | B2 | 6/2007 | June et al. |
| 9,150,905 | B2 | 10/2015 | Robins et al. |
| 9,181,590 | B2 | 11/2015 | Robins et al. |
| 9,181,591 | B2 | 11/2015 | Robins et al. |
| 2010/0330571 | A1 | 12/2010 | Robins et al. |
| 2012/0058902 | A1 | 3/2012 | Livingston et al. |
| 2013/0253842 | A1 | 9/2013 | Sherwood et al. |
| 2013/0288237 | A1 | 10/2013 | Robins et al. |
| 2015/0203897 | A1 | 7/2015 | Robins et al. |
| 2015/0299785 | A1 | 10/2015 | Livingston et al. |

FOREIGN PATENT DOCUMENTS

| | | |
|---|---|---|
| WO | WO2010/151416 | 12/2010 |
| WO | WO2011/106738 | 9/2011 |
| WO | WO2012/027503 | 3/2012 |
| WO | WO2013/169957 | 11/2013 |
| WO | WO2013/188831 | 12/2013 |
| WO | WO2014/055561 | 4/2014 |
| WO | WO-2022150610 A2 * | 7/2022 |

OTHER PUBLICATIONS

Arstila et al. (1999) "A Direct Estimate of the Human α/β T Cell Receptor Diversity" Science 286(5441): 958-961.
Cabaniols et al. (2001) "Most α/βT Cell Receptor Diversity is Due to Terminal Deoxynucleotidyl Transferase" Journal of Experimental Medicine 194: 1385-1390.
Carlson et al. (2013) "Using synthetic templates to design an unbiased multiplex PCR assay" Nature Communications 4: 2680, p. 1-9.
Chu et al. (1981) "SV40 DNA transfection of cells in suspension: analysis of the efficiency of transcription and translation of T-antigen" Gene 13: 197-202.
Emerson et al. (2017) "Immunosequencing identifies signatures of cytomegalovirus exposure history and HLA-mediated effects on the T cell repertoire" Nature Genetics 49: 659-665.
Govers et al. (2010) "T cell receptor gene therapy: strategies for optimizing transgenic TCR pairing" Trends in Molecular Medicine 16(2): 77-87.
Griffoni et al. (2020) "Targets of T Cell Responses to SARS-CoV-2 Coronavirus in Humans with COVID-19 Disease and Unexposed Individual" Cell;181(7): 1489-1501.
Isho et al. (2020) "Persistence of serum and saliva antibody responses to SARS-CoV-2 spike antigens in patients with COVID-19" Science Immunology 5(52): eabe5511, p. 1-14.
Iyer et al. (2020) "Persistence and decay of human antibody responses to the receptor binding domain of SARS-COV-2 spike protein in COVID-19 patients" Science Immunology 5(52): eabe0367, p. 1-13.

(Continued)

*Primary Examiner* — Kaitlyn L Minchella
*Assistant Examiner* — Janna Nicole Schultzhaus
(74) *Attorney, Agent, or Firm* — Shweta Chandra; Bozicevic, Field & Francis LLP

(57) ABSTRACT

Provided are methods of assessing a biological sample obtained from an individual for the presence of a T cell that expresses a T cell receptor (TCR) comprising a TCRβ CDR3 sequence set forth in Table 1. Such methods further comprise identifying the individual as having COVID-19 when the presence of the TCR is detected. The presence of one or more of these TCRs may be of use in prognosticating severity of COVID-19 in the individual and the individual may be treated based on the expected severity of COVID-19. Treatment methods may include administering to the individual a T cell engineered to express the TCR. Such engineered T cells are also disclosed. Also provided are compositions and multimers that find use, e.g., in practicing the methods of the present disclosure.

12 Claims, 8 Drawing Sheets
Specification includes a Sequence Listing.

(56) References Cited

OTHER PUBLICATIONS

Klinger et al. (2013) "Combining Next-Generation Sequencing and Immune Assays: A Novel Method for Identification of Antigen-Specific T Cells" PLoS One 8(9): e74231, p. 1-9.

Klinger et al. (2015) "Multiplex Identification of Antigen-Specific T Cell Receptors Using a Combination of Immune Assays and Immune Receptor Sequencing" PLoS One 10(10): e0141561, p. 1-21.

Lavezzo et al. (2020) "Suppression of a SARS-CoV-2 outbreak in the Italian municipality of Vo'" Nature 584: 425-429.

Long et al. (2020) "Clinical and immunological assessment of asymptomatic SARS-CoV-2 infections" Nature Medicine 26: 1200-1204.

Mulder et al. (2020) "Reinfection of Severe Acute Respiratory Syndrome Coronavirus 2 in an Immunocompromised Patient: A Case Report" Clinical Infectious Diseases: ciaa1538, p. 1-2.

Nolan et al. (2020) "A large-scale database of T-cell receptor beta (TCRβ) sequences and binding associations from natural and synthetic exposure to SARS-CoV-2" Research Square (1): rs.3.rs-51964 Preprint, p. 1-28.

Robins et al. (2010) "Overlap and Effective Size of the Human CD8+ T Cell Receptor Repertoire" Science Translation Medicine 2(47): 47ra64, p. 1-11.

Robins et al. (2012) "Ultra-sensitive detection of rare T cell clones" Journal of Immunological Methods 375(1-2): 14-19.

Robins et al. (2009) "Comprehensive assessment of T-cell receptor β-chain diversity in αβ T cells" Blood 114(19): 4099-4107.

Sekine et al. (2020) "Robust T Cell Immunity in Convalescent Individuals with Asymptomatic or Mild COVID-19" Cell 183(1): 158-168.

Seow et al. (2020) "Longitudinal observation and decline of neutralizing antibody responses in the three months following SARS-CoV-2 infection in humans" Nature Microbiology 5: 1598-1607.

Sherwood et al. (2011) "Deep Sequencing of the Human TCRγ and TCRβ Repertoires Suggests that TCRβ Rearranges After αβ and γδ T Cell Commitment" Science Translational Medicine 3(90): 90ra61, p. 1-8.

Snyder et al. (2020) "Magnitude and Dynamics of the T-Cell Response to SARS-CoV-2 Infection at Both Individual and Population Levels" medRxiv (3): Preprint, p. 1-33.

Tillett et al. (2020) "Genomic evidence for reinfection with SARS-CoV-2: a case study" Lancet Infectious Diseases 21(1): 52-58.

Wang et al. (2016) "Phase 1 studies of central memory-derived CD19 Car T-cell therapy following autologous HSCT in patients with B-cell NHL" Blood 127(24):2980-2990.

Weiskopf et al. (2020) "Phenotype and kinetics of SARS-CoV-2-specific T cells in COVID-19 patients with acute respiratory distress syndrome" Science Immunology 5(48): eabd2071, p. 1-14.

World Health Organization (2020) "Coronavirus disease 2019 (COVID-19) Situation Report—94" 12 pages.

World Health Organization (2020) "Virtual press conference on COVID-19—Mar. 11, 2020" 17 pages.

Zhang et al. (2019) "The Emerging World of TCR-T Cell Trials Against Cancer: A Systematic Review" Technology in Cancer Research & Treatment (18):1533033819831068, p. 1-13.

Zhao et al. (2019) "Engineered T Cell Therapy for Cancer in the Clinic" Frontiers in Immunology (10):2250, p. 1-20.

Zuo et al. (2020) "Robust SARS-CoV-2-specific T-cell immunity is maintained at 6 months following primary infection" bioRxiv preprint, 25 pages.

* cited by examiner

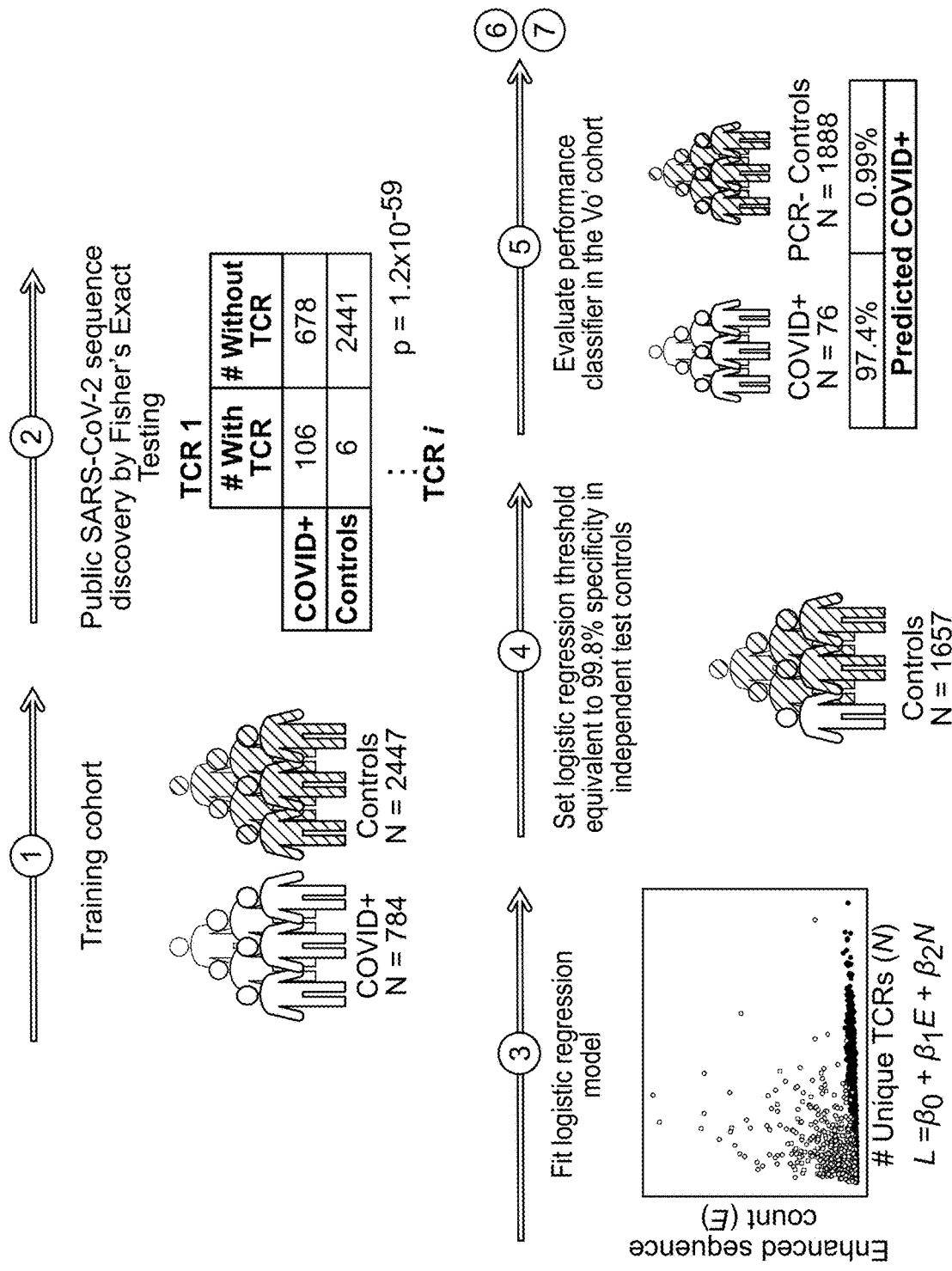

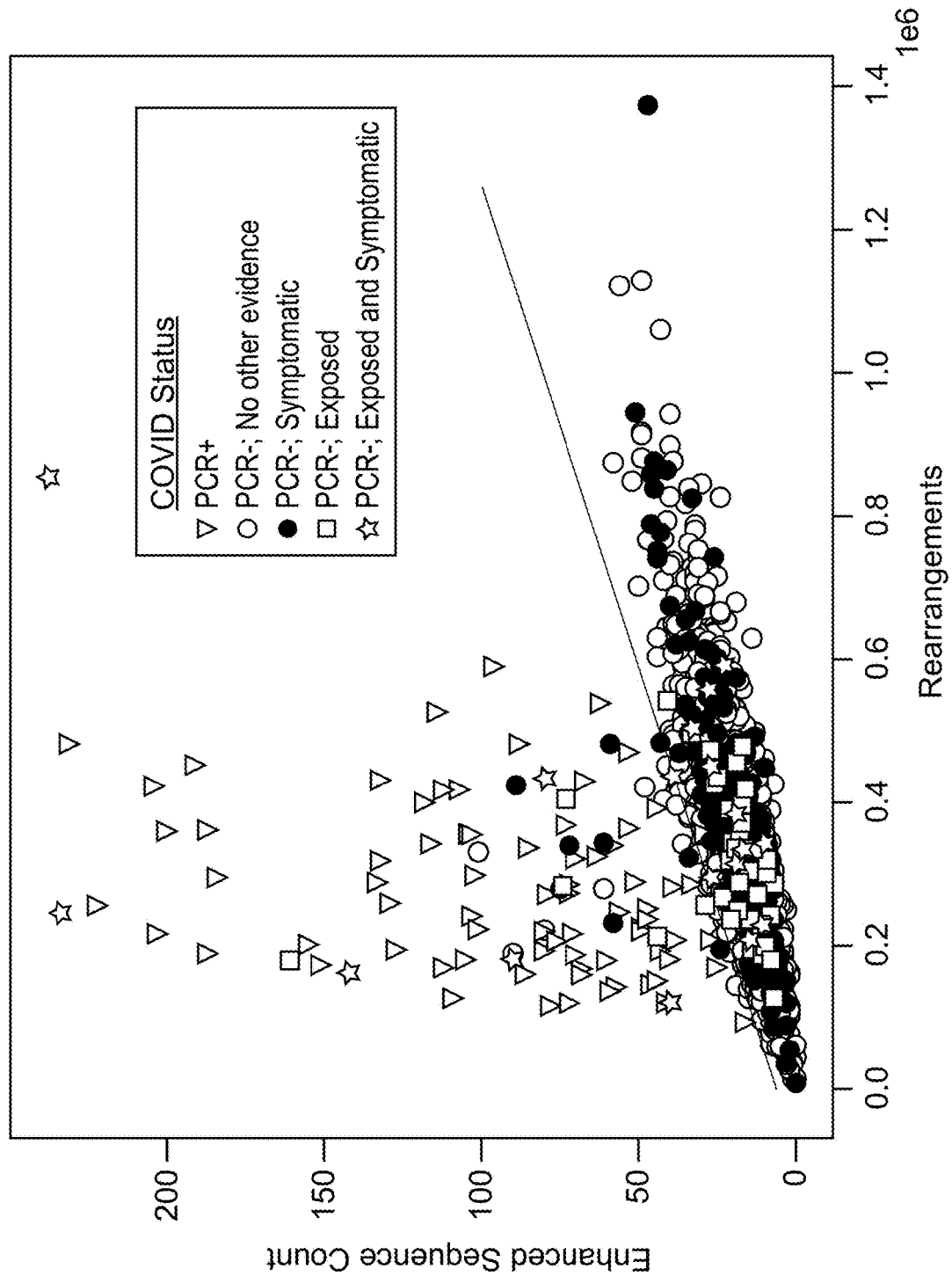

T CELL RECEPTOR SEQUENCES DIAGNOSTIC FOR COVID-19 AND RELATED COMPOSITIONS

CROSS-REFERENCE TO RELATED APPLICATIONS

This application claims the benefit of U.S. Provisional Patent Application No. 63/037,563, filed Jun. 10, 2020, U.S. Provisional Patent Application No. 63/055,877, filed Jul. 23, 2020, and U.S. Provisional Patent Application No. 63/111,387, filed Nov. 9, 2020, which applications are incorporated herein by reference in their entirety.

INCORPORATION BY REFERENCE OF SEQUENCE LISTING PROVIDED AS TEXT FILE

A Sequence Listing is provided herewith as a text file, "ADBS-087 SEQ LIST_ST25.txt," created on Jun. 8, 2021 and having a size of 48,988 bytes. The contents of the text file are incorporated by reference herein in their entirety.

INTRODUCTION

Severe acute respiratory syndrome coronavirus 2 (SARS-CoV-2) has spread globally. Epidemiological data so far suggest that COVID-19 has case fatality rate of about 2.3%, several times greater than that of seasonal influenza. The elderly and individuals with underlying medical comorbidities such as cardiovascular disease, diabetes mellitus, chronic lung disease, chronic kidney disease, obesity, hypertension or cancer have a much higher mortality rate than healthy young adults.

Diagnostic, prognostic, and therapeutic tools are needed to control spread of the virus as well as to increase treatment efficacy.

Antigen-specific cellular immune responses are mediated by a diverse population of T cells and B cells, each bearing immune cell receptors (TCRs and BCRs, respectively) capable of recognizing a specific antigen (in the case of T cells, an antigen peptide bound to a particular major histocompatibility complex (MHC) molecule on the surface of host cells). Encounter with an antigen leads to the clonal expansion, activation, and maturation of T and B cells, resulting in effector populations of cytotoxic ($CD8^+$ CTL) and helper ($CD4^+$) T cells, or antibodies and memory B cells, respectively. The presence of antigen-specific effector cells is diagnostic of an immune response specific to that antigen.

Activated T cells proliferate by clonal expansion and reside in the memory T cell compartment for many years as a clonal population of cells (clones) with identical-by-descent rearranged TCR genes (Arstila T P, et al. A direct estimate of the human alpha/beta T cell receptor diversity, *Science* 286:958-961, 1999).

The majority of TCR diversity resides in the beta chain of the TCR alpha/beta heterodimer. Immense diversity is generated by combining noncontiguous TCRβ variable (V), diversity (D), and joining (J) region gene segments, which collectively encode the CDR3 region, the primary region of the TCRβ locus for determining antigen specificity. Deletion and template-independent insertion of nucleotides during rearrangement at the Vβ-Dβ and Dβ-Jβ junctions further add to the potential diversity of receptors that can be encoded (Cabaniols J P, et al. Most alpha/beta T cell receptor diversity is due to terminal deoxynucleotidyl transferase, *J Exp Med* 194:1385-1390, 2001). Typically, at a given point in time, an adult with a healthy immune system expresses approximately 10 million unique TCRβ chains on their 1012 circulating T cells (Robins H S, et al. (2009) Comprehensive assessment of T-cell receptor beta-chain diversity in alpha/beta T cells, *Blood* 114:4099-4107).

The human T-cell repertoire thus dynamically encodes exposure to disease-related antigens through rearrangements of their receptor-encoding genes and so provides an excellent basis for making diagnostic predictions. It has been demonstrated that TCRβ receptors in peripheral blood samples from human subjects can be employed to predict the status of exposure to a disease; i.e., based on the presence and abundance of such receptors in the training cohort (Emerson et al., Immunosequencing identifies signatures of cytomegalovirus exposure history and HLA-mediated effects on the T cell repertoire, *Nature Genetics* April 2017; doi: 10.1038/ng.3822).

SUMMARY

Provided are methods of assessing T cell receptor β chain complementary determining region 3 (TCRβ CDR3) sequences. In certain embodiments, the methods comprise assessing TCRβ CDR3 sequences determined from a sample obtained from a subject having, suspected of having, or having had COVID-19 within 6 months of the assessing for the presence or absence of one or more TCRβ CDR3 sequences set forth in the present disclosure.

In certain embodiments, the methods further comprise diagnosing the subject as having COVID-19 when the presence of the TCR is detected and treating the subject. The presence of one or more of these TCRs may be of use in prognosticating severity of COVID-19 in the subject and the subject may be treated based on the expected severity of COVID-19.

Treatment methods may include administering to the subject a T cell engineered to express the TCR. Such engineered T cells are also provided.

Also provided are compositions and multimers that find use, e.g., in practicing the methods of the present disclosure.

BRIEF DESCRIPTION OF THE FIGURES

FIGS. 1A-1C. Identification and Use of Public T-Cell Receptors to Characterize the SARS-CoV-2 Immune Response. FIG. 1A. Schema of general approach, starting from a case-control design and Fisher's exact testing for each TCR on independent training data, to identify public T-cell receptor sequences that are overrepresented in cases versus controls. Following logistic regression to establish the T-cell test threshold for determining recent or past infection, the receptors are applied to this Vo' study data set. FIG. 1B. Incidence of each T-cell receptor sequence compared in the training data and in the Vo' PCR-positive subjects. FIG. 1C. The count of enhanced sequences is plotted vs. the total number of unique T-cell receptor rearrangements for subjects in the Vo' study data set that were positive by RT-PCR (open circles), or negative by RT-PCR (black circles) without any additional evidence for SARS-CoV-2 infection.

FIGS. 3A-3B. T-cell signature in RT-PCR-subjects with other evidence of SARS-CoV-2 infection. FIG. 3A. Count of enhanced sequences in RT-PCR-cases that were symptomatic, had a household exposure, or were both symptomatic and had a household exposure are highlighted. RT-PCR+, and RT-PCR-cases without additional evidence of SARS-CoV-2 infection are also shown. FIG. 3B. Rate of T-cell test calls in individuals with a negative RT-PCR test at the time of initial survey; positive T-cell test results were observed more often in exposed and/or symptomatic individuals.

DETAILED DESCRIPTION

Figure 1B:
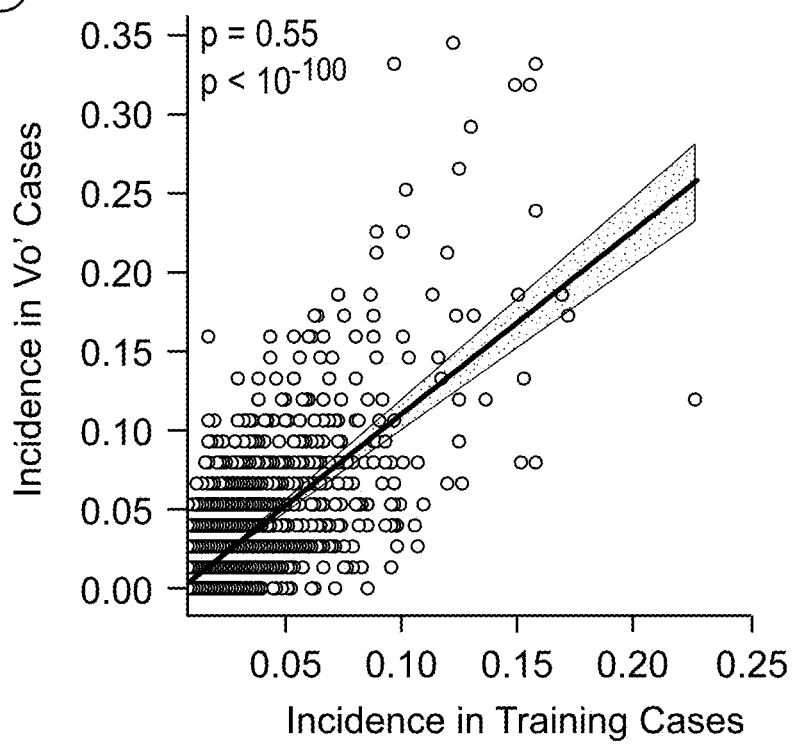
Figure 1C:
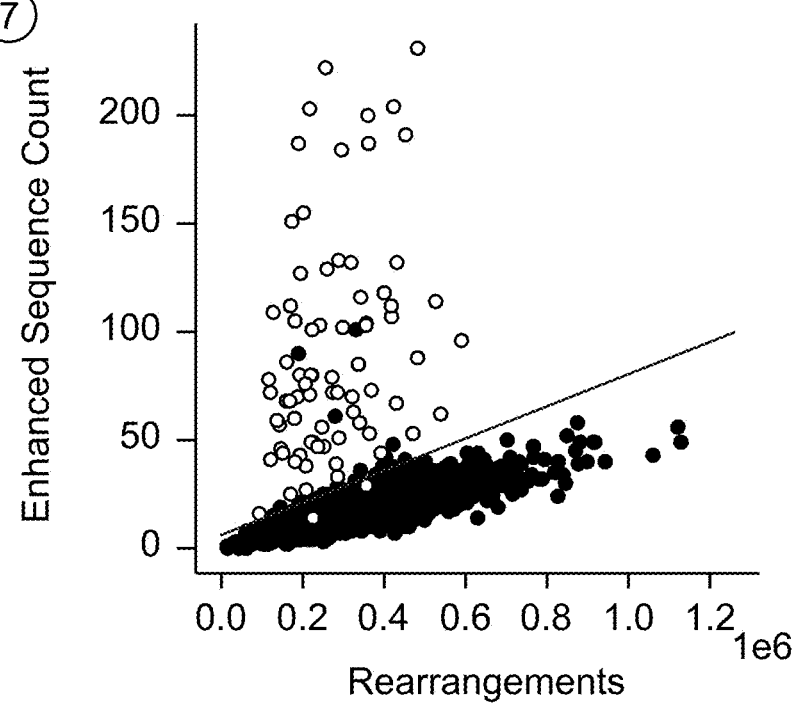

Before the methods, compositions and multimers of the present disclosure are described in greater detail, it is to be understood that the methods, compositions and multimers are not limited to particular embodiments described, as such may, of course, vary. It is also to be understood that the terminology used herein is for the purpose of describing particular embodiments only, and is not intended to be limiting, since the scope of the methods, compositions and multimers will be limited only by the appended claims.

Where a range of values is provided, it is understood that each intervening value, to the tenth of the unit of the lower limit unless the context clearly dictates otherwise, between the upper and lower limit of that range and any other stated or intervening value in that stated range, is encompassed within the methods, compositions and multimers. The upper and lower limits of these smaller ranges may independently be included in the smaller ranges and are also encompassed within the methods, compositions and multimers, subject to any specifically excluded limit in the stated range. Where the stated range includes one or both of the limits, ranges excluding either or both of those included limits are also included in the methods, compositions and multimers.

Certain ranges are presented herein with numerical values being preceded by the term "about." The term "about" is used herein to provide literal support for the exact number that it precedes, as well as a number that is near to or approximately the number that the term precedes. In determining whether a number is near to or approximately a specifically recited number, the near or approximating unrecited number may be a number which, in the context in which it is presented, provides the substantial equivalent of the specifically recited number.

Unless defined otherwise, all technical and scientific terms used herein have the same meaning as commonly understood by one of ordinary skill in the art to which the methods, compositions and multimers belong. Although any methods, compositions and multimers similar or equivalent to those described herein can also be used in the practice or testing of the methods, compositions and multimers, representative illustrative methods, compositions and multimers are now described.

All publications and patents cited in this specification are herein incorporated by reference as if each individual publication or patent were specifically and individually indicated to be incorporated by reference and are incorporated herein by reference to disclose and describe the materials and/or methods in connection with which the publications are cited. The citation of any publication is for its disclosure prior to the filing date and should not be construed as an admission that the present methods, compositions and multimers are not entitled to antedate such publication, as the date of publication provided may be different from the actual publication date which may need to be independently confirmed.

It is noted that, as used herein and in the appended claims, the singular forms "a", "an", and "the" include plural referents unless the context clearly dictates otherwise. It is further noted that the claims may be drafted to exclude any optional element. As such, this statement is intended to serve as antecedent basis for use of such exclusive terminology as "solely," "only" and the like in connection with the recitation of claim elements, or use of a "negative" limitation.

It is appreciated that certain features of the methods, compositions and multimers, which are, for clarity, described in the context of separate embodiments, may also be provided in combination in a single embodiment. Conversely, various features of the methods, compositions and multimers, which are, for brevity, described in the context of a single embodiment, may also be provided separately or in any suitable sub-combination. All combinations of the embodiments are specifically embraced by the present disclosure and are disclosed herein just as if each and every combination was individually and explicitly disclosed, to the extent that such combinations embrace operable processes and/or compositions. In addition, all sub-combinations listed in the embodiments describing such variables are also specifically embraced by the present methods, compositions and multimers and are disclosed herein just as if each and every such sub-combination was individually and explicitly disclosed herein.

As will be apparent to those of skill in the art upon reading this disclosure, each of the individual embodiments described and illustrated herein has discrete components and features which may be readily separated from or combined with the features of any of the other several embodiments without departing from the scope or spirit of the present methods. Any recited method can be carried out in the order of events recited or in any other order that is logically possible.

Methods for Assessing TCRβ CDR3 Sequences

The present disclosure provides methods for assessing T cell receptor β chain complementary determining region 3 (TCRβ CDR3) sequences. In certain embodiments, the methods comprise assessing TCRβ CDR3 sequences determined from a sample obtained from a subject having, suspected of having COVID-19, or having had COVID-19 within 6 months of the assessing, for the presence or absence of one or more TCRβ CDR3 sequences set forth in SEQ ID NOs: 1-199. The inventors have determined that TCRs comprising such TCRβ CDR3 sequences are associated with COVID-19 infection where the infection may be ongoing or may have occurred within 6 months (e.g., 1-6 months, 1-5 months, 1-4 months, 1-3 months, or 1-2 months) of the assessing. These TCRβ CDR3 sequences were identified from machine learning models developed on 784 COVID-19 cases versus 2447 controls. Accordingly, the methods of the present disclosure find use, for example, in predicting the presence or absence of present or previous COVID-19 in the subject. Details regarding the methods of the present disclosure will now be described.

According to some embodiments, the methods of the present disclosure are computer-implemented. By "computer-implemented" is meant at least one step of the method is implemented using one or more processors and one or more non-transitory computer-readable media. For example, in certain embodiments, provided are computer-implemented methods for assessing TCRβ CDR3 sequences, the methods being implemented using one or more processors and one or more non-transitory computer-readable media comprising instructions stored thereon, which when executed by the one or more processors, cause the one or more processors to assess TCRβ CDR3 sequences determined from a sample obtained from a subject having or suspected of having COVID-19, or having had COVID-19 within 6 months of the assessing, for the presence or absence of one or more TCRβ CDR3 sequences set forth in SEQ ID Nos: 1-199 herein. The computer-implemented methods of the present disclosure may further comprise one or more steps that are not computer-implemented, e.g., obtaining a sample (e.g., a blood sample) from the subject, preparing the sample for immune repertoire nucleic acid sequencing, and/or the like.

As noted above, the subject is one having or suspected of having COVID-19, or having had COVID-19 within 6 months of the assessing. A subject having COVID-19 may have been diagnosed as having COVID-19 based on one or more of: presence of symptoms associated with COVID-19, presence of anti-SARS-CoV-2 antibodies, and a SARS-CoV-2 positive PCR. A subject suspected of having COVID-19 may have symptoms associated with COVID-19 but may or may not have anti-SARS-CoV-2 antibodies and a SARS-CoV-2 positive PCR. A subject having had COVID-19 within 6 months of the assessing may not have symptoms associated with COVID-19, may not have anti-SARS-CoV-2 antibodies and may not have SARS-CoV-2 positive PCR but may have been diagnosed as having COVID-19 or may have had symptoms associated with COVID-19 within 6 months of the assessing.

As summarized above, the methods of the present disclosure comprise assessing the TCRβ CDR3 sequences determined from the sample obtained from the subject for the presence or absence of one or more TCRβ CDR3 sequences set forth in SEQ ID Nos: 1-199 set forth herein. As noted above, in certain embodiments, the assessing step may be computer-implemented such that it is performed using one or more processors and one or more non-transitory computer-readable media comprising instructions stored thereon, which when executed by the one or more processors, cause the one or more processors to assess the determined TCRβ CDR3 sequences for the presence or absence of one or more TCRβ CDR3 sequences set forth in SEQ ID Nos: 1-199. For example, the instructions may cause the one or more processors to compare each of the determined TCRβ CDR3 sequences (e.g., each determined TCRβ CDR3 sequence or each unique determined TCRβ CDR3 sequence) stored on a computer-readable medium to a database comprising one or more TCRβ CDR3 sequences set forth in SEQ ID Nos: 1-199 stored on the same or a different computer-readable medium. According to some embodiments, the number of TCRβ CDR3 sequences determined from the sample obtained from the subject is from 1,000 to 2,000,000. For example, in certain embodiments, the number of determined TCRβ CDR3 sequences is 2,000,000 or fewer (e.g., 1,500,000 or fewer, 1,250,000 or fewer, 1,000,000 or fewer, 750,000 or fewer, or 500,000 or fewer), but 1,000 or more, 5,000 or more, 10,000 or more, 15,000 or more, 20,000 or more, 25,000 or more, 30,000 or more, 35,000 or more, 40,000 or more, 45,000 or more, 50,000 or more, 55,000 or more, 60,000 or more, 65,000 or more, 70,000 or more, 75,000 or more, 80,000 or more, 85,000 or more, 90,000 or more, 95,000 or more, or 100,000 or more. The number of TCRβ CDR3 sequences set forth in SEQ ID Nos: 1-199 to which the determined TCRβ CDR3 sequences is compared may vary. For example, the determined TCRβ CDR3 sequences may be compared to 1 or more, 2 or more, 3 or more, 4 or more, 5 or more, 6 or more, 7 or more, 8 or more, 9 or more, 10 or more, 15 or more, 20 or more, 25 or more, 30 or more, 35 or more, 40 or more, 45 or more, 50 or more, 75 or more, 100 or more, 150 or more, or all of each of the TCRβ CDR3 sequences set forth in SEQ ID Nos: 1-199. When the determined TCRβ CDR3 sequences are compared to fewer than all of the TCRβ CDR3 sequences set forth in SEQ ID Nos: 1-199, the determined TCRβ CDR3 sequences may be compared to any desired number (e.g., as set forth above) and any desired combination of TCRβ CDR3 sequences set forth in SEQ ID Nos: 1-199.

The methods of the present disclosure may include one or more additional steps based on the results of the assessing step. For example, if it is determined from the assessing step that none of the TCRβ CDR3 sequences set forth in SEQ ID Nos: 1-199 are present in the TCRβ CDR3 sequences determined from the sample obtained from the subject having or suspected of having COVID-19 or having had COVID-19 in the past 6 months, then the methods may further comprise, e.g., identifying the subject as not having COVID-19 or not having had COVID-19 or identifying the subject as one who should not be administered a COVID-19 therapy. Also by way of example, if it is determined from the assessing step that one or more (e.g., 2 or more, 3 or more, 4 or more, 5 or more, or 10 or more) of the TCRβ CDR3 sequences set forth in SEQ ID Nos: 1-199 are present in the TCRβ CDR3 sequences determined from the sample obtained from the subject having or suspected of having COVID-19 or having had COVID-19, then the methods may further comprise, e.g., identifying the subject as presently having or previous having COVID-19, identifying the subject as having COVID-19 and identifying the subject as one who should be administered a COVID-19 therapy, and/or administering a COVID-19 therapy to the subject.

In certain embodiments, the methods further comprise subjecting the results of the assessing step to further analysis, such as subjecting the results of the assessing step to a model. For example, the methods may further comprise subjecting the results of the assessing step to a model in order to classify the subject as having a present or previous SARS-CoV-2 infection or not having a present or previous SARS-CoV-2 infection; and/or to classify the subject as having COVID-19 or not having COVID-19. One of ordinary skill in the art will appreciate that, with the benefit of the TCRβ CDR3 sequences set forth in SEQ ID Nos: 1-199 described herein, a variety of useful models may be applied to the results of the assessment. In one non-limiting example, the methods may further comprise subjecting the results of the assessing step to a two feature logistic regression with features representing the number of COVID-19-associated TCRβ CDR3 sequences determined from the sample and the total number of unique TCRβ CDR3 sequences determined from the sample. As demonstrated in the Experimental section below, such a model exhibits high specificity for COVID-19 patients and greater sensitivity at diagnosing COVID-19 as compared to presence of anti-SARS-CoV-2 antibodies.

In certain embodiments, when the methods further comprise subjecting the results of the assessing step to a model for classification purposes (e.g., as described above), the model may take into account the number of unique COVID-19-associated TCRβ CDR3 sequences that are present in the TCRβ CDR3 sequences determined from the sample, e.g., where the greater the number of unique COVID-19-associated TCRβ CDR3 sequences, the more likely the model is to classify the subject as having a present or previous SARS-CoV-2 infection and/or having COVID-19. According to some embodiments, the number of unique COVID-19-associated TCRβ CDR3 sequences is not a feature utilized by the model to classify the subject. In certain embodiments, the presence and/or frequency of one or more particular unique COVID-19-associated TCRβ CDR3 sequences is a feature(s) used by the model to classify the subject. For example, the presence and/or frequency of one or more particular unique COVID-19-associated TCRβ CDR3 sequences may be given relatively greater weight when classifying the subject as compared to the presence and/or frequency of one or more other unique COVID-19-associated TCRβ CDR3 sequences.

According to some embodiments, when a classification model weighs particular unique COVID-19-associated TCRβ CDR3 sequences differently than other unique COVID-19-associated TCRβ CDR3 sequences, the model may use convergent recombination to weigh the sequences differently. Different T cells can show convergent recombination where unique DNA sequences were formed in the recombination for a first T cell, a second T cell, a third T cell, etc., but where each leads to the same protein (CDR3+V-gene+J-gene) which is diagnostic for high likelihood of COVID-19. This convergent recombination may be more likely for certain COVID-19-associated TCRβ CDR3 sequences than others, and the model may take into account these aspects of the signal reflective of the interpretable biology of immune response. Accordingly, in some embodiments, sequences may be given differential weight based on convergent recombination.

In certain embodiments, prior to the assessing step, the methods may further include one or more steps for determining the TCRβ CDR3 sequences from the sample obtained from the subject having or suspected of having COVID-19 or having had COVID-19 within the past 6 months. For example, the determining may include immunosequencing and evaluation of the T cell repertoire in the biological sample obtained from the subject, e.g., by high-throughput sequencing (HTS) as described elsewhere herein. The determining may be partially implemented using a computer. For example, the analysis of the raw sequencing data may be implemented by a computer. Extraction of DNA or RNA from the biological sample, amplification, and sequencing may be performed manually, using a machine, or a combination thereof. In certain embodiments, the methods may further comprise an initial step of obtaining the biological sample from the subject.

The biological sample (e.g., tissue or blood) may be obtained from a variety of subjects. Such subjects may be "mammals" or "mammalian," where these terms are used broadly to describe organisms which are within the class mammalia, including the orders carnivore (e.g., dogs and cats), rodentia (e.g., mice, guinea pigs, and rats), and primates (e.g., humans, non-human primates such as chimpanzees, and monkeys). In some embodiments, the subject is a human subject.

Biological samples of interest include those that comprise T cells, including but not limited to, whole blood samples, a fraction of whole blood comprising peripheral blood mononuclear cells (e.g., blood plasma), serum, a peripheral blood mononuclear cell (PBMC) sample, urine, buffy coat, synovial fluid, bone marrow, cerebrospinal fluid, saliva, lymph fluid, seminal fluid, vaginal secretions, urethral secretions, exudate, transdermal exudates, pharyngeal exudates, nasal secretions, sputum, sweat, bronchoalveolar lavage, tracheal aspirations, fluid from joints, or vitreous fluid. T cells can also be obtained from biological samples which may be derived from, for example, solid tissue samples. T-cells may be helper T cells (effector T cells or Th cells), cytotoxic T cells (CTLs), memory T cells, and regulatory T cells. In some embodiments, peripheral blood mononuclear cells (PBMC) are isolated by techniques known to those of skill in the art, e.g., by Ficoll-Hypaque® density gradient separation.

Nucleic acid, such as, genomic DNA or RNA may be extracted from lymphoid cells by methods known to those of skill in the art. Examples include using the QIAamp® DNA blood Mini Kit or a Qiagen DNeasy® Blood extraction kit (both commercially available from Qiagen, Gaithersburg, Md., USA) to extract genomic DNA. In some embodiments, 100,000 to 200,000 cells may be used for analysis of diversity, i.e., about 0.6 to 1.2 µg DNA from diploid T cells. Using PBMCs as a source, the number of T cells can be estimated to be about 30% of total cells. Alternatively, total nucleic acid can be isolated from cells, including both genomic DNA and mRNA. In other embodiments, cDNA is transcribed from mRNA and then used as templates for amplification. The RNA molecules can be transcribed to cDNA using known reverse-transcription kits, such as the SMARTer™ Ultra Low RNA kit for Illumina sequencing (Clontech, Mountain View, Calif.) essentially according to the supplier's instructions.

Immune Repertoire Sequencing (Multiplex PCR and High Throughput Sequencing)

According to some embodiments, TCRβ CDR3 sequences are determined from the sample obtained from the subject by immune cell receptor sequencing, e.g., immune repertoire sequencing.

By "T cell receptor" or "TCR" is meant a disulfide-linked membrane bound heterodimeric protein normally consisting of the highly variable α and β chains expressed as part of a complex with the invariant CD3 chain molecules. T cells expressing these two chains are referred to as α:β (or αβ) T cells, though a minority of T cells express an alternate receptor, formed by variable γ and δ chains, referred as γσ T cells. TCR development occurs through a lymphocyte specific process of gene recombination, which assembles a final sequence from a large number of potential segments. This genetic recombination of TCR gene segments in somatic T cells occurs during the early stages of development in the thymus. The TCRα gene locus contains variable (V) and joining (J) gene segments (Vα and Jα), whereas the TCRβ locus contains a D gene segment in addition to Vβ and Jβ segments. Accordingly, the α chain is generated from VJ recombination and the β chain is involved in VDJ recombination. This is similar for the development of γδ TCRs, in which the TCRγ chain is involved in VJ recombination and the TCRδ gene is generated from VDJ recombination. The TCR α chain gene locus consists of 46 variable segments, 8 joining segments and the constant region. The TCR β chain gene locus consists of 48 variable segments followed by two diversity segments, 12 joining segments and two constant regions. The D and J segments are located within a relatively short 50 kb region while the variable genes are spread over a large region of 1.5 mega bases (TCRα) or 0.67 mega bases (TCRβ).

TCRβ CDR3 sequence determination may involve quantitative detection of sequences of substantially all possible TCR gene rearrangements that can be present in a sample containing lymphoid cell DNA.

Amplified nucleic acid molecules comprising rearranged TCR regions obtained from a biological sample are sequenced using high-throughput sequencing. In one embodiment, a multiplex PCR system is used to amplify rearranged TCR loci from genomic DNA as described in U.S. Pub. No. 2010/0330571, filed on Jun. 4, 2010, U.S. Pub. No. 2012/0058902, filed on Aug. 24, 2011, International App. No. PCT/US2013/062925, filed on Oct. 1, 2013, which is each incorporated by reference in its entirety.

To that end, multiplex PCR is performed using a set of forward primers that specifically hybridize to V segments and a set of reverse primers that specifically hybridize to the J segments of a TCR locus, where a multiplex PCR reaction using the primers allows amplification of all the possible VJ (and VDJ) combinations within a given population of T cells.

Exemplary V segment primers and J segment primers are described in US2012/0058902, US2010/033057, WO2010/151416, WO2011/106738, US2015/0299785, WO2012/027503, US2013/0288237, U.S. Pat. Nos. 9,181,590, 9,181,591, US2013/0253842, WO2013/188831, which are each herein incorporated by reference in their entireties.

A multiplex PCR system can be used to amplify rearranged immune cell receptor loci. In certain embodiments, the CDR3 region is amplified from a TCRβ CDR3 region locus. A plurality of V-segment and J-segment primers are used to amplify substantially all (e.g., greater than 90%, 91%, 92%, 93%, 94%, 95%, 96%, 97%, 98% or 99%) rearranged immune cell receptor CDR3-encoding regions to produce a multiplicity of amplified rearranged DNA molecules. In certain embodiments, primers are designed so that each amplified rearranged DNA molecule is less than 600 nucleotides in length, thereby excluding amplification products from non-rearranged immune cell receptor loci.

In some embodiments, two pools of primers are used in a single, highly multiplexed PCR reaction. The "forward" pool of primers can include a plurality of V segment oligonucleotide primers and the reverse pool can include a plurality of J segment oligonucleotide primers. In some embodiments, there is a primer that is specific to (e.g., having a nucleotide sequence complementary to a unique sequence region of) each V region segment and to each J region segment in the respective TCR or Ig gene locus. In other embodiments, a primer can hybridize to one or more V segments or J segments, thereby reducing the number of primers required in the multiplex PCR. In certain embodiments, the J-segment primers anneal to a conserved sequence in the joining ("J") segment.

Each primer can be designed such that a respective amplified DNA segment is obtained that includes a sequence portion of sufficient length to identify each J segment unambiguously based on sequence differences amongst known J-region encoding gene segments in the human genome database, and also to include a sequence portion to which a J-segment-specific primer can anneal for resequencing. This design of V- and J-segment-specific primers enables direct observation of a large fraction of the somatic rearrangements present in the immune cell receptor gene repertoire within the subject.

A multiplex PCR system can use at least 2, 3, 4, 5, 6, 7, 8, 9, 10, 11, 12, 13, 14, 15, 16, 17, 18, 19, 20, 21, 22, 23, 24, or 25, and in certain embodiments, at least 26, 27, 28, 29, 30, 31, 32, 33, 34, 35, 36, 37, 38, or 39, and in other embodiments at least 40, 41, 42, 43, 44, 45, 46, 47, 48, 49, 50, 51, 52, 53, 54, 55, 56, 57, 58, 59, 60, 65, 70, 75, 80, 85, or more forward primers, in which each forward primer specifically hybridizes to (i.e., is complementary to) a sequence corresponding to a V region segment. The multiplex PCR system also uses at least 2, 3, 4, 5, 6, or 7, and in certain embodiments, at least 8, 9, 10, 11, 12 or 13 reverse primers, or at least 14, 15, 16, 17, 18, 19, 20, 21, 22, 23, 24, or 25 or more reverse primers, in which each reverse primer specifically hybridizes to or is complementary to a sequence corresponding to a J region segment. Various combinations of V and J segment primers can be used to amplify the full diversity of TCR sequences in the immune cell receptor gene repertoire within the subject.

Further details on multiplex PCR system, including primer oligonucleotide sequences for amplifying TCR sequences are described in Robins et al., 2009 *Blood* 114, 4099; Robins et al., 2010 *Sci. Translat. Med.* 2: 47ra64; Robins et al., 2011 *J. Immunol. Meth.* doi: 10.1016/j.jim.2011.09. 001; Sherwood et al. 2011 Sci. Translat. Med. 3:90ra61; US2012/0058902, US2010/033057, WO/2010/151416, WO/2011/106738, US 2015/0299785, WO2012/027503, US2013/0288237, U.S. Pat. Nos. 9,181,590, 9,181,591, US2013/0253842, WO2013/188831, which is each incorporated herein by reference in its entirety.

Oligonucleotides or polynucleotides that are capable of specifically hybridizing or annealing to a target nucleic acid sequence by nucleotide base complementarity can do so under moderate to high stringency conditions. In one embodiment, suitable moderate to high stringency conditions for specific PCR amplification of a target nucleic acid sequence can be between 25 and 80 PCR cycles, with each cycle including a denaturation step (e.g., about 10-30 seconds(s) at greater than about 95° C.), an annealing step (e.g., about 10-30 s at about 60-68° C.), and an extension step (e.g., about 10-60 s at about 60-72° C.), optionally according to certain embodiments with the annealing and extension steps being combined to provide a two-step PCR. As would be recognized by the skilled person, other PCR reagents can be added or changed in the PCR reaction to increase specificity of primer annealing and amplification, such as altering the magnesium concentration, optionally adding DMSO, and/or the use of blocked primers, modified nucleotides, peptide-nucleic acids, and the like.

A primer may be a single-stranded DNA. The appropriate length of a primer depends on the intended use of the primer but typically ranges from 6 to 50 nucleotides, or in certain embodiments, from 15-35 nucleotides in length. Short primer molecules generally require cooler temperatures to form sufficiently stable hybrid complexes with the template. A primer need not reflect the exact sequence of the template nucleic acid, but must be sufficiently complementary to hybridize with the template. The design of suitable primers for the amplification of a given target sequence is well known in the art and described in the literature cited herein.

V- and J-segment primers are used to produce a plurality of amplicons from the multiplex PCR reaction. In certain embodiments, the amplicons range in size from 10, 20, 30, 40, 50, 75, 100, 200, 300, 400, 500, 600, 700, 800 or more nucleotides in length. In certain embodiments, the amplicons have a size between 20-600, 50-600, 20-400, or 50-400 nucleotides in length.

According to non-limiting theory, these embodiments exploit current understanding in the art (also described above) that once a T lymphocyte has rearranged its TCR-encoding genes, its progeny cells possess the same immune cell receptor-encoding gene rearrangement, thus giving rise to a clonal population (clones) that can be uniquely identified by the presence therein of rearranged (e.g., CDR3-encoding) V- and J-gene segments that can be amplified by a specific pairwise combination of V- and J-specific oligonucleotide primers as herein disclosed.

The V segment primers and J segment primers will preferably each include a second sequence at the 5'-end of the primer that is not complementary to the target V or J segment. The second sequence can comprise an oligonucleotide having a sequence that is selected from (i) a universal adaptor oligonucleotide sequence, and (ii) a sequencing platform-specific oligonucleotide sequence that is linked to and positioned 5' to a first universal adaptor oligonucleotide sequence. Examples of universal adaptor oligonucleotide sequences can be pGEX forward and pGEX reverse adaptor sequences.

The resulting amplicons using the V-segment and J-segment primers described above include amplified V and J segments and the universal adaptor oligonucleotide sequences. The universal adaptor sequence can be complementary to an oligonucleotide sequence found in a tailing primer. Tailing primers can be used in a second PCR reaction to generate a second set of amplicons. In some embodiments, tailing primers can have the general formula (I):

   (I)

where P comprises a sequencing platform-specific oligonucleotide, where S comprises a sequencing platform tag-containing oligonucleotide sequence; where B comprises an oligonucleotide barcode sequence and where the oligonucleotide barcode sequence can be used to identify a sample source, and where U comprises a sequence that is complementary to the universal adaptor oligonucleotide sequence or is the same as the universal adaptor oligonucleotide sequence.

Additional description about universal adaptor oligonucleotide sequences, barcodes, and tailing primers are found in WO2013/188831, which is incorporated by reference in its entirety.

Sequencing may be performed using any of a variety of available high throughput single molecule sequencing machines and systems. Illustrative sequence systems include sequence-by-synthesis systems, such as the Illumina Genome Analyzer and associated instruments (Illumina HiSeq) (Illumina, Inc., San Diego, Calif.), Helicos Genetic Analysis System (Helicos BioSciences Corp., Cambridge, Mass.), Pacific Biosciences PacBio RS (Pacific Biosciences, Menlo Park, Calif.), a MinION™, GridIONx5™, PromethION™, or SmidgION™ nanopore-based sequencing system, available from Oxford Nanopore Technologies, or other systems having similar capabilities.

In certain embodiments, sequencing is achieved using a set of sequencing platform-specific oligonucleotides that hybridize to a defined region within the amplified DNA molecules. The sequencing platform-specific oligonucleotides are designed to sequence amplicons, such that the V- and J-encoding gene segments can be uniquely identified by the sequences that are generated. See, e.g., US2012/0058902; US2010/033057; WO2011/106738; US2015/0299785; or WO2012/027503, which is each incorporated by reference in its entirety.

In some embodiments, the raw sequence data is preprocessed to remove errors in the primary sequence of each read and to compress the data. A nearest neighbor algorithm can be used to collapse the data into unique sequences by merging closely related sequences, to remove both PCR and sequencing errors. See, e.g., US2012/0058902; US2010/033057; WO2011/106738; US2015/0299785; or WO2012/027503, which is each incorporated by reference in its entirety.

Sequencing the multiplicity of amplified rearranged TCRβ CDR3-encoding region DNA molecules by high-throughput sequencing (HTS) can be used to produce a TCR clonotype profile comprising at least 10,000 TCR clonotype sequences of 20 to 400 nucleotides in length.

Amplification Bias Control

Multiplex PCR assays can result in a bias in the total numbers of amplicons produced from a sample, given that certain primer sets may be more efficient in amplification than others. To overcome the problem of such biased utilization of subpopulations of amplification primers, methods can be used that provide a template composition for standardizing the amplification efficiencies of the members of an oligonucleotide primer set, where the primer set is capable of amplifying rearranged DNA encoding a plurality of TCRs in a biological sample that comprises DNA from lymphoid cells.

To that end, a template composition is used to standardize the various amplification efficiencies of the primer sets. The template composition can comprise a plurality of diverse template oligonucleotides of general formula (II):

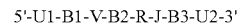   (II)

The constituent template oligonucleotides are diverse with respect to the nucleotide sequences of the individual template oligonucleotides. The individual template oligonucleotides can vary in nucleotide sequence considerably from one another as a function of significant sequence variability among the large number of possible TCR variable (V) and joining (J) region polynucleotides. Sequences of individual template oligonucleotide species can also vary from one another as a function of sequence differences in U1, U2, B (B1, B2 and B3) and R oligonucleotides that are included in a particular template within the diverse plurality of templates.

V is a polynucleotide comprising at least 20, 30, 60, 90, 120, 150, 180, or 210, and not more than 1000, 900, 800, 700, 600 or 500 contiguous nucleotides of an adaptive immune receptor variable (V) region encoding gene sequence, or the complement thereof, and in each of the plurality of template oligonucleotide sequences V comprises a unique oligonucleotide sequence.

J is a polynucleotide comprising at least 15-30, 31-60, 61-90, 91-120, or 120-150, and not more than 600, 500, 400, 300 or 200 contiguous nucleotides of an adaptive immune receptor joining (J) region encoding gene sequence, or the complement thereof, and in each of the plurality of template oligonucleotide sequences J comprises a unique oligonucleotide sequence.

U1 and U2 can be each either nothing or each comprise an oligonucleotide having, independently, a sequence that is selected from (i) a universal adaptor oligonucleotide sequence, and (ii) a sequencing platform-specific oligonucleotide sequence that is linked to and positioned 5' to the universal adaptor oligonucleotide sequence.

B1, B2 and B3 can be each either nothing or each comprise an oligonucleotide B that comprises a first and a second oligonucleotide barcode sequence of 3, 4, 5, 6, 7, 8, 9, 10, 11, 12, 13, 14, 15, 16, 17, 18, 19, 20, 25, 30, 35, 40, 45, 50, 60, 70, 80, 90, 100, 200, 300, 400, 500, 600, 700, 800, 900 or 1000 contiguous nucleotides (including all integer values therebetween), wherein in each of the plurality of template oligonucleotide sequences B comprises a unique oligonucleotide sequence in which (i) the first barcode sequence uniquely identifies the unique V oligonucleotide sequence of the template oligonucleotide and (ii) the second barcode sequence uniquely identifies the unique J oligonucleotide sequence of the template oligonucleotide.

R can be either nothing or comprises a restriction enzyme recognition site that comprises an oligonucleotide sequence that is absent from V, J, U1, U2, B1, B2 and B3.

Methods are used with the template composition for determining non-uniform nucleic acid amplification potential among members of a set of oligonucleotide amplification primers that are capable of amplifying productively rearranged DNA encoding one or a plurality of TCRs in a biological sample that comprises DNA from lymphoid cells of a subject. The method can include the steps of: (a) amplifying DNA of a template composition for standardizing amplification efficiency of an oligonucleotide primer set in a multiplex polymerase chain reaction (PCR) that comprises: (i) the template composition (II) described above, wherein each template oligonucleotide in the plurality of template oligonucleotides is present in a substantially equimolar amount; (ii) an oligonucleotide amplification primer set that is capable of amplifying productively rearranged DNA encoding one or a plurality of TCRs in a biological sample that comprises DNA from lymphoid cells of a subject.

The primer set can include: (1) in substantially equimolar amounts, a plurality of V-segment oligonucleotide primers that are each independently capable of specifically hybridizing to at least one polynucleotide encoding a TCR V-region polypeptide or to the complement thereof, wherein each V-segment primer comprises a nucleotide sequence of at least 15 contiguous nucleotides that is complementary to at least one functional TCR V region-encoding gene segment and wherein the plurality of V-segment primers specifically hybridize to substantially all functional TCR V region-encoding gene segments that are present in the template composition, and (2) in substantially equimolar amounts, a plurality of J-segment oligonucleotide primers that are each independently capable of specifically hybridizing to at least one polynucleotide encoding a TCR J-region polypeptide or to the complement thereof, wherein each J-segment primer comprises a nucleotide sequence of at least 15 contiguous nucleotides that is complementary to at least one functional TCR J region-encoding gene segment and wherein the plurality of J-segment primers specifically hybridize to substantially all functional TCR J region-encoding gene segments that are present in the template composition.

The V-segment and J-segment oligonucleotide primers are capable of promoting amplification in said multiplex polymerase chain reaction (PCR) of substantially all template oligonucleotides in the template composition to produce a multiplicity of amplified template DNA molecules, said multiplicity of amplified template DNA molecules being sufficient to quantify diversity of the template oligonucleotides in the template composition, and wherein each amplified template DNA molecule in the multiplicity of amplified template DNA molecules is less than 1000, 900, 800, 700, 600, 500, 400, 300, 200, 100, 90, 80 or 70 nucleotides in length.

Methods for determining non-uniform nucleic acid amplification potential may further include: (b) sequencing all or a sufficient portion of each of said multiplicity of amplified template DNA molecules to determine, for each unique template DNA molecule in said multiplicity of amplified template DNA molecules, (i) a template-specific oligonucleotide DNA sequence and (ii) a relative frequency of occurrence of the template oligonucleotide; and (c) comparing the relative frequency of occurrence for each unique template DNA sequence from said template composition, wherein a non-uniform frequency of occurrence for one or more template DNA sequences indicates non-uniform nucleic acid amplification potential among members of the set of oligonucleotide amplification primers.

Further details concerning the aforementioned bias control methods are provided in US2013/0253842, U.S. Pat. No. 9,150,905, US2015/0203897, and WO2013/169957, which are incorporated by reference in their entireties.

PCR Template Abundance Estimation

To estimate the average read coverage per input template in the multiplex PCR and sequencing approach, a set of synthetic TCR templates (as described above) can be used, comprising each combination of V.beta. and J.beta. gene segments. These synthetic molecules can be those described in general formula (II) above, and in US2013/0253842, U.S. Pat. No. 9,150,905, US2015/0203897, and WO2013/169957, which are incorporated by reference in their entireties.

These synthetic molecules can be included in each PCR reaction at very low concentration so that only some of the synthetic templates are observed. Using the known concentration of the synthetic template pool, the relationship between the number of observed unique synthetic molecules and the total number of synthetic molecules added to reaction can be simulated (this is very nearly one-to-one at the low concentrations that were used). The synthetic molecules allow calculation for each PCR reaction the mean number of sequencing reads obtained per molecule of PCR template, and an estimation of the number of T cells or B cells in the input material bearing each unique TCR rearrangement or Ig rearrangement, respectively.

Table 1 set forth below lists CDR3 sequences associated with COVID-19 with the indicated p-values. These sequences were identified from machine learning models developed on 784 COVID-19 cases versus 2447 controls. The amino acid sequence represents the TCRβ CDR3 segment of the TCR. V and J gene segment columns list V- and J-gene identities for TCR. V #### or J #### refers to a standard two level coding system [family]-[gene] for a particular part of the human genome that can be used as part of a TCR rearrangement formed in response to antigen exposure. The first two digits reflect a member of a family and the second two digits reflect a particular gene from within that family if present. So, by way of example, TCRBV14 would indicate a match of sequence to a specific family of variable (V) chain sequences where TCRBV14-01 indicates a more precise identification to a specific gene from within a family of variable chain sequences. The "HLA Association" column indicates the HLA from the subject associated with the obtained TCR sequence. The "Protein" column lists the SARS-CoV-2 protein bound by the TCR.

TABLE 1

COVID-19-associated TCRs

| TCRB CDR3 Amino Acid Sequence | SEQ ID NO: | V Gene Segment | J Gene Segment | HLA Association | Protein | Control Count (out of 2447) | Case Count (out of 784) | fet_p value |
|---|---|---|---|---|---|---|---|---|
| CASSQGNRANTEAFF | 1 | TCRBV14-01 | TCRBJ01-01 | DPA1*01:03+ DPB1*02:01 | NaN | 6 | 106 | 1.20E-59 |
| CSATSGHEQYF | 2 | TCRBV20-01 | TCRBJ02-07 | DQA1*05:05+ DQB1*03:01 | NaN | 25 | 123 | 3.40E-54 |
| CASSGTGSTDTQYF | 3 | TCRBV07-09 | TCRBJ02-03 | DRB3*02:02 | membrane_ glycoprotein | 27 | 119 | 1.41E-50 |
| CASTGTGSTDTQYF | 4 | TCRBV07-09 | TCRBJ02-03 | DRB3*02:02 | nucleocapsid_ phosphoprotein | 6 | 90 | 1.61E-49 |
| CSARSGHEQYF | 5 | TCRBV20-01 | TCRBJ02-07 | DQA1*05:05+ DQB1*03:01 | NaN | 157 | 205 | 2.74E-45 |
| CSASSGHEQYF | 6 | TCRBV20-01 | TCRBJ02-07 | DQA1*05:05+ DQB1*03:01 | NaN | 131 | 189 | 3.48E-45 |
| CASSESPTSTDTQYF | 7 | TCRBV10-02 | TCRBJ02-03 | DQA1*05:05+ DQB1*03:01 | membrane_ glycoprotein | 2 | 75 | 8.12E-45 |
| CSASSGHEAFF | 8 | TCRBV20-01 | TCRBJ01-01 | DQA1*05:05+ DQB1*03:01 | NaN | 12 | 91 | 1.34E-44 |
| CSARDWREETQYF | 9 | TCRBV20-X | TCRBJ02-05 | DQA1*01:01+ DQB1*05:01 | surface_ glycoprotein | 54 | 132 | 6.97E-44 |
| CASSLKLDTEAFF | 10 | TCRBV05-01 | TCRBJ01-01 | DQA1*05:01+ DQB1*02:01/ DRB1*03:01 | nucleocapsid_ phosphoprotein | 16 | 93 | 9.52E-43 |
| CSAKAGGRGETQYF | 11 | TCRBV20-X | TCRBJ02-05 | DPA1*01:03+ DPB1*02:01 | NaN | 3 | 71 | 5.42E-41 |
| CSARRQGVRGNQPQHF | 12 | TCRBV20-X | TCRBJ01-05 | DPA1*01:03+ DPB1*02:01 | NaN | 6 | 75 | 3.30E-40 |
| CAISERGQDEQYF | 13 | TCRBV10-03 | TCRBJ02-07 | DRB3*02:02 | nucleocapsid_ phosphoprotein | 11 | 78 | 1.21E-37 |
| CASSLKLDSPLHF | 14 | TCRBV05-01 | TCRBJ01-06 | DQA1*05:01+ DQB1*02:01/ DRB1*03:01 | ORF7a | 11 | 78 | 1.21E-37 |
| CASSPRLAGSSYNEQFF | 15 | TCRBV05-01 | TCRBJ02-01 | DPA1*01:03+ DPB1*04:01 | surface_ glycoprotein | 32 | 98 | 4.24E-36 |
| CASSYTGQGAEQYF | 16 | TCRBV06-05 | TCRBJ02-07 | DRB1*07:01 | NaN | 3 | 63 | 5.45E-36 |
| CASSLEGSTDTQYF | 17 | TCRBV07-09 | TCRBJ02-03 | DRB3*02:02 | surface_ glycoprotein | 322 | 265 | 2.30E-35 |
| CSAKAGGRGDTQYF | 18 | TCRBV20-X | TCRBJ02-03 | DPA1*01:03+ DPB1*02:01 | NaN | 10 | 72 | 6.93E-35 |
| CSARSGFEQYF | 19 | TCRBV20-01 | TCRBJ02-07 | DQA1*05:05+ DQB1*03:01 | NaN | 60 | 118 | 1.84E-34 |
| CASSTGDGYNSPLHF | 20 | TCRBV09-01 | TCRBJ01-06 | DQA1*02:01+ DQB1*02:02 | NaN | 0 | 52 | 2.80E-33 |
| CASSPPGQGEHGYTF | 21 | TCRBV18-01 | TCRBJ01-02 | DRB3*03:01 | nucleocapsid_ phosphoprotein | 2 | 55 | 3.26E-32 |
| CSARVGTATNEKLFF | 22 | TCRBV20-X | TCRBJ01-04 | DRB3*02:02 | NaN | 43 | 97 | 1.12E-30 |
| CASSSGDGYNSPLHF | 23 | TCRBV09-01 | TCRBJ01-06 | DQA1*02:01+ DQB1*02:02 | NaN | 1 | 50 | 2.08E-30 |
| CASSVDQGAKETQYF | 24 | TCRBV09-01 | TCRBJ02-05 | DRB5*01:01 | NaN | 2 | 52 | 2.40E-30 |
| CASSYTGQGAEAFF | 25 | TCRBV06-05 | TCRBJ01-01 | DRB1*07:01 | NaN | 21 | 75 | 1.83E-29 |

TABLE 1-continued

COVID-19-associated TCRs

| TCRB CDR3 Amino Acid Sequence | SEQ ID NO: | V Gene Segment | J Gene Segment | HLA Association | Protein | Control Count (out of 2447) | Case Count (out of 784) | fet_p value |
|---|---|---|---|---|---|---|---|---|
| CASSLNRGDYGYTF | 26 | TCRBV07-09 | TCRBJ01-02 | DRB3*02:02 | nucleocapsid_phosphoprotein | 53 | 102 | 2.54E-29 |
| CASSIVWTADNQPQHF | 27 | TCRBV19-01 | TCRBJ01-05 | DRB3*02:02 | surface_glycoprotein | 1 | 48 | 3.73E-29 |
| CASSLSAPQETQYF | 28 | TCRBV27-01 | TCRBJ02-05 | A*01:01 | ORF1ab | 15 | 68 | 4.21E-29 |
| CASSESPVSTDTQYF | 29 | TCRBV10-02 | TCRBJ02-03 | DRB1*11:04 | membrane_glycoprotein | 0 | 45 | 7.92E-29 |
| CASSLALGGAGNQPQHF | 30 | TCRBV07-02 | TCRBJ01-05 | DRB1*01:01 | NaN | 6 | 56 | 1.04E-28 |
| CASSILGSANTGELFF | 31 | TCRBV19-01 | TCRBJ02-02 | DQA1*01:02+ DQB1*05:02 | membrane_glycoprotein | 14 | 66 | 1.30E-28 |
| CASSLKMDTEAFF | 32 | TCRBV05-01 | TCRBJ01-01 | DQA1*05:01+ DQB1*02:01/ DRB1*03:01 | nucleocapsid_phosphoprotein | 3 | 51 | 1.40E-28 |
| CASTLEGSTDTQYF | 33 | TCRBV07-09 | TCRBJ02-03 | DRB3*02:02 | nucleocapsid_phosphoprotein | 1 | 47 | 1.58E-28 |
| CSAREGGVYSNQPQHF | 34 | TCRBV20-X | TCRBJ01-05 | DRB3*02:02 | NaN | 17 | 69 | 1.89E-28 |
| CASSYTGQGAGYTF | 35 | TCRBV06-05 | TCRBJ01-02 | DRB1*07:01 | NaN | 20 | 71 | 7.47E-28 |
| CSARDDRLYSNQPQHF | 36 | TCRBV20-X | TCRBJ01-05 | DQA1*01:01+ DQB1*05:01 | surface_glycoprotein | 21 | 70 | 8.64E-27 |
| CSARRDSRTDTQYF | 37 | TCRBV20-X | TCRBJ02-03 | DRB5*01:01 | surface_glycoprotein | 41 | 86 | 4.30E-26 |
| CAISARGQDEQYF | 38 | TCRBV10-03 | TCRBJ02-07 | DRB3*02:02 | NaN | 1 | 43 | 4.99E-26 |
| CASSILGAANTGELFF | 39 | TCRBV19-01 | TCRBJ02-02 | DQA1*01:02+ DQB1*05:02 | membrane_glycoprotein | 14 | 61 | 7.79E-26 |
| CSATSGHEQFF | 40 | TCRBV20-01 | TCRBJ02-01 | DQA1*05:05+ DQB1*03:01 | ORF10 | 11 | 57 | 1.66E-25 |
| CASSLKGSTDTQYF | 41 | TCRBV07-09 | TCRBJ02-03 | DRB3*02:02 | nucleocapsid_phosphoprotein | 58 | 97 | 2.46E-25 |
| CASSRTGTGSSYNSPLHF | 42 | TCRBV12-X | TCRBJ01-06 | DRB5*02:02 | surface_glycoprotein | 2 | 43 | 8.68E-25 |
| CSARPGGVYSNQPQHF | 43 | TCRBV20-X | TCRBJ01-05 | DRB1*11:01 | membrane_glycoprotein | 4 | 46 | 1.51E-24 |
| CSARAGGVYSNQPQHF | 44 | TCRBV20-X | TCRBJ01-05 | DRB3*02:02 | membrane_glycoprotein | 4 | 46 | 1.51E-24 |
| CASSTPDRGNNQPQHF | 45 | TCRBV19-01 | TCRBJ01-05 | DRB5*01:01 | surface_glycoprotein | 3 | 44 | 2.55E-24 |
| CSAQTGVNQPQHF | 46 | TCRBV20-X | TCRBJ01-05 | DRB3*02:02 | membrane_glycoprotein | 102 | 121 | 1.34E-23 |
| CASSLKQDTEAFF | 47 | TCRBV05-01 | TCRBJ01-01 | DQA1*05:01+ DQB1*02:01/ DRB1*03:01 | nucleocapsid_phosphoprotein | 19 | 62 | 1.35E-23 |
| CASSYTGQGQPQHF | 48 | TCRBV06-05 | TCRBJ01-05 | DRB1*07:01 | NaN | 18 | 61 | 1.38E-23 |
| CASSDRGPNNEQFF | 49 | TCRBV27-01 | TCRBJ02-01 | A*01:01 | ORF1ab | 4 | 44 | 2.37E-23 |

TABLE 1-continued

COVID-19-associated TCRs

| TCRB CDR3 Amino Acid Sequence | SEQ ID NO: | V Gene Segment | J Gene Segment | HLA Association | Protein | Control Count (out of 2447) | Case Count (out of 784) | fet_p value |
|---|---|---|---|---|---|---|---|---|
| CASSQERGGNQPQHF | 50 | TCRBV04-02 | TCRBJ01-05 | DQA1*05:05+ DQB1*03:01 | nucleocapsid_ phosphoprotein | 71 | 101 | 3.00E-23 |
| CASSPPGLYGYTF | 51 | TCRBV07-08 | TCRBJ01-02 | DRB5*01:01 | membrane_ glycoprotein | 16 | 58 | 4.65E-23 |
| CSAREGTASTDTQYF | 52 | TCRBV20-X | TCRBJ02-03 | DRB3*02:02 | NaN | 63 | 95 | 6.05E-23 |
| CASSYPEMNTEAFF | 53 | TCRBV06-06 | TCRBJ01-01 | DRB1*11:01 | nucleocapsid_ phosphoprotein | 27 | 68 | 6.30E-23 |
| CSVRTGTGNTGELFF | 54 | TCRBV29-01 | TCRBJ02-02 | DQA1*05:05+ DQB1*03:01 | surface_ glycoprotein | 18 | 59 | 1.56E-22 |
| CASSESRTENSPLHF | 55 | TCRBV10-01 | TCRBJ01-06 | DRB1*01:01 | membrane_ glycoprotein | 3 | 41 | 1.65E-22 |
| CASSLGAPQETQYF | 56 | TCRBV27-01 | TCRBJ02-05 | A*01:01 | ORF1ab | 8 | 48 | 1.79E-22 |
| CSARRDSRADTQYF | 57 | TCRBV20-X | TCRBJ02-03 | DRB5*01:01 | surface_ glycoprotein | 8 | 48 | 1.79E-22 |
| CATSDPRDRTYEQYF | 58 | TCRBV24-01 | TCRBJ02-07 | DRB1*07:01 | nucleocapsid_ phosphoprotein | 46 | 82 | 1.89E-22 |
| CSAKSGGRGETQYF | 59 | TCRBV20-X | TCRBJ02-05 | DPA1*01:03+ DPB1*02:01 | NaN | 1 | 37 | 2.67E-22 |
| CASSLVWGNQPQHF | 60 | TCRBV27-01 | TCRBJ01-05 | DRB1*07:01 | surface_ glycoprotein | 34 | 72 | 4.74E-22 |
| CASSLEGGSYGYTF | 61 | TCRBV13-01 \| | TCRBJ01-02 | DQA1*01:02+ DQB1*06:02 | nucleocapsid_ phosphoprotein | 27 | 66 | 6.17E-22 |
| CASSLDQGAKETQYF | 62 | TCRBV05-01 | TCRBJ02-05 | DRB5*01:01 | nucleocapsid_ phosphoprotein | 3 | 40 | 6.61E-22 |
| CATSGTGSTDTQYF | 63 | TCRBV07-09 | TCRBJ02-03 | DRB3*02:02 | nucleocapsid_ phosphoprotein | 0 | 34 | 7.07E-22 |
| CASTGQGSTDTQYF | 64 | TCRBV07-09 | TCRBJ02-03 | DRB3*02:02 | nucleocapsid_ phosphoprotein | 13 | 52 | 1.64E-21 |
| CSAKSGHEQYF | 65 | TCRBV20-01 | TCRBJ02-07 | DQA1*03:03+ DQB1*03:01 | NaN | 17 | 56 | 1.79E-21 |
| CASSYRGANGYTF | 66 | TCRBV06-02/06-03 | TCRBJ01-02 | DPA1*01:03+ DPB1*04:02 | surface_ glycoprotein | 8 | 46 | 2.44E-21 |
| CSARRGGPTNTEAFF | 67 | TCRBV20-X | TCRBJ01-01 | DQA1*05:05+ DQB1*03:01 | surface_ glycoprotein | 0 | 33 | 3.01E-21 |
| CASSPSSGGNTGELFF | 68 | TCRBV10-01 | TCRBJ02-02 | DRB4*01:03 | surface_ glycoprotein | 2 | 37 | 4.02E-21 |
| CSALPGGVSNQPQHF | 69 | TCRBV20-X | TCRBJ01-05 | DQA1*05:05+ DQB1*03:01 | NaN | 2 | 37 | 4.02E-21 |
| CSARWGGRGETQYF | 70 | TCRBV20-X | TCRBJ02-05 | DPA1*01:03+ DPB1*02:01 | NaN | 4 | 40 | 5.61E-21 |
| CSVALGVNQPQHF | 71 | TCRBV29-01 | TCRBJ01-05 | DRB1*11:01 | NaN | 15 | 53 | 6.12E-21 |
| CASSLVTGASTDTQYF | 72 | TCRBV07-08 | TCRBJ02-03 | DQA1*01:01+ DQB1*05:01 | ORF8 | 5 | 41 | 1.02E-20 |
| CASSRGTSGFQETQYF | 73 | TCRBV04-02 | TCRBJ02-05 | DQA1*02:01+ DQB1*02:02 | NaN | 3 | 38 | 1.05E-20 |

TABLE 1-continued

COVID-19-associated TCRs

| TCRB CDR3 Amino Acid Sequence | SEQ ID NO: | V Gene Segment | J Gene Segment | HLA Association | Protein | Control Count (out of 2447) | Case Count (out of 784) | fet_p value |
|---|---|---|---|---|---|---|---|---|
| CASSYTGQGSGYTF | 74 | TCRBV06-05 | TCRBJ01-02 | DRB1*07:01 | NaN | 41 | 74 | 1.73E-20 |
| CSAKQGANTGELFF | 75 | TCRBV20-X | TCRBJ02-02 | DRB1*07:01 | surface_glycoprotein | 69 | 93 | 1.84E-20 |
| CATTGTGSTDTQYF | 76 | TCRBV07-09 | TCRBJ02-03 | DRB3*02:02 | NaN | 1 | 34 | 1.91E-20 |
| CASSIGLAGLTQETQYF | 77 | TCRBV19-01 | TCRBJ02-05 | DQA1*05:05+ DQB1*03:01 | membrane_glycoprotein | 1 | 34 | 1.91E-20 |
| CASSEGASNQPQHF | 78 | TCRBV06-01 | TCRBJ01-05 | DRB5*01:01 | surface_glycoprotein | 112 | 118 | 2.77E-20 |
| CSARDWRGETQYF | 79 | TCRBV20-X | TCRBJ02-05 | DQA1*01:01+ DQB1*05:01 | surface_glycoprotein | 46 | 77 | 3.28E-20 |
| CSARDWKEETQYF | 80 | TCRBV20-X | TCRBJ02-05 | DQA1*01:01+ DQB1*05:01 | surface_glycoprotein | 5 | 40 | 3.90E-20 |
| CASRRQVYGANVLTF | 81 | TCRBV19-01 | TCRBJ02-06 | DRB1*13:01 | NaN | 0 | 31 | 5.45E-20 |
| CASSTGGRLYGYTF | 82 | TCRBV06-05\|TCRBJ01-02 | | DPA1*01:03+ DPB1*02:01 | NaN | 4 | 38 | 8.48E-20 |
| CASSRTGLRSSYNSPLHF | 83 | TCRBV12-X | TCRBJ01-06 | DRB5*02:02 | surface_glycoprotein | 2 | 34 | 2.66E-19 |
| CASSPRLAGGSYNEQFF | 84 | TCRBV05-05 | TCRBJ02-01 | DPA1*01:03+ DPB1*04:01 | NaN | 4 | 37 | 3.28E-19 |
| CASSLRYQETQYF | 85 | TCRBV05-06 | TCRBJ02-05 | DRB3*02:02 | ORF3a | 47 | 75 | 4.99E-19 |
| CSARWGGRGDTQYF | 86 | TCRBV20-X | TCRBJ02-03 | DPA1*01:03+ DPB1*02:01 | NaN | 5 | 38 | 5.63E-19 |
| CSAPPGGQYSNQPQHF | 87 | TCRBV20-X | TCRBJ01-05 | DQA1*05:05+ DQB1*03:01 | NaN | 3 | 35 | 6.44E-19 |
| CASSVRDRVNTGELFF | 88 | TCRBV09-01 | TCRBJ02-02 | DPA1*01:03+ DPB1*04:01 | surface_glycoprotein | 22 | 55 | 1.24E-18 |
| CSAREGGAYSNQPQHF | 89 | TCRBV20-X | TCRBJ01-05 | DRB3*02:02 | NaN | 20 | 53 | 1.64E-18 |
| CSAKRGGRGETQYF | 90 | TCRBV20-X | TCRBJ02-05 | DPA1*01:03+ DPB1*02:01 | NaN | 5 | 37 | 2.13E-18 |
| CASSYPEDNSPLHF | 91 | TCRBV06-06 | TCRBJ01-06 | DQA1*04:01+ DQB1*04:02 | nucleocapsid_phosphoprotein | 16 | 49 | 2.42E-18 |
| CASSPDIEAFF | 92 | TCRBV07-09 | TCRBJ01-01 | A*02:01 | surface_glycoprotein | 28 | 59 | 3.67E-18 |
| CASSQAGGSTDTQYF | 93 | TCRBV07-03 | TCRBJ02-03 | DRB5*01:01 | surface_glycoprotein | 22 | 54 | 3.83E-18 |
| CASSVEGGDYQETQYF | 94 | TCRBV09-01 | TCRBJ02-05 | DQA1*05:01+ DQB1*02:01/ DRB1*03:01 | surface_glycoprotein | 0 | 28 | 4.15E-18 |
| CASSRAGGSTDTQYF | 95 | TCRBV07-03 | TCRBJ02-03 | DRB5*01:01 | surface_glycoprotein | 52 | 76 | 5.25E-18 |
| CASSLLSTANTGELFF | 96 | TCRBV28-01 | TCRBJ02-02 | DQA1*01:02+ DQB1*05:01 | membrane_glycoprotein | 1 | 30 | 5.53E-18 |
| CASSYAEMNTEAFF | 97 | TCRBV06-06 | TCRBJ01-01 | DRB1*11:01 | nucleocapsid_phosphoprotein | 25 | 56 | 6.83E-18 |

TABLE 1-continued

COVID-19-associated TCRs

| TCRB CDR3 Amino Acid Sequence | SEQ ID NO: | V Gene Segment | J Gene Segment | HLA Association | Protein | Control Count (out of 2447) | Case Count (out of 784) | fet_p value |
|---|---|---|---|---|---|---|---|---|
| CSASSGHEQFF | 98 | TCRBV20-01 | TCRBJ02-01 | DQA1*05:05+ DQB1*03:01 | NaN | 44 | 70 | 9.03E-18 |
| CSARSGHEQFF | 99 | TCRBV20-01 | TCRBJ02-01 | DQA1*05:05+ DQB1*03:01 | NaN | 36 | 64 | 1.20E-17 |
| CASSLGLAYTDTQYF | 100 | TCRBV07-02 | TCRBJ02-03 | DRB3*02:02 | NaN | 39 | 66 | 1.44E-17 |
| CASSRTGLGSSYNSPLHF | 101 | TCRBV12-X | TCRBJ01-06 | DRB5*02:02 | NaN | 0 | 27 | 1.76E-17 |
| CASSRTGARSSYNSPLHF | 102 | TCRBV12-X | TCRBJ01-06 | DRB5*02:02 | NaN | 0 | 27 | 1.76E-17 |
| CASSRTGVRSSYNSPLHF | 103 | TCRBV12-X | TCRBJ01-06 | DRB5*02:02 | ORF3a | 0 | 27 | 1.76E-17 |
| CASTREGSTDTQYF | 104 | TCRBV07-09 | TCRBJ02-03 | DRB3*02:02 | ORF7a | 4 | 34 | 1.86E-17 |
| CATQPGQGNTEAFF | 105 | TCRBV24-01 | TCRBJ01-01 | DRB1*15:01 | NaN | 1 | 29 | 2.27E-17 |
| CASSDRGPNQPQHF | 106 | TCRBV27-01 | TCRBJ01-05 | A*01:01 | ORF1ab | 24 | 54 | 2.49E-17 |
| CASSLQGSTDTQYF | 107 | TCRBV07-09 | TCRBJ02-03 | DRB3*02:02 | nucleocapsid_phosphoprotein | 218 | 161 | 5.39E-17 |
| CATSDLPSGPYNEQFF | 108 | TCRBV24-01 | TCRBJ02-01 | DRB1*07:01 | surface_glycoprotein | 7 | 37 | 5.71E-17 |
| CSALPGLDTDTQYF | 109 | TCRBV20-X | TCRBJ02-03 | DQA1*01:01+ DQB1*05:01 | surface_glycoprotein | 4 | 33 | 7.07E-17 |
| CASSRTGFRSSYNSPLHF | 110 | TCRBV12-X | TCRBJ01-06 | DRB5*02:02 | NaN | 0 | 26 | 7.43E-17 |
| CAWSDKSSSYNSPLHF | 111 | TCRBV30-01 | TCRBJ01-06 | DQA1*02:01+ DQB1*02:02 | NaN | 0 | 26 | 7.43E-17 |
| CASSLLAGDKNIQYF | 112 | TCRBV05-06 | TCRBJ02-04 | DRB5*01:01 | nucleocapsid_phosphoprotein | 9 | 39 | 8.16E-17 |
| CASSPTGAVQPQHF | 113 | TCRBV18-01 | TCRBJ01-05 | DRB3*03:01 | NaN | 9 | 39 | 8.16E-17 |
| CASSYTGQGVGYTF | 114 | TCRBV06-05 | TCRBJ01-02 | DRB1*07:01 | NaN | 14 | 44 | 9.36E-17 |
| CASSYSEDNQPQHF | 115 | TCRBV06-06 | TCRBJ01-05 | DQA1*04:01+ DQB1*04:02 | nucleocapsid_phosphoprotein | 11 | 41 | 9.56E-17 |
| CASSQDSPNTEAFF | 116 | TCRBV04-01 | TCRBJ01-01 | DRB5*01:01 | NaN | 39 | 64 | 1.08E-16 |
| CSARDRGVYSNQPQHF | 117 | TCRBV20-X | TCRBJ01-05 | DRB3*02:02 | membrane_glycoprotein | 22 | 51 | 1.09E-16 |
| CAWSTRENQPQHF | 118 | TCRBV30-01 | TCRBJ01-05 | DRB3*02:02 | nucleocapsid_phosphoprotein | 45 | 68 | 1.26E-16 |
| CASSLAPNTDTQYF | 119 | TCRBV05-05 | TCRBJ02-03 | DQA1*05:01+ DQB1*02:01/ DRB1*03:01 | NaN | 3 | 31 | 1.50E-16 |
| CASSGEGSTDTQYF | 120 | TCRBV07-09 | TCRBJ02-03 | DRB3*02:02 | NaN | 6 | 35 | 1.58E-16 |
| CASSYSEDNSPLHF | 121 | TCRBV06-06 | TCRBJ01-06 | DQA1*04:01+ DQB1*04:02 | nucleocapsid_phosphoprotein | 7 | 36 | 2.05E-16 |
| CSVRSGHEQYF | 122 | TCRBV20-01 | TCRBJ02-07 | DQA1*03:03+ DQB1*03:01 | NaN | 4 | 32 | 2.68E-16 |
| CAISDRGQDTQYF | 123 | TCRBV10-03 | TCRBJ02-03 | DRB3*02:02 | nucleocapsid_phosphoprotein | 14 | 43 | 3.05E-16 |

TABLE 1-continued

COVID-19-associated TCRs

| TCRB CDR3 Amino Acid Sequence | SEQ ID NO: | V Gene Segment | J Gene Segment | HLA Association | Protein | Control Count (out of 2447) | Case Count (out of 784) | fet_p value |
|---|---|---|---|---|---|---|---|---|
| CASSRTGVGSSYNSPLHF | 124 | TCRBV12-X | TCRBJ01-06 | DRB5*02:02 | membrane_glycoprotein | 0 | 25 | 3.14E-16 |
| CASSLGQGAFTDTQYF | 125 | TCRBV05-05 | TCRBJ02-03 | A*01:01 | ORF1ab | 0 | 25 | 3.14E-16 |
| CASSLNRGRSGELFF | 126 | TCRBV28-01 | TCRBJ02-02 | DPA1*01:03+ DPB1*04:01 | surface_glycoprotein | 1 | 27 | 3.80E-16 |
| CASSRTGGGSSYNSPLHF | 127 | TCRBV12-X | TCRBJ01-06 | DRB5*02:02 | NaN | 1 | 27 | 3.80E-16 |
| CASSDRGPADTQYF | 128 | TCRBV27-01 | TCRBJ02-03 | A*01:01 | ORF1ab | 1 | 27 | 3.80E-16 |
| CASSLSISGNTIYF | 129 | TCRBV11-02 | TCRBJ01-03 | DRB1*11:01 | NaN | 64 | 79 | 3.92E-16 |
| CASSYPEDNQPQHF | 130 | TCRBV06-06 | TCRBJ01-05 | DQA1*04:01+ DQB1*04:02 | nucleocapsid_phosphoprotein | 6 | 34 | 5.75E-16 |
| CASSQGVGYTF | 131 | TCRBV04-01 | TCRBJ01-02 | DPA1*01:03+ DPB1*04:01 | surface_glycoprotein | 178 | 138 | 9.89E-16 |
| CASRTSGPSYNEQFF | 132 | TCRBV19-01 | TCRBJ02-01 | DRB1*01:01 | membrane_glycoprotein | 13 | 41 | 1.05E-15 |
| CASSYAEDNSPLHF | 133 | TCRBV06-06 | TCRBJ01-06 | DQA1*04:01+ DQB1*04:02 | nucleocapsid_phosphoprotein | 2 | 28 | 1.08E-15 |
| CASRESPTSTDTQYF | 134 | TCRBV10-02 | TCRBJ02-03 | DQA1*05:05+ DQB1*03:01 | NaN | 0 | 24 | 1.33E-15 |
| CASSRTGQGSSYNSPLHF | 135 | TCRBV12-X | TCRBJ01-06 | DRB5*02:02 | surface_glycoprotein | 0 | 24 | 1.33E-15 |
| CSALGGLAGVSDTQYF | 136 | TCRBV20-X | TCRBJ02-03 | DPA1*01:03+ DPB1*02:01 | surface_glycoprotein | 0 | 24 | 1.33E-15 |
| CASSYPELNTEAFF | 137 | TCRBV06-06 | TCRBJ01-01 | DRB1*11:01 | nucleocapsid_phosphoprotein | 20 | 47 | 1.43E-15 |
| CASSRTGLKSSYNSPLHF | 138 | TCRBV12-X | TCRBJ01-06 | DRB5*02:02 | NaN | 1 | 26 | 1.55E-15 |
| CASSVGGGEIYGYTF | 139 | TCRBV09-01 | TCRBJ01-02 | DRB1*01:01 | membrane_glycoprotein | 3 | 29 | 2.24E-15 |
| CASSESLGYTF | 140 | TCRBV06-01 | TCRBJ01-02 | DPA1*01:03+ DPB1*04:02 | ORF3a | 31 | 55 | 2.80E-15 |
| CASRGANEQFF | 141 | TCRBV03-01/03-02 | TCRBJ02-01 | DRB1*07:01 | NaN | 31 | 55 | 2.80E-15 |
| CASSIRSGTSTDTQYF | 142 | TCRBV19-01 | TCRBJ02-03 | DRB1*01:01 | membrane_glycoprotein | 22 | 48 | 2.94E-15 |
| CASSLKSDSPLHF | 143 | TCRBV05-01 | TCRBJ01-06 | DQA1*05:01+ DQB1*02:01/ DRB1*03:01 | NaN | 14 | 41 | 3.17E-15 |
| CSARAGHEQYF | 144 | TCRBV20-01 | TCRBJ02-07 | DQA1*05:05+ DQB1*03:01 | NaN | 98 | 96 | 3.24E-15 |
| CASSYAEPNTEAFF | 145 | TCRBV06-06 | TCRBJ01-01 | DRB1*11:01 | nucleocapsid_phosphoprotein | 4 | 30 | 3.81E-15 |
| CSARAGVQETQYF | 146 | TCRBV20-X | TCRBJ02-05 | DRB4*01:03 | surface_glycoprotein | 152 | 123 | 5.46E-15 |
| CASSLVTGHSTDTQYF | 147 | TCRBV07-08 | TCRBJ02-03 | DQA1*01:02+ DQB1*05:01 | surface_glycoprotein | 0 | 23 | 5.59E-15 |

TABLE 1-continued

COVID-19-associated TCRs

| TCRB CDR3 Amino Acid Sequence | SEQ ID NO: | V Gene Segment | J Gene Segment | HLA Association | Protein | Control Count (out of 2447) | Case Count (out of 784) | fet_p value |
|---|---|---|---|---|---|---|---|---|
| CASSRTGRGSSYNSPLHF | 148 | TCRBV12-X | TCRBJ01-06 | DRB5*02:02 | surface_glycoprotein | 1 | 25 | 6.31E-15 |
| CSARDGGVYSNQPQHF | 149 | TCRBV20-X | TCRBJ01-05 | DRB1*11:01 | NaN | 22 | 47 | 8.67E-15 |
| CASSPRGGGNTEAFF | 150 | TCRBV28-01 | TCRBJ01-01 | DQA1*05:01+ DQB1*02:01/ DRB1*03:01 | membrane glycoprotein | 54 | 69 | 1.18E-14 |
| CASSYMESNQPQHF | 151 | TCRBV06-06 | TCRBJ01-05 | DRB1*11:01 | nucleocapsid_phosphoprotein | 10 | 36 | 1.19E-14 |
| CASSGQGSTDTQYF | 152 | TCRBV07-09 | TCRBJ02-03 | DRB3*02:02 | nucleocapsid_phosphoprotein | 25 | 49 | 1.29E-14 |
| CASSYPESNTEAFF | 153 | TCRBV06-06 | TCRBJ01-01 | DRB1*11:01 | nucleocapsid_phosphoprotein | 4 | 29 | 1.43E-14 |
| CASSQAGGLTDTQYF | 154 | TCRBV07-03 | TCRBJ02-03 | DRB5*01:01 | NaN | 4 | 29 | 1.43E-14 |
| CASRQGAKTQYF | 155 | TCRBV06-X | TCRBJ02-05 | DRB5*01:01 | surface_glycoprotein | 4 | 29 | 1.43E-14 |
| CSARIGTATNEKLFF | 156 | TCRBV20-X | TCRBJ01-04 | DQA1*05:05+ DQB1*03:01 | NaN | 5 | 30 | 2.06E-14 |
| CASSFSGGLSPLHF | 157 | TCRBV12-X | TCRBJ01-06 | DRB3*01:01 | surface_glycoprotein | 5 | 30 | 2.06E-14 |
| CSARVGTASTDTQYF | 158 | TCRBV20-X | TCRBJ02-03 | DQA1*05:05+ DQB1*03:01 | NaN | 60 | 72 | 2.18E-14 |
| CASSRTGFGSSYNSPLHF | 159 | TCRBV12-X | TCRBJ01-06 | DRB5*02:02 | NaN | 0 | 22 | 2.35E-14 |
| CASSIDPDREKLFF | 160 | TCRBV19-01 | TCRBJ01-04 | DRB4*01:03 | surface_glycoprotein | 1 | 24 | 2.56E-14 |
| CASSQEQGRAEAFF | 161 | TCRBV14-01 | TCRBJ01-01 | DPA1*01:03+ DPB1*04:01 | surface_glycoprotein | 3 | 27 | 3.29E-14 |
| CSANSGHEQYF | 162 | TCRBV20-01 | TCRBJ02-07 | DRB3*02:02 | NaN | 9 | 34 | 3.89E-14 |
| CSAREGSASTDTQYF | 163 | TCRBV20-X | TCRBJ02-03 | DQA1*05:05+ DQB1*03:01 | NaN | 24 | 47 | 4.66E-14 |
| CSVGLGVNQPQHF | 164 | TCRBV29-01 | TCRBJ01-05 | DRB1*11:01 | NaN | 28 | 50 | 4.79E-14 |
| CSAKTSGRGETQYF | 165 | TCRBV20-X | TCRBJ02-05 | DPA1*01:03+ DPB1*02:01 | NaN | 47 | 63 | 4.88E-14 |
| CASSLALGEGSPLHF | 166 | TCRBV07-02 | TCRBJ01-06 | DRB1*01:01 | membrane_glycoprotein | 4 | 28 | 5.31E-14 |
| CASRTQQGNQPQHF | 167 | TCRBV06-05 | TCRBJ01-05 | DPA1*01:03+ DPB1*04:02 | NaN | 4 | 28 | 5.31E-14 |
| CASSAGRGDGYTF | 168 | TCRBV05-01 | TCRBJ01-02 | DPA1*01:03+ DPB1*02:01 | surface_glycoprotein | 62 | 72 | 6.17E-14 |
| CSAREGQFSGANVLTF | 169 | TCRBV20-X | TCRBJ02-06 | DPA1*01:03+ DPB1*02:01 | NaN | 2 | 25 | 6.58E-14 |
| CASSLGTGGSYNEQFF | 170 | TCRBV02-01 | TCRBJ02-01 | DRB5*01:01 | NaN | 2 | 25 | 6.58E-14 |
| CSATRDRRTYNEQFF | 171 | TCRBV20-X | TCRBJ02-01 | DRB5*01:01 | surface_glycoprotein | 2 | 25 | 6.58E-14 |

TABLE 1-continued

COVID-19-associated TCRs

| TCRB CDR3 Amino Acid Sequence | SEQ ID NO: | V Gene Segment | J Gene Segment | HLA Association | Protein | Control Count (out of 2447) | Case Count (out of 784) | fet_p value |
|---|---|---|---|---|---|---|---|---|
| CASSPRDRVNTGELFF | 172 | TCRBV09-01 | TCRBJ02-02 | DPA1*01:03+ DPB1*04:01 | surface_ glycoprotein | 26 | 48 | 8.06E-14 |
| CSARTGTASTDTQYF | 173 | TCRBV20-X | TCRBJ02-03 | DQA1*05:05+ DQB1*03:01 | NaN | 21 | 44 | 9.20E-14 |
| CASSPDRGKTDTQYF | 174 | TCRBV07-02 | TCRBJ02-03 | DQA1*01:01+ DQB1*05:01 | membrane_ glycoprotein | 0 | 21 | 9.90E-14 |
| CASSYMEDNQPQHF | 175 | TCRBV06-06 | TCRBJ01-05 | DQA1*04:01+ DQB1*04:02 | NaN | 0 | 21 | 9.90E-14 |
| CASSLVTGWDTDTQYF | 176 | TCRBV07-08 | TCRBJ02-03 | DQA1*01:01+ DQB1*05:01 | surface_ glycoprotein | 0 | 21 | 9.90E-14 |
| CSATRDRRNTGELFF | 177 | TCRBV20-X | TCRBJ02-02 | DRB5*01:01 | surface_ glycoprotein | 1 | 23 | 1.04E-13 |
| CSATLDRRSYNEQFF | 178 | TCRBV20-X | TCRBJ02-01 | DRB5*01:01 | surface_ glycoprotein | 1 | 23 | 1.04E-13 |
| CASMNREDGYTF | 179 | TCRBV25-01 | TCRBJ01-02 | DRB3*02:02 | membrane_ glycoprotein | 1 | 23 | 1.04E-13 |
| CASSLSSPQETQYF | 180 | TCRBV27-01 | TCRBJ02-05 | A*01:01 | ORF1ab | 47 | 62 | 1.22E-13 |
| CASSYAESNQPQHF | 181 | TCRBV06-06 | TCRBJ01-05 | DQA1*04:01+ DQB1*04:02 | nucleocapsid_ phosphoprotein | 12 | 36 | 1.22E-13 |
| CSARKDSRTDTQYF | 182 | TCRBV20-X | TCRBJ02-03 | DRB1*15:01 | surface_glyc oprotein | 3 | 26 | 1.25E-13 |
| CASSPDRGKTDTQYF | 174 | TCRBV07-03 | TCRBJ02-03 | DQA1*01:01+ DQB1*05:01 | membrane_ glycoprotein | 3 | 26 | 1.25E-13 |
| CAISLSGGDYEQYF | 183 | TCRBV10-03\| | TCRBJ02-07 | DRB1*01:01 | membrane_ glycoprotein | 3 | 26 | 1.25E-13 |
| CSAKWGGRGETQYF | 184 | TCRBV20-X | TCRBJ02-05 | DPA1*01:03+ DPB1*02:01 | NaN | 9 | 33 | 1.31E-13 |
| CASSSGDSYNSPLHF | 185 | TCRBV09-01 | TCRBJ01-06 | DQA1*05:01+ DQB1*02:01/ DRB1*03:01 | NaN | 10 | 34 | 1.32E-13 |
| CASSYSEGNSPLHF | 186 | TCRBV06-06 | TCRBJ01-06 | DRB1*11:01 | nucleocapsid_ phosphoprotein | 41 | 58 | 1.35E-13 |
| CASSPRLAGSSYNEQFF | 15 | TCRBV05-05 | TCRBJ02-01 | DPA1*01:03+ DPB1*04:01 | NaN | 4 | 27 | 1.97E-13 |
| CSALEGGTGNQPQHF | 187 | TCRBV20-X | TCRBJ01-05 | DRB1*11:01 | NaN | 4 | 27 | 1.97E-13 |
| CASSIRGQGAISSYNEQFF | 188 | TCRBV19-01 | TCRBJ02-01 | DRB1*13:01 | NaN | 4 | 27 | 1.97E-13 |
| CASREGGSNQPQHF | 189 | TCRBV10-02 | TCRBJ01-05 | DRB1*07:01 | surface_ glycoprotein | 17 | 40 | 2.01E-13 |
| CASSLGSPQETQYF | 190 | TCRBV27-01 | TCRBJ02-05 | A*01:01 | ORF1ab | 16 | 39 | 2.37E-13 |
| CAWSGLAGGAQETQYF | 191 | TCRBV30-01 | TCRBJ02-05 | DPA1*01:03+ DPB1*02:01 | NaN | 2 | 24 | 2.57E-13 |
| CASSYTGQGQGYTF | 192 | TCRBV06-05 | TCRBJ01-02 | DRB1*07:01 | NaN | 2 | 24 | 2.57E-13 |
| CASSWTEGSYEQYF | 193 | TCRBV28-01 | TCRBJ02-07 | A*01:01 | ORF1ab | 2 | 24 | 2.57E-13 |
| CASSLEQGRNTEAFF | 194 | TCRBV18-01 | TCRBJ01-01 | DQA1*05:05+ DQB1*03:01 | nucleocapsid_ phosphoprotein | 5 | 28 | 2.71E-13 |

TABLE 1-continued

COVID-19-associated TCRs

| TCRB CDR3 Amino Acid Sequence | SEQ ID NO: | V Gene Segment | J Gene Segment | HLA Association | Protein | Control Count (out of 2447) | Case Count (out of 784) | fet_p value |
|---|---|---|---|---|---|---|---|---|
| CSARDWRQETQYF | 195 | TCRBV20-X | TCRBJ02-05 | DQA1*01:01+ DQB1*05:01 | surface_ glycoprotein | 41 | 57 | 3.41E-13 |
| CASSPRSAGPQETQYF | 196 | TCRBV18-01 | TCRBJ02-05 | DRB1*01:01 | NaN | 0 | 20 | 4.16E-13 |
| CAISSRGQDEQYF | 197 | TCRBV10-03 | TCRBJ02-07 | DRB3*02:02 | nucleocapsid_ phosphoprotein | 0 | 20 | 4.16E-13 |
| CASSLKASGRGTDTQYF | 198 | TCRBV12-X | TCRBJ02-03 | DRB5*01:01 | NaN | 0 | 20 | 4.16E-13 |
| CSARTGTGNAGELFF | 199 | TCRBV20-X | TCRBJ02-02 | DQA1*05:05+ DQB1*03:01 | nucleocapsid_ phosphoprotein | 0 | 20 | 4.16E-13 |

The antigenic peptides identified as bound by the TCRs provided herein and having utility in identifying these TCRs by, e.g., a binding assay, may be derived from one or more of the following SARS-CoV-2 ORFs:

| SARS-COV-2 ORF | Peptide | SEQ ID NO |
|---|---|---|
| ORF1ab | HTTDPSFLGRY | 200 |
| surface glycoprotein | YLQPRTFLL | 201 |
| surface glycoprotein | APHGVVFL | 202 |
| membrane glycoprotein | YANRNRFLY | 203 |
| nucleocapsid phosphoprotein | SPRWYFYYL | 204 |
| nucleocapsid phosphoprotein | QELIRQGTDY | 205 |
| ORF3a | YFTSDYYQLY | 206 |

Therapeutic Methods

Also provided by the present disclosure are therapeutic methods. According to some embodiments, provided are methods comprising administering a COVID-19 therapy to a subject identified as comprising T cells that express a T cell receptor β chain (TCRβ) comprising a TCRβ CDR3 sequence set forth in SEQ ID Nos: 1-199. In certain embodiments, the methods comprise administering a COVID-19 therapy to a subject identified as comprising T cells that express two or more (e.g., two or more unique) TCRβ comprising a TCRβ CDR3 sequence set forth in SEQ ID Nos: 1-199.

As used herein, the terms "treatment," "treating," and the like, refer to obtaining a desired pharmacologic and/or physiologic effect. The effect may be therapeutic in terms of a partial or complete cure for a disease and/or adverse effect attributable to the disease. "Treatment," as used herein, covers any treatment of a disease in a mammal, including in a human, and includes: (a) inhibiting the disease, i.e., arresting its development; and (b) relieving the disease, i.e., causing regression of the disease.

A "therapeutically effective amount" or "efficacious amount" refers to the amount of a therapeutic agent that, when administered to a mammal or other subject for treating a disease, is sufficient to affect such treatment for the disease. The "therapeutically effective amount" will vary depending on the therapeutic agent, the disease and its severity and the age, weight, etc., of the subject to be treated.

Methods for treating a subject diagnosed as having COVID-19 may involve administering Remdesivir, protease inhibitors, anti-SARS-CoV-2 antibodies (e.g., monoclonal antibodies), and/or the like.

In some embodiments, the COVID-19 therapy is an adoptive cell therapy. Non-limiting examples of adoptive cell therapies include those involving administering to the subject an effective amount of recombinant cells (e.g., recombinant immune cells such as T cells) that express a T cell receptor comprising the COVID-19-associated TCRβ CDR3 sequence identified as being present in TCRs expressed by T cells in the subject or another COVID-19-associated CDR3 that is not detectably expressed by the subject. Similar to CAR therapies, TCR therapies modify the patient's T lymphocytes ex vivo before being administered back into the patient's body. The target antigens identified by CAR-T cell therapy are all cell surface proteins, while TCR-T cell therapy can recognize intracellular antigen fragments presented by MHC molecules, so TCR-T cell therapy has a wider range of targets. Approaches for TCR therapy are known and described in, e.g., Zhang et al. (2019) *Technol Cancer Res Treat.* 18:1533033819831068; Govers et al. (2010) Trends in Molecular Medicine 16 (2): 77-87; Zhao et al. (2019) Front. Immunol. 10:2250.

Nucleic acids that encode a T cell receptor β chain comprising a TCRβ CDR3 sequence set forth in SEQ ID Nos: 1-199 are also provided. For example, in certain embodiments, provided is an expression vector comprising a nucleic acid sequence that encodes a T cell receptor β chain comprising a TCRβ CDR3 sequence set forth in SEQ ID Nos: 1-199 operably linked to a nucleic acid expression control sequence. A "vector" is capable of transferring nucleic acid sequences to target cells (e.g., viral vectors, non-viral vectors, particulate carriers, and liposomes). Typically, "vector construct," "expression vector," and "gene transfer vector," mean any nucleic acid construct capable of directing the expression of a nucleic acid of interest and which can transfer nucleic acid sequences to target cells. Thus, the term includes cloning and expression vehicles, as well as viral vectors.

In order to express a desired T cell receptor β chain comprising a TCRβ CDR3 sequence set forth in SEQ ID Nos: 1-199, a nucleotide sequence encoding the T cell receptor β chain can be inserted into an appropriate vector, e.g., using recombinant DNA techniques known in the art. Exemplary viral vectors include, without limitation, retrovirus (including lentivirus), adenovirus, adeno-associated virus, herpesvirus (e.g., herpes simplex virus), poxvirus, papillomavirus, and papovavirus (e.g., SV40). Illustrative examples of expression vectors include, but are not limited to pClneo vectors (Promega) for expression in mammalian cells; pLenti4/V 5-DEST™, pLenti6/V 5-DEST™, murine stem cell virus (MSCV), MSGV, moloney murine leukemia virus (MMLV), and pLenti6.2/V5-GW/lacZ (Invitrogen) for lentivirus-mediated gene transfer and expression in mammalian cells. In certain embodiments, a nucleic acid sequence encoding the T cell receptor β chain may be ligated into any such expression vectors for the expression of the T cell receptor β chain in mammalian cells.

Expression control sequences, control elements, or regulatory sequences present in an expression vector are those non-translated regions of the vector-origin of replication, selection cassettes, promoters, enhancers, translation initiation signals (Shine Dalgarno sequence or Kozak sequence), introns, a polyadenylation sequence, 5' and 3' untranslated regions, and/or the like-which interact with host cellular proteins to carry out transcription and translation. Such elements may vary in their strength and specificity. Depending on the vector system and host utilized, any number of suitable transcription and translation elements, including ubiquitous promoters and inducible promoters may be used.

Components of the expression vector are operably linked such that they are in a relationship permitting them to function in their intended manner. In some embodiments, the term refers to a functional linkage between a nucleic acid expression control sequence (such as a promoter, and/or enhancer) and a second polynucleotide sequence, e.g., a nucleic acid encoding the T cell receptor β chain, where the expression control sequence directs transcription of the nucleic acid encoding the T cell receptor β chain.

In some embodiments, the expression vector is an episomal vector or a vector that is maintained extrachromosomally. As used herein, the term "episomal" refers to a vector that is able to replicate without integration into the host cell's chromosomal DNA and without gradual loss from a dividing host cell also meaning that said vector replicates extrachromosomally or episomally. Such a vector may be engineered to harbor the sequence coding for the origin of DNA replication or "ori" from an alpha, beta, or gamma herpesvirus, an adenovirus, SV40, a bovine papilloma virus, a yeast, or the like. The host cell may include a viral replication transactivator protein that activates the replication. Alpha herpes viruses have a relatively short reproductive cycle, variable host range, efficiently destroy infected cells and establish latent infections primarily in sensory ganglia. Illustrative examples of alpha herpes viruses include HSV 1, HSV 2, and VZV. Beta herpesviruses have long reproductive cycles and a restricted host range. Infected cells often enlarge. Non-limiting examples of beta herpes viruses include CMV, HHV-6 and HHV-7. Gamma-herpesviruses are specific for either T or B lymphocytes, and latency is often demonstrated in lymphoid tissue. Illustrative examples of gamma herpes viruses include EBV and HHV-8.

Also provided are recombinant cells that comprise any of the expression vectors of the present disclosure comprising a nucleic acid that encodes a T cell receptor β chain comprising a TCRβ CDR3 sequence set forth in SEQ ID Nos: 1-199. In certain aspects, provided are cells that express a TCR comprising a T cell receptor β chain comprising a TCRβ CDR3 sequence set forth in SEQ ID Nos: 1-199 on the surface of the cell.

In some embodiments, the cells of the present disclosure are eukaryotic cells. Eukaryotic cells of interest include, but are not limited to, yeast cells, insect cells, mammalian cells, and the like. Mammalian cells of interest include, e.g., murine cells, non-human primate cells, human cells, and the like.

"Recombinant host cells," "host cells," "cells," "cell lines," "cell cultures," and other such terms denoting microorganisms or higher eukaryotic cell lines, refer to cells which can be, or have been, used as recipients for a recombinant vector or other transferred DNA, and include the progeny of the cell which has been transfected. Host cells may be cultured as unicellular or multicellular entities (e.g., tissue, organs, or organoids) including an expression vector of the present disclosure.

In one aspect, the cells provided herein include immune cells. Non-limiting examples of recombinant immune cells which may include any of the expression vectors of the present disclosure include T cells, B cells, natural killer (NK) cells, macrophages, monocytes, neutrophils, dendritic cells, mast cells, basophils, and eosinophils. In some embodiments, the immune cell is a T cell. Examples of T cells include naive T cells ($T_N$), cytotoxic T cells ($T_{CTL}$), memory T cells ($T_{MEM}$), T memory stem cells ($T_{SCM}$), central memory T cells ($T_{CM}$), effector memory T cells ($T_{EM}$), tissue resident memory T cells ($T_{RM}$), effector T cells ($T_{EFF}$), regulatory T cells ($T_{REGs}$), helper T cells ($T_H$, $T_H1$, $T_H2$, $T_H17$) CD4+ T cells, CD8+ T cells, virus-specific T cells, alpha beta T cells ($T_{\alpha\beta}$), and gamma delta T cells ($T_{\gamma\delta}$). In another aspect, the cells provided herein comprise stem cells, e.g., an embryonic stem cell or an adult stem cell.

Also provided are methods of making the cells of the present disclosure. In some embodiments, such methods include transfecting or transducing cells with a nucleic acid or expression vector of the present disclosure, e.g., an expression vector comprising a nucleic acid that encodes a T cell receptor β chain comprising a TCRβ CDR3 sequence set forth in SEQ ID Nos: 1-199. The term "transfection" or "transduction" is used to refer to the introduction of foreign DNA into a cell. A cell has been "transfected" when exogenous DNA has been introduced inside the cell membrane. A number of transfection techniques are generally known in the art. See, e.g., Sambrook et al. (2001) Molecular Cloning, a laboratory manual, 3rd edition, Cold Spring Harbor Laboratories, New York, Davis et al. (1995) Basic Methods in Molecular Biology, 2nd edition, McGraw-Hill, and Chu et al. (1981) Gene 13:197. Such techniques can be used to introduce one or more exogenous DNA moieties into suitable host cells. The term refers to both stable and transient uptake of the genetic material.

In some embodiments, a cell of the present disclosure is produced by transfecting the cell with a viral vector encoding the T cell receptor β chain comprising a TCRβ CDR3 sequence set forth in SEQ ID Nos: 1-199. In some embodiments, such methods include activating a population of T cells (e.g., T cells obtained from an individual to whom a TCR T cell therapy will be administered), stimulating the population of T cells to proliferate, and transducing the T cell with a viral vector encoding the T cell receptor β chain comprising a TCRβ CDR3 sequence set forth in SEQ ID Nos: 1-199. In some embodiments, the T cells are transduced with a retroviral vector, e.g., a gamma retroviral vector or a lentiviral vector, encoding the T cell receptor β chain comprising a TCRβ CDR3 sequence set forth in SEQ ID Nos: 1-199. In some embodiments, the T cells are transduced with a lentiviral vector encoding the T cell receptor β chain comprising a TCRβ CDR3 sequence set forth in SEQ ID Nos: 1-199.

Cells of the present disclosure may be autologous/autogeneic ("self") or non-autologous ("non-self," e.g., allogeneic, syngeneic or xenogeneic). "Autologous" as used herein, refers to cells from the same individual. "Allogeneic" as used herein refers to cells of the same species that differ genetically from the cell in comparison. "Syngeneic," as used herein, refers to cells of a different individual that are genetically identical to the cell in comparison. In some embodiments, the cells are T cells obtained from a mammal. In some embodiments, the mammal is a primate. In some embodiments, the primate is a human.

T cells may be obtained from a number of sources including, but not limited to, peripheral blood, peripheral blood mononuclear cells, bone marrow, lymph node tissue, cord blood, thymus tissue, tissue from a site of infection, ascites, pleural effusion, spleen tissue, and tumors. In certain embodiments, T cells can be obtained from a unit of blood collected from an individual using any number of known techniques such as sedimentation, e.g., FICOLL™ separation.

In some embodiments, an isolated or purified population of T cells is used. In some embodiments, $T_{CTL}$ and $T_H$ lymphocytes are purified from PBMCs. In some embodiments, the $T_{CTL}$ and $T_H$ lymphocytes are sorted into naïve ($T_N$), memory ($T_{MEM}$), and effector ($T_{EFF}$) T cell subpopulations either before or after activation, expansion, and/or genetic modification. Suitable approaches for such sorting are known and include, e.g., magnetic-activated cell sorting (MACS), where $T_N$ are CD45RA$^+$ CD62L$^+$ CD95$^-$; $T_{SCM}$ are CD45RA$^+$ CD62L$^+$ CD95$^+$; $T_{CM}$ are CD45RO$^+$ CD62L$^+$ CD95$^+$; and TEM are CD45RO$^+$ CD62L$^-$ CD95$^+$. An example approach for such sorting is described in Wang et al. (2016) *Blood* 127 (24): 2980-90.

A specific subpopulation of T cells expressing one or more of the following markers: CD3, CD4, CD8, CD28, CD45RA, CD45RO, CD62, CD127, and HLA-DR can be further isolated by positive or negative selection techniques. In some embodiments, a specific subpopulation of T cells, expressing one or more of the markers selected from the group consisting of CD62L, CCR7, CD28, CD27, CD122, CD127, CD197; or CD38 or CD62L, CD127, CD197, and CD38, is further isolated by positive or negative selection techniques. In some embodiments, the manufactured T cell compositions do not express one or more of the following markers: CD57, CD244, CD 160, PD-1, CTLA4, TIM3, and LAG3. In some embodiments, the manufactured T cell compositions do not substantially express one or more of the following markers: CD57, CD244, CD 160, PD-1, CTLA4, TIM3, and LAG3.

In order to achieve therapeutically effective doses of T cell compositions, the T cells may be subjected to one or more rounds of stimulation, activation and/or expansion. T cells can be activated and expanded generally using methods as described, for example, in U.S. Pat. Nos. 6,352,694; 6,534,055; 6,905,680; 6,692,964; 5,858,358; 6,887,466; 6,905,681; 7,144,575; 7,067,318; 7,172,869; 7,232,566; 7,175,843; 5,883,223; 6,905,874; 6,797,514; and 6,867,041, each of which is incorporated herein by reference in its entirety for all purposes. In some embodiments, T cells are activated and expanded for about 1 to 21 days, e.g., about 5 to 21 days. In some embodiments, T cells are activated and expanded for about 1 day to about 4 days, about 1 day to about 3 days, about 1 day to about 2 days, about 2 days to about 3 days, about 2 days to about 4 days, about 3 days to about 4 days, or about 1 day, about 2 days, about 3 days, or about 4 days prior to introduction of a nucleic acid (e.g., expression vector) encoding the polypeptide into the T cells.

In some embodiments, T cells are activated and expanded for about 6 hours, about 12 hours, about 18 hours or about 24 hours prior to introduction of a nucleic acid (e.g., expression vector) encoding the T cell receptor β chain comprising a TCRβ CDR3 sequence set forth in SEQ ID Nos: 1-199 into the T cells. In some embodiments, T cells are activated at the same time that a nucleic acid (e.g., an expression vector) encoding the T cell receptor β chain is introduced into the T cells.

In some embodiments, conditions appropriate for T cell culture include an appropriate media (e.g., Minimal Essential Media or RPMI Media 1640 or, X-vivo 15, (Lonza)) and one or more factors necessary for proliferation and viability including, but not limited to serum (e.g., fetal bovine or human serum), interleukin-2 (IL-2), insulin, IFN-γ, IL-4, IL-7, IL-21, GM-CSF, IL-10, IL-12, IL-15, TGFβ, and TNF-α or any other additives suitable for the growth of cells known to the skilled artisan. Further illustrative examples of cell culture media include, but are not limited to RPMI 1640, Clicks, AEVI-V, DMEM, MEM, a-MEM, F-12, X-Vivo 15, and X-Vivo 20, Optimizer, with added amino acids, sodium pyruvate, and vitamins, either serum-free or supplemented with an appropriate amount of serum (or plasma) or a defined set of hormones, and/or an amount of cytokine(s) sufficient for the growth and expansion of T cells.

In some embodiments, the nucleic acid (e.g., an expression vector) encoding the T cell receptor β chain is introduced into the cell (e.g., a T cell) by microinjection, transfection, lipofection, heat-shock, electroporation, transduction, gene gun, microinjection, DEAE-dextran-mediated transfer, and the like. In some embodiments, the nucleic acid (e.g., expression vector) encoding the T cell receptor β chain is introduced into the cell (e.g., a T cell) by AAV transduction. The AAV vector may comprise ITRs from AAV2, and a serotype from any one of AAV1, AAV2, AAV3, AAV4, AAV5, AAV6, AAV7, AAV8, AAV9, or AAV 10. In some embodiments, the AAV vector comprises ITRs from AAV2 and a serotype from AAV6. In some embodiments, the nucleic acid (e.g., expression vector) encoding the T cell receptor β chain is introduced into the cell (e.g., a T cell) by lentiviral transduction. The lentiviral vector backbone may be derived from HIV-1, HIV-2, visna-maedi virus (VMV) virus, caprine arthritis-encephalitis virus (CAEV), equine infectious anemia virus (EIAV), feline immunodeficiency virus (FIV), bovine immune deficiency virus (BIV), or simian immunodeficiency virus (SIV). The lentiviral vector may be integration competent or an integrase deficient lentiviral vector (TDLV). In one embodiment, IDLV vectors including an HIV-based vector backbone (i.e., HIV cis-acting sequence elements) are employed.

In certain embodiments, a method for assessing efficacy of a candidate vaccine for preventing and/or treating SARS-CoV-2 infection is provided. In certain embodiments, the method comprises assessing a biological sample comprising T cells from a subject administered the candidate vaccine for presence of a T cell comprising a TCRβ CDR3 amino acid sequence set forth in any one of SEQ ID NOs: 1-199, wherein the presence of the TCR indicates that the candidate vaccine is effective in inducing an immune response to SARS-CoV-2. In certain aspects, presence of one or more or all of the TCRβ CDR3 amino acid sequences of Table 1 may be assessed.

Compositions and Uses Thereof

Provided herein are compositions comprising engineered T cells that are genetically modified to express a TCR comprising a CDR3 having an amino acid sequence of SEQ ID NO: 1-199. The TCR may additionally include the V and J gene segments associated with the CDR3, as listed in Table 1. Such recombinant T cells find use in treating COVID-19 and/or preventing developing COVID-19. Treatment methods may comprise administering a plurality of engineered T cells, where the T cells comprise a first T cell engineered to express a TCR comprising a first CDR3 sequence set forth in Table 1 and a second T cell engineered to express a TCR comprising a second CDR3 sequence set forth in Table 1, and so forth.

Compositions comprising a SARS-CoV-2 peptide antigen are also provided. In certain embodiments, the composition comprises:

a SARS-CoV-2 peptide antigen, wherein the peptide antigen comprises, consists essentially of, or consists of the amino acid sequence:

HTTDPSFLGRY; (SEQ ID NO: 200)

YLQPRTFLL; (SEQ ID NO: 201)

APHGVVFL; (SEQ ID NO: 202)

YANRNRFLY; (SEQ ID NO: 203)

SPRWYFYYL; (SEQ ID NO: 204)

QELIRQGTDY; or (SEQ ID NO: 205)

YFTSDYYQLY. (SEQ ID NO: 206)

The composition may comprise two or more of these peptide antigens. The peptide antigen may be up to 30 amino acids in length, optionally up to 25 amino acids in length, up to 20 amino acids in length, up to 15 amino acids in length, or up to 10 amino acids in length.

pMHC Multimers

Provided herein are peptide MHC (pMHC) multimers comprising two or more monomers, wherein the monomers comprise an MHC complexed with a SARS-CoV-2 peptide antigen comprising, consisting essentially of, or consisting of the amino acid sequence:

HTTDPSFLGRY; (SEQ ID NO: 200)

YLQPRTFLL; (SEQ ID NO: 201)

APHGVVFL; (SEQ ID NO: 202)

YANRNRFLY; (SEQ ID NO: 203)

SPRWYFYYL; (SEQ ID NO: 204)

QELIRQGTDY; or (SEQ ID NO: 205)

YFTSDYYQLY. (SEQ ID NO: 206)

The MHC of the pMHC monomers of the multimers may be A*01:01, A*02:01, B*07:02; or B*44:02.

In certain embodiments, the pMHC multimer comprises a plurality of pMHC monomers, each monomer comprising a SARS-CoV-2 peptide antigen comprising, consisting essentially of, or consisting of the amino acid sequence: HTTDPSFLGRY (SEQ ID NO:200), YANRNRFLY (SEQ ID NO:203), or YFTSDYYQLY (SEQ ID NO:206); and the MHC A*01:01.

In certain embodiments, the pMHC multimer comprises a plurality of pMHC monomers, each monomer comprising a SARS-CoV-2 peptide antigen comprising, consisting essentially of, or consisting of the amino acid sequence YLQPRTFLL (SEQ ID NO:201); and the MHC A*02:01.

In certain embodiments, the pMHC multimer comprises a plurality of pMHC monomers, each monomer comprising a SARS-CoV-2 peptide antigen comprising, consisting essentially of, or consisting of the amino acid sequence APHGVVFL (SEQ ID NO:202) or SPRWYFYYL (SEQ ID NO:204); and the MHC B*07:02.

In certain embodiments, the pMHC multimer comprises a plurality of pMHC monomers, each monomer comprising a SARS-CoV-2 peptide antigen comprising, consisting essentially of, or consisting of the amino acid sequence QELIRQGTDY (SEQ ID NO:205); and the MHC B*44:02.

In some embodiments, the plurality of monomers comprise 2 to 100 monomers, e.g., 2 to 100, 2 to 75, 2 to 50, 2 to 40, 2 to 30, 2 to 20, 2 to 15, or 2 to 10, e.g., 10, 9, 8, 7, 6 (hexamers), 5 (pentamers), or 4 (tetramers). According to some embodiments, the multimers are tetramers. In certain embodiments, the multimers are tetramers or pentamers.

The pMHC may be adapted to be disposed upon a substrate. In some embodiments, the pMHC is disposed upon a substrate.

According to the methods of the present disclosure, multimers of the pMHC disclosed herein are disposed on the substrate and used to interrogate a biological sample for TCRs. As used herein, a "multimer" is two or more of the same type of pMHC stably associated with one another. By "stably associated" is meant a physical association between two entities in which the mean half-life of association is one day or more in PBS at 4° C. In certain aspects, the physical association between the two entities has a mean half-life of one day or more, one week or more, one month or more, including six months or more, e.g., 1 year or more, in PBS at 4° C. According to certain embodiments, the stable association arises from a covalent bond between the two entities, a non-covalent bond between the two entities (e.g., an ionic or metallic bond), or other forms of chemical attraction, such as hydrogen bonding, Van der Waals forces, and/or the like.

A variety of approaches are available to multimerize pMHC. In certain embodiments, the multimers are stably associated via non-covalent interactions. For example, the monomers may be biotin-labeled, and multimerization is achieved using streptavidin or a streptavidin-labeled molecule to which multiple biotin-labeled monomers stably associate. In one non-limiting example, a dextran-backbone conjugated with streptavidin (e.g., Streptavidin-Dextramer® (Immudex)) is employed to multimerize two or more (e.g., 4 or more, 5 or more, 10 or more, etc.) biotin-labeled pMHC monomers.

The term "major histocompatibility complex" or "MHC" as used herein means a protein complex comprising two non-covalently associated chains, an alpha chain and a beta chain, encoded by a cluster of genes that plays a role in control of the cellular interactions responsible for physiologic immune responses. In humans, the MHC complex is also known as the human leukocyte antigen (HLA) complex. The term "MHC" encompasses both class I MHCs (comprising a heavy (alpha) chain and a light (beta or beta microglobulin) chain and class II MHC (comprising alpha and beta chains) complexes. As used herein, "peptide MHC" or "pMHC" refers to an MHC molecule and an antigenic peptide complexed in such a manner that the pMHC complex can be specifically bound by a T cell receptor.

The methods of the present disclosure comprise assessing the substrate for T cell receptor-multimer complexes. The presence of T cell receptor-multimer complexes may be determined qualitatively or quantitatively. Qualitative determination includes determinations in which a simple yes/no result with respect to the presence of T cell receptor-multimer complexes is provided to a user. Quantitative determination includes both semi-quantitative determinations in which a rough scale result, e.g., low, medium, high, is provided to a user regarding the amount of T cell receptor-multimer complexes and fine scale results in which a precise measurement of T cell receptor-multimer complexes is provided to the user.

The methods of the present disclosure enable assessment of a biological sample for the presence of TCRs that specifically bind a pMHC provided herein.

The methods of the present disclosure may further comprise identifying the individual as having COVID-19 when the assessment of the biological sample indicates the presence of TCRs that specifically bind the pMHC disclosed herein. The identifying may be based upon a qualitative or quantitative assessment of the presence or prevalence/amount of immune cell receptor-multimer complexes on the substrate. When an individual is identified by the present methods as having COVID-19, in some instances, the methods further comprise treating COVID-19 in the individual. Accordingly, in some embodiments, provided are methods comprising treating an individual COVID-19 identified by any of the methods of the present disclosure.

Suitable approaches for producing the peptide and MHC components of pMHC monomers, for loading the MHC with the peptide to produce pMHC monomers, and for multimerizing the monomers (e.g., to produce, tetramers, pentamers, dextramers, etc. from the pMHC monomers) are known.

Also provided are substrates having disposed thereon any of the pMHC multimers described herein.

Computer-Readable Media and Systems

Also provided by the present disclosure are computer-readable media and systems.

In certain aspects, provided are one or more computer-readable media having stored thereon one or more TCRβ CDR3 sequences set forth in SEQ ID Nos: 1-199. The number of TCRβ CDR3 sequences set forth in SEQ ID Nos: 1-199 stored on the one or more computer-readable media may vary. For example, the one or more computer-readable media may have stored thereon 1 or more, 2 or more, 3 or more, 4 or more, 5 or more, 6 or more, 7 or more, 8 or more, 9 or more, 10 or more, 15 or more, 20 or more, 25 or more, 30 or more, 35 or more, 40 or more, 45 or more, 50 or more, 75 or more, 100 or more, 150 or more or more of each of the TCRβ CDR3 sequences set forth in SEQ ID Nos: 1-199. When fewer than all of the TCRβ CDR3 sequences set forth in SEQ ID Nos: 1-199 are stored on the one or more computer-readable media, the one or more computer-readable media may have stored thereon any desired number (e.g., as set forth above) and combination of TCRβ CDR3 sequences set forth in SEQ ID Nos: 1-199. In some embodiments, the one or more computer-readable media may have stored thereon 190 or fewer, 180 or fewer, 170 or fewer, 160 or fewer, 150 or fewer, 140 or fewer, 130 or fewer, 120 or fewer, 110 or fewer, 100 or fewer, 90 or fewer, 80 or fewer, 70 or fewer, 60 or fewer, 50 or fewer, 40 or fewer, 30 or fewer, 20 or fewer, or 10 or fewer of the TCRβ CDR3 sequences set forth in SEQ ID Nos: 1-199, in any desired combination.

Also provided are systems for assessing TCRβ CDR3 sequences. According to some embodiments, provided are systems for assessing TCRβ CDR3 sequences, such systems comprising one or more processors and one or more computer-readable media. The one or more computer-readable media comprise instructions stored thereon, which when executed by the one or more processors, cause the one or more processors to assess TCRβ CDR3 sequences determined from a sample obtained from a subject having or suspected of having COVID-19 for the presence or absence of one or more TCRβ CDR3 sequences set forth in SEQ ID Nos: 1-199. According to some embodiments, the number of TCRβ CDR3 sequences determined from the sample obtained from the subject is from 1,000 to 2,000,000. For example, in certain embodiments, the number of determined TCRβ CDR3 sequences is 2,000,000 or fewer (e.g., 1,500,000 or fewer, 1,250,000 or fewer, 1,000,000 or fewer, 750,000 or fewer, or 500,000 or fewer), but 1,000 or more, 5,000 or more, 10,000 or more, 15,000 or more, 20,000 or more, 25,000 or more, 30,000 or more, 35,000 or more, 40,000 or more, 45,000 or more, 50,000 or more, 55,000 or more, 60,000 or more, 65,000 or more, 70,000 or more, 75,000 or more, 80,000 or more, 85,000 or more, 90,000 or more, 95,000 or more, or 100,000 or more. The number of TCRβ CDR3 sequences set forth in SEQ ID Nos: 1-199 to which the determined TCRβ CDR3 sequences is compared may vary. For example, the determined TCRβ CDR3 sequences may be compared to 1 or more, 2 or more, 3 or more, 4 or more, 5 or more, 6 or more, 7 or more, 8 or more, 9 or more, 10 or more, 15 or more, 20 or more, 25 or more, 30 or more, 35 or more, 40 or more, 45 or more, 50 or more, 75 or more, 100 or more, 150 or more, 200 or more, or 250 or more of each of the TCRβ CDR3 sequences set forth in SEQ ID Nos: 1-199. When the determined TCRβ CDR3 sequences are compared to fewer than all of the TCRβ CDR3 sequences set forth in SEQ ID Nos: 1-199, the determined TCRβ CDR3 sequences may be compared to any desired number (e.g., as set forth above) and combination of TCRβ CDR3 sequences set forth in SEQ ID Nos: 1-199.

The one or more computer-readable media may further comprise instructions stored thereon, which when executed by the one or more processors, cause the one or more processors to perform one or more additional steps based on the results of the assessing step. For example, if it is determined from the assessing step that none of the TCRβ CDR3 sequences set forth in SEQ ID Nos: 1-199 are present in the TCRβ CDR3 sequences determined from the sample obtained from the subject having or suspected of having COVID-19, then the instructions may further cause the one or more processors to, e.g., identify the subject as not having COVID-19 and identify the subject as one who should not be administered a COVID-19 therapy. Also, by way of example, if it is determined from the assessing step that one or more (e.g., 2 or more, 3 or more, 4 or more, 5 or more, or 10 or more) of the TCRβ CDR3 sequences set forth in SEQ ID Nos: 1-199 are present in the TCRβ CDR3 sequences determined from the sample obtained from the subject having, suspected of having, or having had COVID-19, then the instructions may further cause the one or more processors to, e.g., identify the subject as having a present or previous SARS-CoV-2 infection, identify the subject as having COVID-19, and/or identify the subject as one who should be administered a COVID-19 therapy.

In certain embodiments, the one or more computer-readable media may further comprise instructions stored thereon, which when executed by the one or more processors, cause the one or more processors to subject the results of the assessing step to further analysis, such as subjecting the results of the assessing step to a model as disclosed in the methods section of this application.

A variety of processor-based systems may be employed to implement the embodiments of the present disclosure. Such systems may include system architecture wherein the components of the system are in electrical communication with each other using a bus. System architecture can include a processing unit (CPU or processor), as well as a cache, that are variously coupled to the system bus. The bus couples various system components including system memory, (e.g., read only memory (ROM) and random access memory (RAM), to the processor.

System architecture can include a cache of high-speed memory connected directly with, in close proximity to, or integrated as part of the processor. System architecture can copy data from the memory and/or the storage device to the cache for quick access by the processor. In this way, the cache can provide a performance boost that avoids processor delays while waiting for data. These and other modules can control or be configured to control the processor to perform various actions. Other system memory may be available for use as well. Memory can include multiple different types of memory with different performance characteristics. Processor can include any general purpose processor and a hardware module or software module, such as first, second and third modules stored in the storage device, configured to control the processor as well as a special-purpose processor where software instructions are incorporated into the actual processor design. The processor may essentially be a completely self-contained computing system, containing multiple cores or processors, a bus, memory controller, cache, etc. A multi-core processor may be symmetric or asymmetric.

To enable user interaction with the computing system architecture, an input device can represent any number of input mechanisms, such as a microphone for speech, a touch-sensitive screen for gesture or graphical input, keyboard, mouse, motion input, speech and so forth. An output device can also be one or more of a number of output mechanisms. In some instances, multimodal systems can enable a user to provide multiple types of input to communicate with the computing system architecture. A communications interface can generally govern and manage the user input and system output. There is no restriction on operating on any particular hardware arrangement and therefore the basic features here may easily be substituted for improved hardware or firmware arrangements as they are developed.

The storage device is typically a non-volatile memory and can be a hard disk or other types of computer-readable media which can store data that are accessible by a computer, such as magnetic cassettes, flash memory cards, solid state memory devices, digital versatile disks, cartridges, random access memories (RAMs), read only memory (ROM), and hybrids thereof.

The storage device can include software modules for controlling the processor. Other hardware or software modules are contemplated. The storage device can be connected to the system bus. In one aspect, a hardware module that performs a particular function can include the software component stored in a computer-readable medium in connection with the necessary hardware components, such as the processor, bus, output device, and so forth, to carry out various functions of the disclosed technology.

Embodiments within the scope of the present disclosure may also include tangible and/or non-transitory computer-readable storage media or devices for carrying or having computer-executable instructions or data structures stored thereon. Such tangible computer-readable storage devices can be any available device that can be accessed by a general purpose or special purpose computer, including the functional design of any special purpose processor as described above. By way of example, and not limitation, such tangible computer-readable devices can include RAM, ROM, EEPROM, CD-ROM or other optical disk storage, magnetic disk storage or other magnetic storage devices, or any other device which can be used to carry or store desired program code in the form of computer-executable instructions, data structures, or processor chip design. When information or instructions are provided via a network or another communications connection (either hardwired, wireless, or combination thereof) to a computer, the computer properly views the connection as a computer-readable medium. Thus, any such connection is properly termed a computer-readable medium. Combinations of the above should also be included within the scope of the computer-readable storage devices.

Computer-executable instructions include, for example, instructions and data which cause a general purpose computer, special purpose computer, or special purpose processing device to perform a certain function or group of functions. Computer-executable instructions also include program modules that are executed by computers in stand-alone or network environments. Generally, program modules include routines, programs, components, data structures, objects, and the functions inherent in the design of special-purpose processors, etc. that perform tasks or implement abstract data types. Computer-executable instructions, associated data structures, and program modules represent examples of the program code means for executing steps of the methods disclosed herein. The particular sequence of such executable instructions or associated data structures represents examples of corresponding acts for implementing the functions described in such steps.

Other embodiments of the disclosure may be practiced in network computing environments with many types of computer system configurations, including personal computers, hand-held devices, multi-processor systems, microprocessor-based or programmable consumer electronics, network PCs, minicomputers, mainframe computers, and the like. Embodiments may also be practiced in distributed computing environments where tasks are performed by local and remote processing devices that are linked (either by hardwired links, wireless links, or by a combination thereof) through a communications network. In a distributed computing environment, program modules may be located in both local and remote memory storage devices.

The following examples are offered by way of illustration and not by way of limitation.

EXPERIMENTAL

Example 1: A Large-Scale Database of T-Cell Receptor Beta (TCRb) Sequences and Binding Associations from Natural and Synthetic Exposure to SARS-CoV-2

Summary

The establishment and current content of the ImmuneCODE™ database, which includes hundreds of millions of T-Cell receptor sequences from over 1,400 subjects exposed to or infected with the COVID19 virus, as well as over 160,000+ high-confidence TCR-SARS-COV-2 peptide binding pairs is described. This database is made freely available, and the data contained in it can be downloaded and analyzed online or offline to assist with the global efforts to understand the immune response to the COVID-19 virus and develop new interventions.

Introduction

The emergence of SARS-CoV-2 in December of 2019 and the ensuing pandemic declared by the WHO at the end of January 2020 created an urgent need to understand the disease and its causative agent. Initial studies have shown a strong T-cell based adaptive immune response (Griffoni, A. et al. 2020; Weiskopf, D. et al. 2020; Sekine, T et al. 2020), but its detailed nature remains uncharacterized. Therefore, previously described immunoSEQ® (Robins H S, et al., 2009; Robins H S, et al., 2012; Carlson C S, et al., 2013) Assay and MIRA™ (Klinger, M. et al., 2013; Klinger, M. et al., 2015) tool were applied to deepen the understanding of the adaptive immune response to COVID-19 infection in support of SARS-CoV-2 research.

Partnership with Microsoft, Illumina, Labcorp/Covance, and health organizations across the world was established to generate the ImmuneCODE database described herein. These data are being made freely available to the scientific community so that any researcher, public health official or organization can utilize the data to accelerate ongoing global efforts to develop better diagnostics, vaccines and therapeutics, as well as to answer important questions about the virus.

Two approaches were used to generate the data included in this database. (A) The immunoSEQ dataset includes 1,414 deeply sampled TCRb repertoires from subjects who at the time of sampling either had been exposed to, were actively suffering from, or had recovered from COVID-19. These data originate from two sources: (1) ImmuneRACE (Immune Response Action to COVID-19 Events), an ongoing prospective study enrolling participants across the U.S. to decode how immune systems detect and respond to the virus, which includes self-reported demographic and clinical data, and (2) thousands of de-identified geographically and ethnically diverse patient blood samples collected by institutions around the world. These data include varying degrees of demographic and clinical information (as allowed by each partner and their corresponding IRB). (B) The MIRA dataset maps out where the TCRs are binding to the virus epitopes an includes data obtained from exposed subjects and naïve controls. In total, the MIRA dataset includes more than 160,000+ high-confidence binding pairs between TCRb sequences and fragments of the SARS-CoV-2 virus.

This database will continue to grow as participants are recruited to immuneRACE and add samples collected by additional institutions, resulting in more T-cell repertoires of exposed and infected individuals and binding pairs, and allowing the association of T-cell signatures with disease and outcomes. This freely available resource will inform our understanding of the immune response to the virus and that it will be useful for researchers around the world by accelerating their work in basic and applied immunology, thus contributing to the development of new therapeutic and preventive measures.

Results

Dataset Structure

The ImmuneCODE database includes both immunoSEQ and MIRA data, and is being shared through Adaptive's immuneACCESS® open data portal, which enables the export of complete or selected data, as well as real-time analysis using a rich suite of custom-built tools. Specifically, all data referenced herein can be found at clients.adaptivebiotech.com/pub/covid-2020 (DOI 10.21417/ADPT2020COVID). Note that the dataset will continue to grow over time; instructions for selecting only the subjects described in this article are included on the immuneACCESS site.

immunoSEQ Data

The ongoing immuneRACE study aims to enroll 1,000 subjects who have been exposed to, are currently infected with, or have recovered from COVID-19. The current release of the database includes T-cell repertoire data from the first 160 participants in the study; new data will be added as it is generated. This release also includes T-cell repertoire data from 1,254 subjects from 6 global collaborators; new T-cell repertoires may be generated both by adding new samples from these ongoing studies, and by incorporating additional institutions to this effort. These data were generated from participant samples using the TCRb immunoSEQ Assay as previously described. They include a list of unique TCRb rearrangements found in each analyzed sample, a count for each rearrangement, and sample-level metadata. Certain pre-configured analyses we believe will be most used will also be available through immuneACCESS so that users do not need to recreate them. The data can be exported using dedicated links on the immuneACCESS project page for offline analysis.

By default the immunoSEQ Analyzer includes many metadata fields that are useful across different research contexts such as the sample level fields and the sequence-level fields. The amount of metadata available varies by source and participant; we include all available, uncurated metadata for each sample in the "sample_tags" and "sample_rich_tags" fields. At a minimum, these include includes de-identified subject IDs COVID-19 status, age in years, and sex.

MIRA Data

Antigen-specific TCRs were identified using the 'Multiplex Identification of Antigen-Specific T-Cell Receptors Assay (MIRA). MIRA is a high-throughput multiplex assay, enabling the identification of antigen-specific TCR to large numbers of query antigens (hundreds to thousands at a time and in parallel) by combining immune assays with T-cell receptor sequencing. We use cell sorting based on the upregulation of activation markers to separate a population of antigen-specific T cells. This positive population is sequenced via immunoSEQ, and clonotypes specific to antigen are identified by virtue of enrichment in the positive population compared to a sample of unenriched or unsorted T cells.

With the goal of identifying SARS-CoV-2-specific TCRs, T-cell repertoires from both healthy donors and COVID-19 patients were interrogated. Input cell types used varied and included PBMCs from healthy donors or COVID-19 patients, and naïve T cells from healthy donors. To maximize TCR yield per experiment, T cells from both types of input cells outlined above were expanded. When starting with PBMCs from either healthy donors or COVID-19 patients, T cells were expanded polyclonally with soluble anti-CD3. When starting with naïve CD8 T cells from healthy donors, T cells were expanded following co-culture with monocyte-derived DCs loaded with a pool of all peptides derived from SARS-CoV-2.

Two different MIRA assay approaches, peptide- or transgene-based were used. Both enable the identification of antigen-specific TCRs, however the transgene-based approach enables identification of TCRs that are specific to epitopes encoded and presented by APCs following expression upon transfection of transgenes. This approach enables us to distinguish the subset of TCRs that respond to endogenously presented epitopes rather than those that only respond to exogenously loaded peptides. Binding or activation following a multimer stain or incubation with peptides is therefore not an indicator of whether a T cell is specific to an endogenously presented epitope. The underlying assumption for any immunological assay involving multimers or exogenously loaded peptides is that the epitope being tested is actually a presented epitope. For well-characterized epitopes this assumption is reasonable, however when querying large numbers of novel epitopes from a novel virus (SARS-CoV-2, for example) the risk for false positives, defined as TCRs specific to a never-before tested peptide that was exogenously loaded, is higher.

In total, the MIRA dataset includes more than 160,000+ high-confidence binding pairs between TCRb sequences and fragments of the SARS-CoV-2 virus. These data are made available as a set of downloadable files "ImmuneCODE-MIRA-Release002.1.zip", which can also be accessed through the immuneACCESS project page.

The dataset includes experiments from three MIRA panels. Two of these panels, named "minigene_Set1" and "minigene_Set2", targeted large protein sequences intended to narrow down which parts of the genome generally elicit immune response. The third panel, named "C19_cl", targeted individual peptides or small groups of peptides. Most of the MIRA data included in this dataset corresponds to the C19_cl panel.

Tables describe the MIRA data included in the database, as follows: subject-metadata.csv includes available metadata for each sample from subjects included in the MIRA experiments (both in the two minigene and in the peptide panels described above). HLA types are provided when available. Missing values are generally represented with "N/A", except for HLA types, where missing data is represented as an empty string. Note that the metadata contained in this file relates to the MIRA results, and is distinct from the immunoSEQ-related metadata (I.e. "tags" in the tables above). Table orfs.csv includes the genomic location of the MIRA targets as per GenBank. Table minigene-hits.csv contains counts of the number of unique TCRs that bound to targets within the "minigene_Set1" and "minigene_Set2" MIRA panels, while Table minigene-detail.csv describes the identity of the TCRs bound per target for both minigene MIRA panels. Finally, Table peptide-hits.csv contains counts of the number of unique TCRs that bound to targets within the "C19_cl" MIRA panel, while Table peptide-detail.csv describes the identity of the TCRs bound per target for the C19_cl MIRA panel.

Example 2: Diagnosis and Tracking of Past SARS-CoV-2 Infection in a Large Study of Vo', Italy Through T-Cell Receptor Sequencing Summary Measuring the adaptive immune response after SARS-CoV-2 infection may improve the understanding of COVID-19 exposure and potential future protection or immunity. T cell and antibody signatures in a large population study of over 2,200 individuals from the municipality of Vo', Italy, including 70 PCR-confirmed COVID cases (24 asymptomatic, 37 symptomatic, 9 hospitalized) were analyzed. Blood samples taken two months after PCR diagnosis demonstrated 97% (68/70) of subjects had a positive T-cell test result, significantly higher than an antibody serology assay (77%; 54/70 of subjects) performed on the same samples. The depth and breadth of the T-cell response was associated with disease severity, with symptomatic and hospitalized COVID cases having significantly higher response than asymptomatic cases. In contrast, antibody levels at this convalescent time point did not correlate with disease severity. Several dozen additional suspected infections were identified from the 2,220 subjects without confirmatory PCR tests, with a higher T-cell test positive rate observed in subjects who reported symptoms or had household exposure to an PCR-confirmed infection. Taken together, these results establish that T cells are a reliable and persistent measure of past SARS-CoV-2 infection.

Introduction

COVID-19 presents with a wide range in severity, ranging from asymptomatic infection to severe illness and death. To date, it is unknown whether, and for how long, prior infection with SARS-CoV-2 provides immunity against future re-infection, nor is it known how the severity of disease might influence long-term immunity. Direct, quantitative measures of the adaptive immune response to SARS-CoV-2 infection, particularly in longitudinal samples following recovery, may offer insights into immunity.

Following the first reported COVID-19 death in the municipality of Vo', Italy and subsequent lockdown of the entire municipality, a large study was undertaken to screen and follow the majority of the residents in that area (Lavezzo 2020). Two consecutive time points of PCR-based diagnostic tests for SARS-CoV-2 were performed on nearly 2,900 people, identifying 82 people who were positive for the virus. Two months later, blood samples were collected from the majority of study participants for quantitative assessment of both SARS-CoV-2 specific T cells and IgG antibody titers. As the initial burst of virus-specific effector T cells and secreted antibodies from plasmablasts are likely to have subsided two months post diagnosis, this convalescent time point is appropriate to assess longer term adaptive immune memory.

Methods

Clinical Cohort and Sample Collection

This report extends results for the Vo', Italy cohort initially described in Lavezzo 2020. Upon the detection of SARS-CoV-2 in a deceased resident of Vo' on 21-2-2020, an epidemiological study was conducted to investigate the prevalence of SARS-CoV-2 infection in the municipality.

Sampling for viral PCR testing was performed on the majority of the population immediately after the detection of the first cases (21-29-2-2020) and again at the end of a 2-week lockdown (7-3-2020). Follow-up blood samples were collected 56 days later in early May for antibody serology and T-cell testing.

In addition to biospecimen collection, clinical data was collected for each study participant including the results of SARS-CoV-2 testing, demographics, health records, and residence and contact network information. The definition of symptomatic used in this study is a participant who required hospitalization and/or reported fever (yes/no or a temperature above 37° C.) and/or cough and/or at least two of the following symptoms: sore throat, headache, diarrhoea, vomit, asthenia, muscle pain, joint pain, loss of taste or smell, or shortness of breath. Symptomatic subjects who reported hospitalization are split out separately as "hospitalized" in the disease severity analyses.

Antibody Testing

Antibody response was measured using a commercial serology test (LIAISON SARS-CoV-2 S1/S2 IgG test, DiaSorin, Italy).

Immunosequencing of TCR Repertoires

Genomic DNA was extracted from frozen, plasma-depleted blood samples using the Qiagen DNeasy® Blood Extraction Kit (Qiagen). As much as 18 mg of input DNA was then used to perform immunosequencing of the CDR3 regions of TCRb chains using the ImmunoSEQ Assay. Briefly, input DNA was amplified in a bias-controlled multiplex PCR, followed by high-throughput sequencing. Sequences were collapsed and filtered to identify and quantitate the absolute abundance of each unique TCRβ CDR3 region for further analysis as previously described (Robins 2009, Robins 2012, Carlson 2013). In order to quantify the proportion of T cells out of total nucleated cells input for sequencing, or T cell fraction, a panel of reference genes present in all nucleated cells was amplified simultaneously (Pruessmann 2020).

Characterization of the T-Cell Response

Classification of prior infection with SARS-CoV-2 as well as the clonal depth and breadth of T-cell response were calculated similar to the method in Snyder 2020. Briefly recapping the prior work, TCR repertoires from 784 unique cases of RT-PCR confirmed SARS-CoV-2 infection and 2,448 healthy controls collected before 2020 were compared by one-tailed Fisher's exact tests to identify 4,469 public TCRβ sequences ("enhanced sequences") significantly enriched in SARS-CoV-2 positive samples. (For clarity, all training data to identify the enhanced sequences for SARS-CoV-2 infection came from multiple other study cohorts and not the population being analyzed here.) The enhanced sequences were used to develop a classifier predicting current or past infection with SARS-CoV-2 using a simple two feature logistic regression with dependent variables E and N, where E is the number of unique TCRβ DNA sequences that encode an enhanced sequence and N is the total number of unique TCRβ DNA sequences in that subject. Application of this initial clinical classifier to this study demonstrated the high sensitivity (97%) reported above.

A method to improve specificity near the decision boundary of the logistic regression by filtering enhanced sequences that may be potential false positives has since been developed. Specifically, TCRs that are likely associated with CMV or HLA types (from response to other antigens, and thus not SARS-CoV-2 specific sequences) are identified by Fisher's Exact testing on TCR repertoires of ~2,000 healthy controls with available HLA genotyping and CMV serotyping data. From this list of ~1.8M sequences, the 182 sequences that overlapped with the SARS-CoV-2 enhanced sequences were removed, leaving 4,287 enhanced sequences. A two feature logistic regression based on this pruned list of enhanced sequences was used here to classify positive/negative calls for prior infection. The pruned list of enhanced sequences was also used to calculate the clonal depth and breadth using the same formulae as in Snyder 2020.

Results

T-cell receptor sequencing was performed on blood samples from 2,290 study subjects using ImmunoSEQ®. SARS-CoV-2 specific signals including an overall T-cell test call (positive/negative) and the clonal depth (relative proportion of T cells that are SARS-CoV-2 specific) and clonal breadth (fraction of all unique TCR DNA clones that are SARS-CoV-2 specific) of response were calculated as previously reported (Snyder 2020). Antibody response was measured at the same timepoint for these subjects using a commercial antibody serology test. Of the 2,290 subjects, 70 had a confirmed diagnosis of COVID-19 from a prior positive PCR test, and the rest were PCR negative at both surveys. Twenty-four of these 70 had been asymptomatic, 37 had symptoms but did not require hospitalization and 9 were hospitalized. Across subjects with confirmed infection, 97% (68 of 70) had detectable SARS-CoV-2 specific T cells and a positive T-cell test result, while only 77% (54 of 70) had a positive serology test result. Notably, the 23% of antibody negative convalescent subjects were distributed relatively evenly between asymptomatic and symptomatic subjects.

Figure 2A:
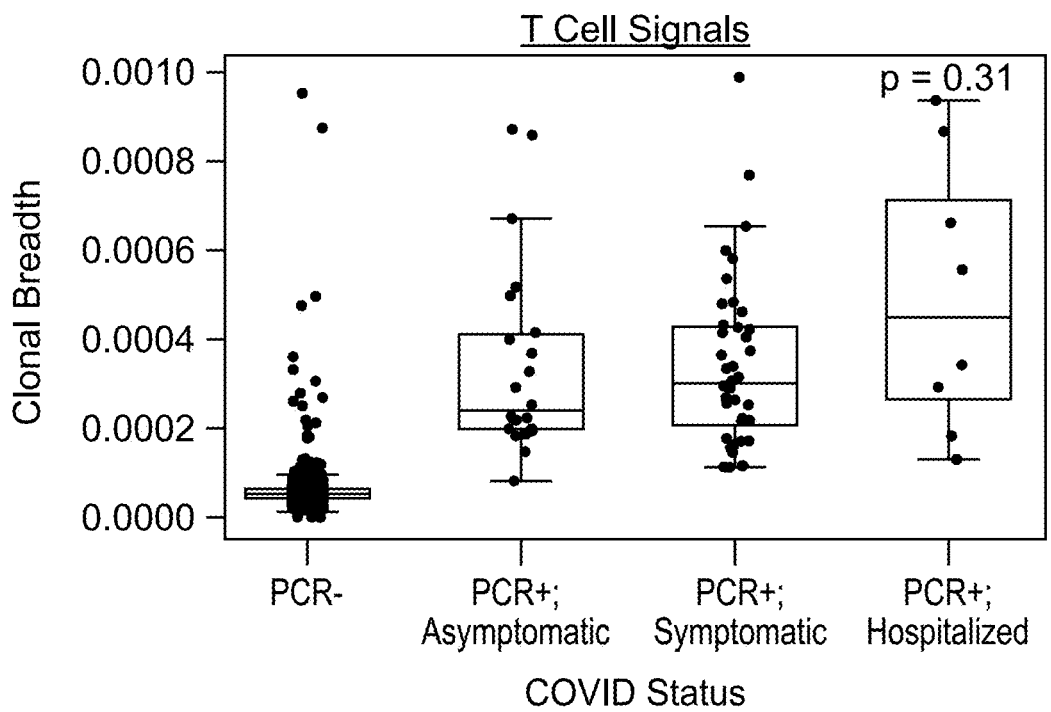
FIGS. 2A-2E. T-cell breadth (FIG. 2A), T-cell depth (FIG. 2B), and antibody levels (FIGS. 2C-2E) compared across 2154 PCR-subjects, and in 70 PCR+ subjects with results for all three serology tests faceted by disease severity. Clonal depth indicates the relative proportion of T cells that are SARS-CoV-2 specific and clonal breadth indicates the fraction of all unique TCR DNA clones that are SARS-CoV-2 specific. P values correspond to Jonckheere's two-sided trend test across the three PCR+ categories.
Figure 2B:
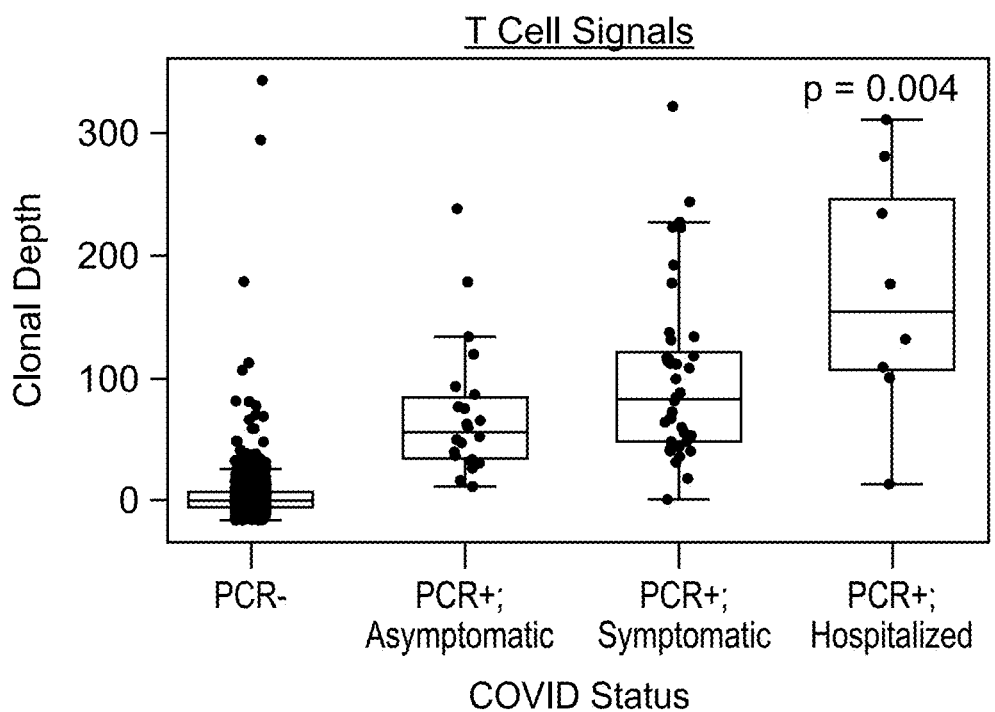
Figure 2C:
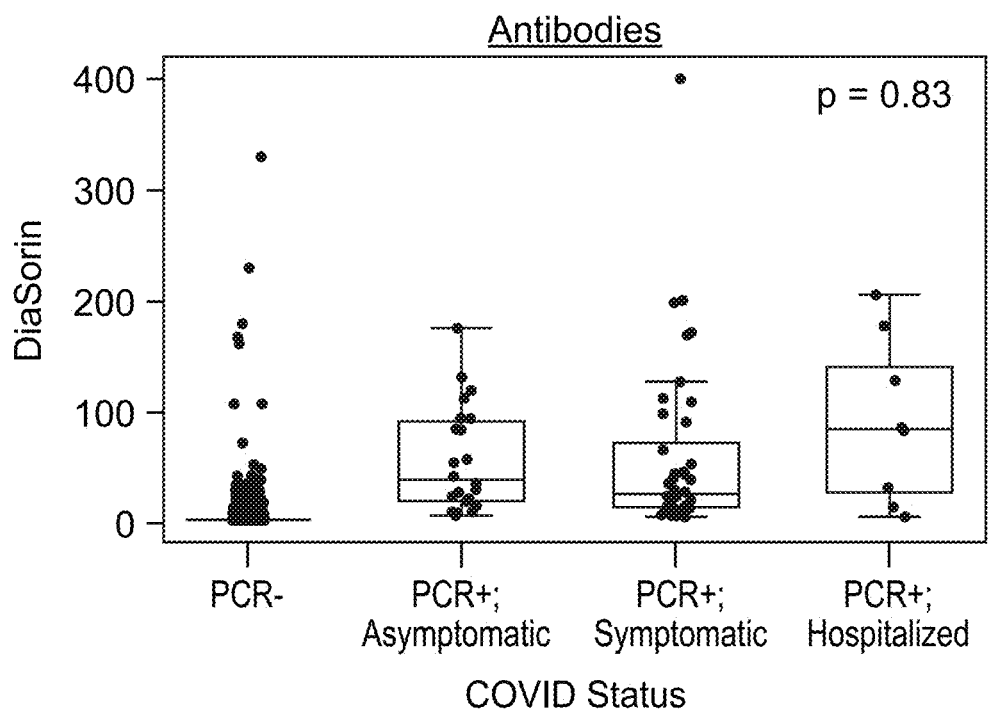
Figure 2D:
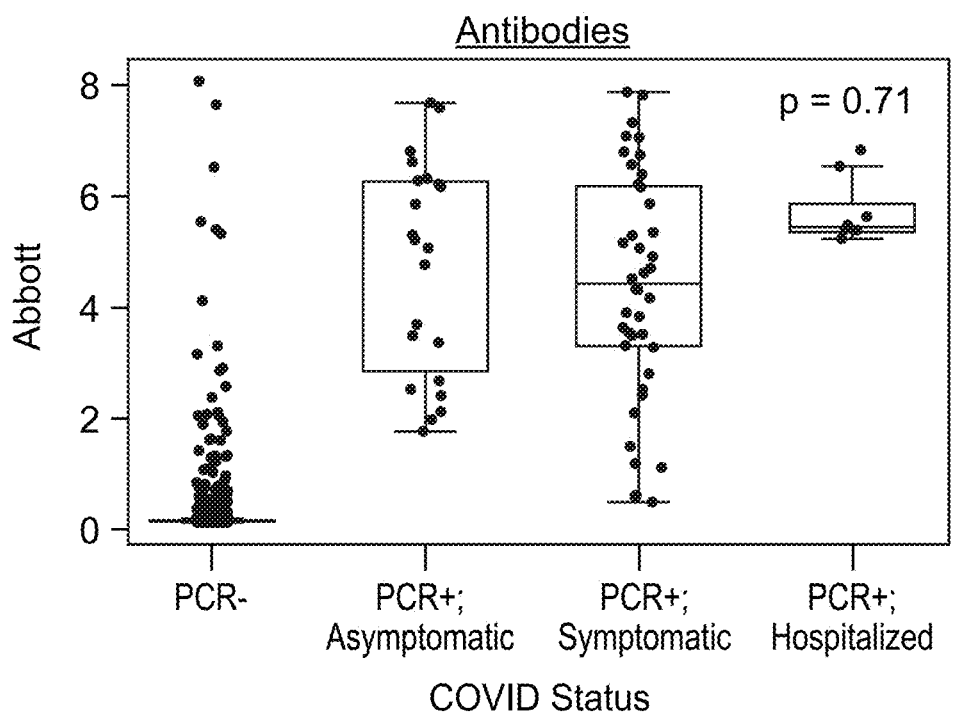
Figure 2E:
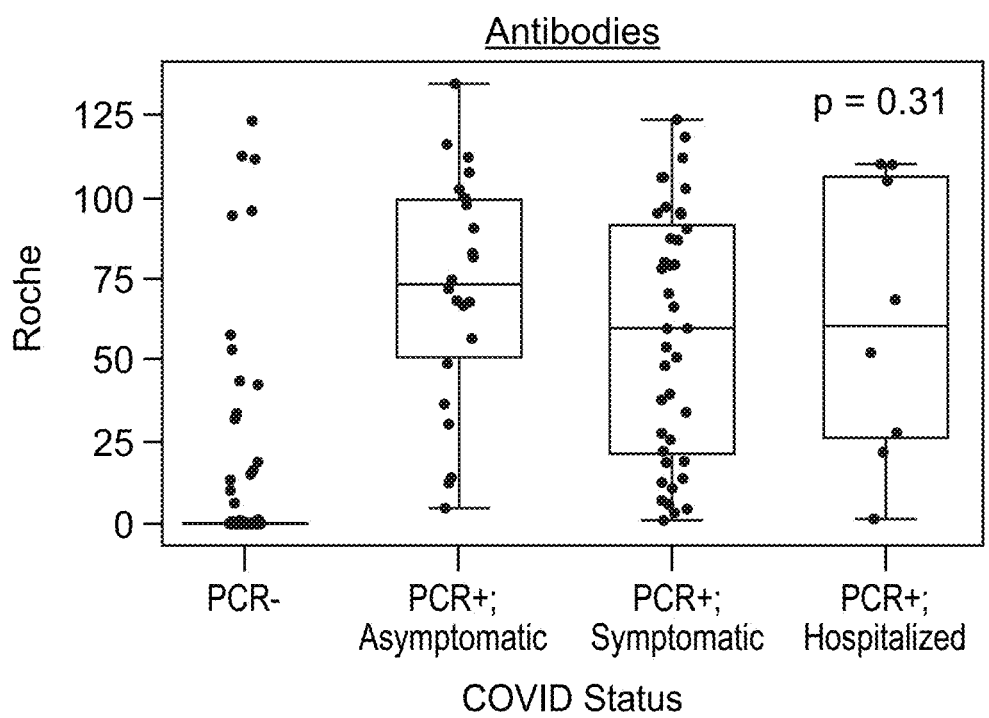

Since almost all subjects with prior confirmed infection had readily detectable SARS-CoV-2 specific T cells in memory, both the depth and breadth of the T-cell response in these subjects were assessed. Asymptomatic subjects demonstrated a T-cell response at 60 or more days from infection that was significantly lower in depth ($p=0.002$; Mann-Whitney-U test) and also showed trends of less breadth ($p=0.16$; Mann-Whitney-U test) compared to those with more severe disease (FIGS. 2A and 2B). These results align with other recent findings that the magnitude of T-cell response is higher in symptomatic subjects and differences may persist for at least 6 months (Zuo 2020). Two hypotheses for this observation are differences in viral load during acute infection and differences in viral persistence until clearance. In contrast, although a high dynamic range was observed over the antibody titers two months post infection, these titers did not correlate with severity of symptoms (FIGS. 2C-2E). Other studies (including Isho 2020, Iyer 2020, Long 2020, Seow 2020) have identified potential differences in antibody levels associated with severity, particularly during the acute phase of illness, but these signals decline with time and seroreversion is sometimes observed. The results here suggest that antibody signals are less informative in the months following infection for measuring prior immune response.

Figure 3B:
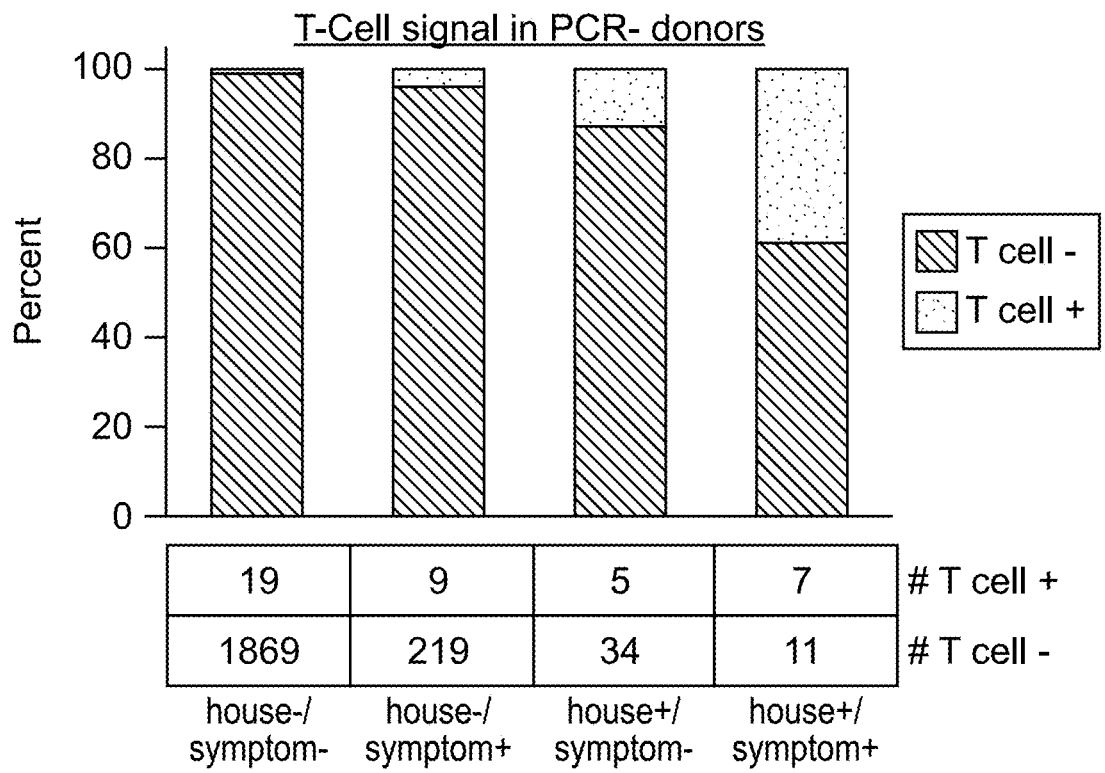
Figure 4:
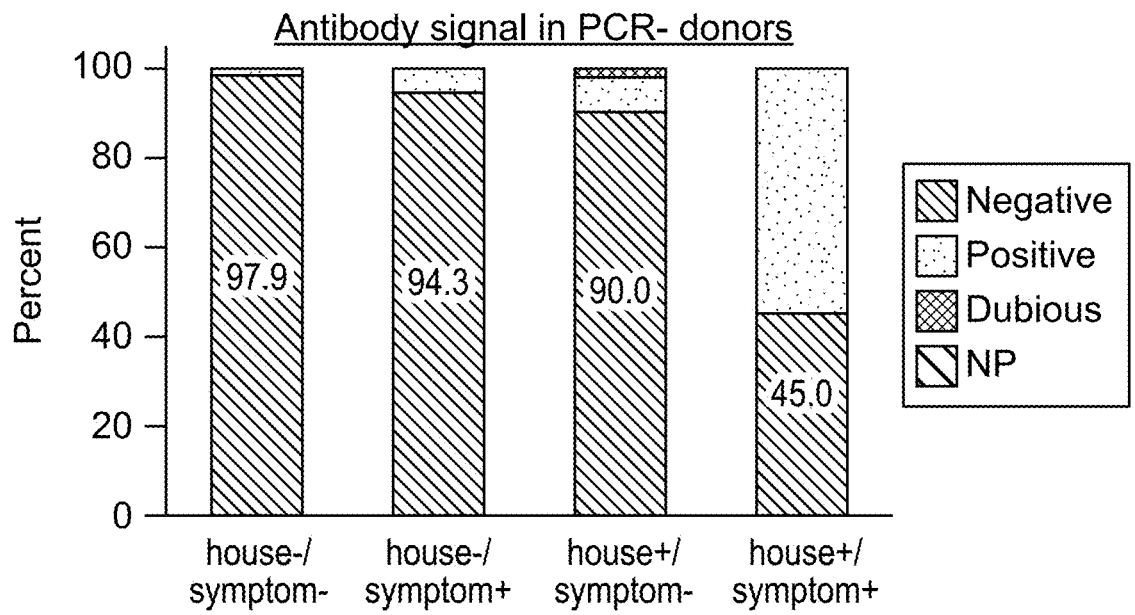
FIG. 4. Percentage of antibody test positives in individuals without a confirmed PCR+ result. Positive antibody test results were observed more often in exposed and/or symptomatic individuals.
Figure 5:
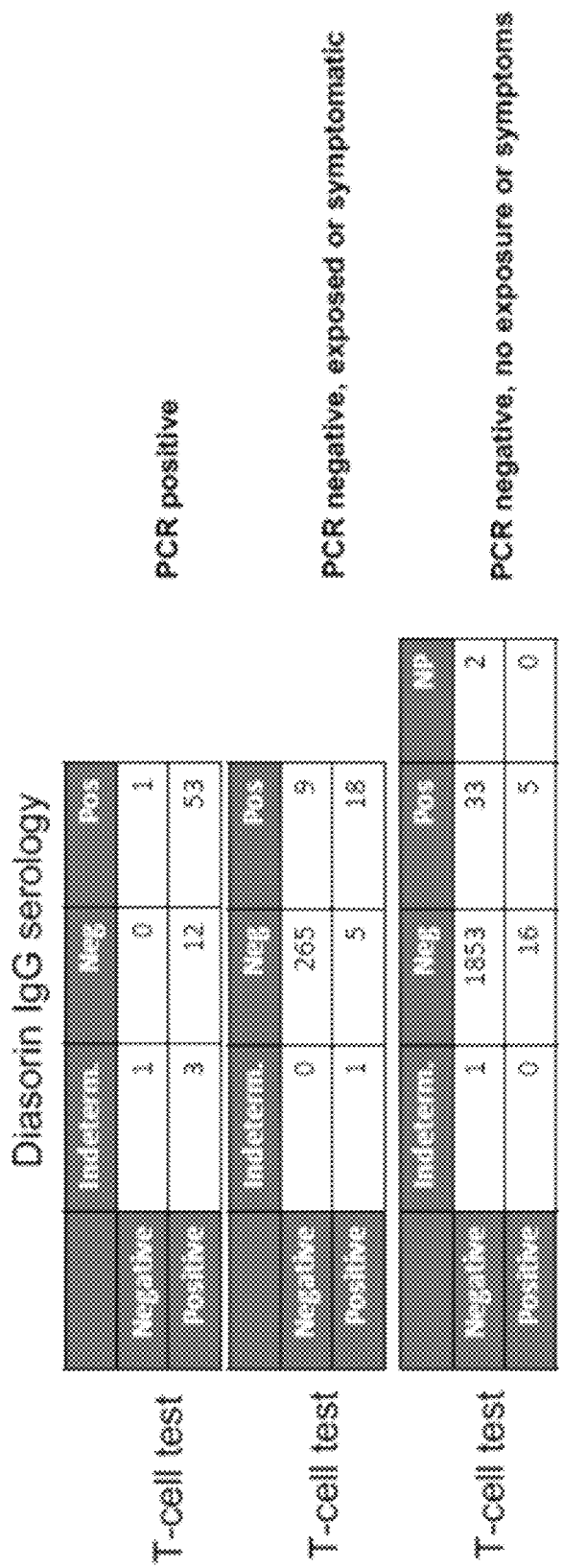
FIG. 5. Comparison of T-cell and serology test results in three subject groups: confirmed PCR+, PCR-who share a household with a PCR+ individual and/or reported symptoms, and PCR without household exposure or symptoms. Results are shared as a contingency table, with negative and positive results for T-cell test, and indeterminate, negative, and positive results for antibody test.

The comprehensive survey across the municipality of Vo' allowed the in-detail exploration of also the general population who tested negative by PCR. Notably, a total of 45 (2.0%) of these 2,220 PCR-negative subjects with a positive T-cell test result, with a level of T-cell response similar to many PCR-confirmed infections were identified (FIG. 3A). Within the entire population of PCR-negative subjects, 304 reported having some symptoms; 8.0% of these subjects (who also had available blood samples) had a positive T-cell test. Whether individuals residing within the same household and reported as close contacts (Lavezzo bioRxiv 2020), but were nonetheless PCR negative, presented a T-cell response was next explored. 25% (15 out of 60) of PCR-individuals with household exposure were T-cell test positives. Overall, positivity rates were 1.1% among individuals with no reported symptoms or household exposure compared to 55% among individuals who reported both symptoms and household exposure (FIG. 3B). Importantly, of 21 subjects that were symptomatic and had detectable T-cell responses, 18 had developed symptoms prior to the PCR surveys. Antibody serology results agreed with the T-cell signature for a majority of the individuals with self-reported symptoms or household exposure (FIG. 4, FIG. 5). However, serology had a higher percentage of positivity (2.0% compared to 1.1%) in subjects without symptoms or household exposure, which may indicate differences in specificity for the two tests.

Taken together, these data indicate that surveying the T-cell response to SARS-CoV-2 can detect cases of prior SARS-CoV-2 infection missed by PCR sampling at high sensitivity and specificity months after potential infection.

Data Availability

Clinical data for this cohort (as described in Lavezzo 2020) is available by typing in a web browser the address: followed by github.com/followed by ncov-ic/followed by SEIR_Covid_Vo. T-cell repertoire profiles are available as part of the ImmuneCODE data resource (Nolan 2020).

CONCLUSION

The results from this study demonstrate the utility of measuring the T-cell response to identify past SARS-CoV-2 infection. This methodology can detect T-cell responses at least two months after infection, even in subjects who were asymptomatic, and can potentially confirm prior infection in individuals who may have been exposed but did not have a confirmatory PCR test. Cases of re-infection have been described (Mulder 2020, Tillett 2020) but as they accumulate and are studied in detail, potential differences in the rates, susceptibility, or severity of re-infection may be explained by the nature of the adaptive immune response, including disease-specific memory T cells, as a measurable and reliable correlate of protection.

REFERENCES

1. Isho B, et al., Immunology 5 (52) eabe5511 (2020).
2. Iyer A S, et al., Science Immunology 5 (52) eabe0367 (2020).
3. Lavezzo E, et al., Nature 584, 425-429 (2020).
4. Long Q X, et al., Nature Medicine 26, 1200-1204 (2020).
5. Mulder M, et al., Clinical Infectious Diseases, ciaa1538 (2020), https://doi.org/10.1093/cid/ciaa1538.
6. Nolan S, et al., 2020: doi: 10.21203/rs.3.rs-51964/v1 preprint.
7. Seow J, et al., Nature Microbiology (2020), https://doi.org/10.1038/s41564-020-00813-8.
8. Snyder T M, et al., 2020. https://doi.org/10.1101/2020.07.31.20165647 medRxiv preprint.
9. Tillett R L, et al. Lancet Infect Dis (2020), S1473-3099 (20) 30764-7.
10. Zuo J, et al., https://doi.org/10.1101/2020.11.01.362319 bioRxiv preprint.
11. World Health Organization, Coronavirus disease 2019 (COVID-19) Situation Report-94 (2020). Published online on 23-4-2020.
12. World Health Organization, WHO Virtual press conference on COVID-19. Mar. 11, 2020. Published online on Mar. 11, 2020.
13. Griffoni, A. et al. Targets of T Cell Responses to SARS-CoV-2 Coronavirus in Humans with COVID-19 Disease and Unexposed Individuals. Cell. 2020-6-25;181 (7): 1489-1501.e15.doi: 10.1016/j.cell.2020.05.015. Epub 2020-5-20.
14. Weiskopf, D. et al. Phenotype and kinetics of SARS-CoV-2-specific T cells in COVID-19 patients with acute respiratory distress syndrome. Science Immunology 26 Jun. 2020: Vol. 5, Issue 48, eabd2071 doi: 10.1126/sciimmunol.abd2071.
15. Sekine, T et al. Robust T cell immunity in convalescent individuals with asymptomatic or mild COVID-19. BioRxiv. doi: https://doi.org/10.1101/2020.06.29.174888.
16. Robins H S, Campregher P V, Srivastava S K, Wacher A, Turtle C J, Kahsai O, Riddell S R, Warren E H, Carlson C S. Comprehensive assessment of T-cell receptor β-chain diversity in αβ T cells. Blood 114 (19): 4099-4107, (2009).
17. Carlson C S, Emerson R O, Sherwood A M, Desmarais C, Chung M, Parsons J M, Steen M S, LaMadrid-Herrmannsfeldt M A, Williamson D, Livingston R J, Wu E, Wood B L, Rieder M J, Robins H S. Using synthetic templates to design an unbiased multiplex PCR assay. Nature Communications 4:2680. (2013).
18. Robins H S, Desmarais C, Matthis J, Livingston R, Andriesen J, Reijonen H, Nepom G, Yee C, Cerosaletti K. Ultra-sensitive detection of rare T cell clones. J. Immunol. Methods 375 (1-2): 14-9. (2012).
19. Klinger, M. et al. Combining next-generation sequencing and immune assays: a novel method for identification of antigen-specific T cells. PLoS One 8, e74231 (2013).
20. Klinger, M. et al. Multiplex identification of antigen-specific T cell receptors using a combination of immune assays and immune receptor sequencing. PLoS One 10, e0141561 (2015).

Accordingly, the preceding merely illustrates the principles of the present disclosure. It will be appreciated that those skilled in the art will be able to devise various arrangements which, although not explicitly described or shown herein, embody the principles of the invention and are included within its spirit and scope. Furthermore, all examples and conditional language recited herein are principally intended to aid the reader in understanding the principles of the invention and the concepts contributed by the inventors to furthering the art, and are to be construed as being without limitation to such specifically recited examples and conditions. Moreover, all statements herein reciting principles, aspects, and embodiments of the invention as well as specific examples thereof, are intended to encompass both structural and functional equivalents thereof. Additionally, it is intended that such equivalents include both currently known equivalents and equivalents developed in the future, i.e., any elements developed that perform the same function, regardless of structure. The scope of the present invention, therefore, is not intended to be limited to the exemplary embodiments shown and described herein.

What is claimed is:

1. A method for treating a subject for COVID-19, comprising:
    identifying a subject as having COVID-19 based on a presence of two or more of the TCRβ CDR3 sequences set forth in SEQ ID NOs: 1, 4, 8, 10, 11, 12, 18, 20, 30, and 37 in a sample obtained from the subject; and
    administering to the subject a COVID-19 therapy comprising remdesivir, protease inhibitors, and/or an anti-SARS-CoV-2 antibody.

2. The method of claim 1, wherein the identifying is based on the presence of three or more of the TCRβ CDR3 sequences set forth in SEQ ID NOs: 1, 4, 8, 10, 11, 12, 18, 20, 30, and 37.

3. The method of claim 1, wherein the identifying is based on the presence of four or more of the TCRβ CDR3 sequences set forth in SEQ ID NOs: 1, 4, 8, 10, 11, 12, 18, 20, 30, and 37.

4. The method of claim 1, wherein the identifying is based on the presence of five or more of the TCRβ CDR3 sequences set forth in SEQ ID NOs: 1, 4, 8, 10, 11, 12, 18, 20, 30, and 37.

5. The method of claim 1, wherein the identifying is based on the presence of six or more of the TCRβ CDR3 sequences set forth in SEQ ID NOs: 1, 4, 8, 10, 11, 12, 18, 20, 30, and 37.

6. The method of claim 1, wherein the identifying is based on the presence of seven or more of the TCRβ CDR3 sequences set forth in SEQ ID NOs: 1, 4, 8, 10, 11, 12, 18, 20, 30, and 37.

7. The method of claim 1, wherein the identifying is based on the presence of eight or more of the TCRβ CDR3 sequences set forth in SEQ ID NOs: 1, 4, 8, 10, 11, 12, 18, 20, 30, and 37.

8. The method of claim 1, wherein the identifying is based on the presence of nine or more of the TCRβ CDR3 sequences set forth in SEQ ID NOs: 1, 4, 8, 10, 11, 12, 18, 20, 30, and 37.

9. The method of claim 1, wherein the identifying is based on the presence of all ten of the TCRβ CDR3 sequences set forth in SEQ ID NOs: 1, 4, 8, 10, 11, 12, 18, 20, 30, and 37.

10. The method of claim 1, wherein the therapy comprises remdesivir.

11. The method of claim 1, wherein the therapy comprises protease inhibitors.

12. The method of claim 1, wherein the therapy comprises anti-SARS-CoV-2 antibody.

* * * * *

SEQUENCE LISTING

<160> NUMBER OF SEQ ID NOS: 206

<210> SEQ ID NO 1
<211> LENGTH: 15
<212> TYPE: PRT
<213> ORGANISM: Artificial sequence
<220> FEATURE:
<223> OTHER INFORMATION: synthetic sequence

<400> SEQUENCE: 1

Cys Ala Ser Ser Gln Gly Asn Arg Ala Asn Thr Glu Ala Phe Phe
1               5                   10                  15

<210> SEQ ID NO 2
<211> LENGTH: 11
<212> TYPE: PRT
<213> ORGANISM: Artificial sequence
<220> FEATURE:
<223> OTHER INFORMATION: synthetic sequence

<400> SEQUENCE: 2

Cys Ser Ala Thr Ser Gly His Glu Gln Tyr Phe
1               5                   10

<210> SEQ ID NO 3
<211> LENGTH: 14
<212> TYPE: PRT
<213> ORGANISM: Artificial sequence
<220> FEATURE:
<223> OTHER INFORMATION: synthetic sequence

<400> SEQUENCE: 3

Cys Ala Ser Ser Gly Thr Gly Ser Thr Asp Thr Gln Tyr Phe
1               5                   10

<210> SEQ ID NO 4
<211> LENGTH: 14
<212> TYPE: PRT
<213> ORGANISM: Artificial sequence
<220> FEATURE:
<223> OTHER INFORMATION: synthetic sequence

<400> SEQUENCE: 4

Cys Ala Ser Thr Gly Thr Gly Ser Thr Asp Thr Gln Tyr Phe
1               5                   10

<210> SEQ ID NO 5
<211> LENGTH: 11
<212> TYPE: PRT
<213> ORGANISM: Artificial sequence
<220> FEATURE:
<223> OTHER INFORMATION: synthetic sequence

<400> SEQUENCE: 5

Cys Ser Ala Arg Ser Gly His Glu Gln Tyr Phe
1               5                   10

<210> SEQ ID NO 6
<211> LENGTH: 11
<212> TYPE: PRT
<213> ORGANISM: Artificial sequence
<220> FEATURE:
<223> OTHER INFORMATION: synthetic sequence

<400> SEQUENCE: 6

Cys Ser Ala Ser Ser Gly His Glu Gln Tyr Phe
1               5                   10

```
<210> SEQ ID NO 7
<211> LENGTH: 15
<212> TYPE: PRT
<213> ORGANISM: Artificial sequence
<220> FEATURE:
<223> OTHER INFORMATION: synthetic sequence

<400> SEQUENCE: 7

Cys Ala Ser Ser Glu Ser Pro Thr Ser Thr Asp Thr Gln Tyr Phe
1               5                   10                  15

<210> SEQ ID NO 8
<211> LENGTH: 11
<212> TYPE: PRT
<213> ORGANISM: Artificial sequence
<220> FEATURE:
<223> OTHER INFORMATION: synthetic sequence

<400> SEQUENCE: 8

Cys Ser Ala Ser Ser Gly His Glu Ala Phe Phe
1               5                   10

<210> SEQ ID NO 9
<211> LENGTH: 13
<212> TYPE: PRT
<213> ORGANISM: Artificial sequence
<220> FEATURE:
<223> OTHER INFORMATION: synthetic sequence

<400> SEQUENCE: 9

Cys Ser Ala Arg Asp Trp Arg Glu Glu Thr Gln Tyr Phe
1               5                   10

<210> SEQ ID NO 10
<211> LENGTH: 13
<212> TYPE: PRT
<213> ORGANISM: Artificial sequence
<220> FEATURE:
<223> OTHER INFORMATION: synthetic sequence

<400> SEQUENCE: 10

Cys Ala Ser Ser Leu Lys Leu Asp Thr Glu Ala Phe Phe
1               5                   10

<210> SEQ ID NO 11
<211> LENGTH: 14
<212> TYPE: PRT
<213> ORGANISM: Artificial sequence
<220> FEATURE:
<223> OTHER INFORMATION: synthetic sequence

<400> SEQUENCE: 11

Cys Ser Ala Lys Ala Gly Gly Arg Gly Glu Thr Gln Tyr Phe
1               5                   10

<210> SEQ ID NO 12
<211> LENGTH: 16
<212> TYPE: PRT
<213> ORGANISM: Artificial sequence
<220> FEATURE:
<223> OTHER INFORMATION: synthetic sequence

<400> SEQUENCE: 12

Cys Ser Ala Arg Arg Gln Gly Val Arg Gly Asn Gln Pro Gln His Phe
1               5                   10                  15
```

```
<210> SEQ ID NO 13
<211> LENGTH: 13
<212> TYPE: PRT
<213> ORGANISM: Artificial sequence
<220> FEATURE:
<223> OTHER INFORMATION: synthetic sequence

<400> SEQUENCE: 13

Cys Ala Ile Ser Glu Arg Gly Gln Asp Glu Gln Tyr Phe
1               5                   10

<210> SEQ ID NO 14
<211> LENGTH: 13
<212> TYPE: PRT
<213> ORGANISM: Artificial sequence
<220> FEATURE:
<223> OTHER INFORMATION: synthetic sequence

<400> SEQUENCE: 14

Cys Ala Ser Ser Leu Lys Leu Asp Ser Pro Leu His Phe
1               5                   10

<210> SEQ ID NO 15
<211> LENGTH: 17
<212> TYPE: PRT
<213> ORGANISM: Artificial sequence
<220> FEATURE:
<223> OTHER INFORMATION: synthetic sequence

<400> SEQUENCE: 15

Cys Ala Ser Ser Pro Arg Leu Ala Gly Ser Ser Tyr Asn Glu Gln Phe
1               5                   10                  15

Phe

<210> SEQ ID NO 16
<211> LENGTH: 14
<212> TYPE: PRT
<213> ORGANISM: Artificial sequence
<220> FEATURE:
<223> OTHER INFORMATION: synthetic sequence

<400> SEQUENCE: 16

Cys Ala Ser Ser Tyr Thr Gly Gln Gly Ala Glu Gln Tyr Phe
1               5                   10

<210> SEQ ID NO 17
<211> LENGTH: 14
<212> TYPE: PRT
<213> ORGANISM: Artificial sequence
<220> FEATURE:
<223> OTHER INFORMATION: synthetic sequence

<400> SEQUENCE: 17

Cys Ala Ser Ser Leu Glu Gly Ser Thr Asp Thr Gln Tyr Phe
1               5                   10

<210> SEQ ID NO 18
<211> LENGTH: 14
<212> TYPE: PRT
<213> ORGANISM: Artificial sequence
<220> FEATURE:
<223> OTHER INFORMATION: synthetic sequence

<400> SEQUENCE: 18

Cys Ser Ala Lys Ala Gly Gly Arg Gly Asp Thr Gln Tyr Phe
1               5                   10
```

<210> SEQ ID NO 19
<211> LENGTH: 11
<212> TYPE: PRT
<213> ORGANISM: Artificial sequence
<220> FEATURE:
<223> OTHER INFORMATION: synthetic sequence

<400> SEQUENCE: 19

Cys Ser Ala Arg Ser Gly Phe Glu Gln Tyr Phe
1               5                   10

<210> SEQ ID NO 20
<211> LENGTH: 15
<212> TYPE: PRT
<213> ORGANISM: Artificial sequence
<220> FEATURE:
<223> OTHER INFORMATION: synthetic sequence

<400> SEQUENCE: 20

Cys Ala Ser Ser Thr Gly Asp Gly Tyr Asn Ser Pro Leu His Phe
1               5                   10                  15

<210> SEQ ID NO 21
<211> LENGTH: 15
<212> TYPE: PRT
<213> ORGANISM: Artificial sequence
<220> FEATURE:
<223> OTHER INFORMATION: synthetic sequence

<400> SEQUENCE: 21

Cys Ala Ser Ser Pro Pro Gly Gln Gly Glu His Gly Tyr Thr Phe
1               5                   10                  15

<210> SEQ ID NO 22
<211> LENGTH: 15
<212> TYPE: PRT
<213> ORGANISM: Artificial sequence
<220> FEATURE:
<223> OTHER INFORMATION: synthetic sequence

<400> SEQUENCE: 22

Cys Ser Ala Arg Val Gly Thr Ala Thr Asn Glu Lys Leu Phe Phe
1               5                   10                  15

<210> SEQ ID NO 23
<211> LENGTH: 15
<212> TYPE: PRT
<213> ORGANISM: Artificial sequence
<220> FEATURE:
<223> OTHER INFORMATION: synthetic sequence

<400> SEQUENCE: 23

Cys Ala Ser Ser Ser Gly Asp Gly Tyr Asn Ser Pro Leu His Phe
1               5                   10                  15

<210> SEQ ID NO 24
<211> LENGTH: 15
<212> TYPE: PRT
<213> ORGANISM: Artificial sequence
<220> FEATURE:
<223> OTHER INFORMATION: synthetic sequence

<400> SEQUENCE: 24

Cys Ala Ser Ser Val Asp Gln Gly Ala Lys Glu Thr Gln Tyr Phe
1               5                   10                  15

```
<210> SEQ ID NO 25
<211> LENGTH: 14
<212> TYPE: PRT
<213> ORGANISM: Artificial sequence
<220> FEATURE:
<223> OTHER INFORMATION: synthetic sequence

<400> SEQUENCE: 25

Cys Ala Ser Ser Tyr Thr Gly Gln Gly Ala Glu Ala Phe Phe
1               5                   10

<210> SEQ ID NO 26
<211> LENGTH: 14
<212> TYPE: PRT
<213> ORGANISM: Artificial sequence
<220> FEATURE:
<223> OTHER INFORMATION: synthetic sequence

<400> SEQUENCE: 26

Cys Ala Ser Ser Leu Asn Arg Gly Asp Tyr Gly Tyr Thr Phe
1               5                   10

<210> SEQ ID NO 27
<211> LENGTH: 16
<212> TYPE: PRT
<213> ORGANISM: Artificial sequence
<220> FEATURE:
<223> OTHER INFORMATION: synthetic sequence

<400> SEQUENCE: 27

Cys Ala Ser Ser Ile Val Trp Thr Ala Asp Asn Gln Pro Gln His Phe
1               5                   10                  15

<210> SEQ ID NO 28
<211> LENGTH: 14
<212> TYPE: PRT
<213> ORGANISM: Artificial sequence
<220> FEATURE:
<223> OTHER INFORMATION: synthetic sequence

<400> SEQUENCE: 28

Cys Ala Ser Ser Leu Ser Ala Pro Gln Glu Thr Gln Tyr Phe
1               5                   10

<210> SEQ ID NO 29
<211> LENGTH: 15
<212> TYPE: PRT
<213> ORGANISM: Artificial sequence
<220> FEATURE:
<223> OTHER INFORMATION: synthetic sequence

<400> SEQUENCE: 29

Cys Ala Ser Ser Glu Ser Pro Val Ser Thr Asp Thr Gln Tyr Phe
1               5                   10                  15

<210> SEQ ID NO 30
<211> LENGTH: 17
<212> TYPE: PRT
<213> ORGANISM: Artificial sequence
<220> FEATURE:
<223> OTHER INFORMATION: synthetic sequence

<400> SEQUENCE: 30

Cys Ala Ser Ser Leu Ala Leu Gly Gly Ala Gly Asn Gln Pro Gln His
1               5                   10                  15

Phe
```

<210> SEQ ID NO 31
<211> LENGTH: 16
<212> TYPE: PRT
<213> ORGANISM: Artificial sequence
<220> FEATURE:
<223> OTHER INFORMATION: synthetic sequence

<400> SEQUENCE: 31

Cys Ala Ser Ser Ile Leu Gly Ser Ala Asn Thr Gly Glu Leu Phe Phe
1               5                   10                  15

<210> SEQ ID NO 32
<211> LENGTH: 13
<212> TYPE: PRT
<213> ORGANISM: Artificial sequence
<220> FEATURE:
<223> OTHER INFORMATION: synthetic sequence

<400> SEQUENCE: 32

Cys Ala Ser Ser Leu Lys Met Asp Thr Glu Ala Phe Phe
1               5                   10

<210> SEQ ID NO 33
<211> LENGTH: 14
<212> TYPE: PRT
<213> ORGANISM: Artificial sequence
<220> FEATURE:
<223> OTHER INFORMATION: synthetic sequence

<400> SEQUENCE: 33

Cys Ala Ser Thr Leu Glu Gly Ser Thr Asp Thr Gln Tyr Phe
1               5                   10

<210> SEQ ID NO 34
<211> LENGTH: 16
<212> TYPE: PRT
<213> ORGANISM: Artificial sequence
<220> FEATURE:
<223> OTHER INFORMATION: synthetic sequence

<400> SEQUENCE: 34

Cys Ser Ala Arg Glu Gly Gly Val Tyr Ser Asn Gln Pro Gln His Phe
1               5                   10                  15

<210> SEQ ID NO 35
<211> LENGTH: 14
<212> TYPE: PRT
<213> ORGANISM: Artificial sequence
<220> FEATURE:
<223> OTHER INFORMATION: synthetic sequence

<400> SEQUENCE: 35

Cys Ala Ser Ser Tyr Thr Gly Gln Gly Ala Gly Tyr Thr Phe
1               5                   10

<210> SEQ ID NO 36
<211> LENGTH: 16
<212> TYPE: PRT
<213> ORGANISM: Artificial sequence
<220> FEATURE:
<223> OTHER INFORMATION: synthetic sequence

<400> SEQUENCE: 36

Cys Ser Ala Arg Asp Asp Arg Leu Tyr Ser Asn Gln Pro Gln His Phe
1               5                   10                  15

<210> SEQ ID NO 37
<211> LENGTH: 14
<212> TYPE: PRT
<213> ORGANISM: Artificial sequence
<220> FEATURE:
<223> OTHER INFORMATION: synthetic sequence

<400> SEQUENCE: 37

Cys Ser Ala Arg Arg Asp Ser Arg Thr Asp Thr Gln Tyr Phe
1               5                   10

<210> SEQ ID NO 38
<211> LENGTH: 13
<212> TYPE: PRT
<213> ORGANISM: Artificial sequence
<220> FEATURE:
<223> OTHER INFORMATION: synthetic sequence

<400> SEQUENCE: 38

Cys Ala Ile Ser Ala Arg Gly Gln Asp Glu Gln Tyr Phe
1               5                   10

<210> SEQ ID NO 39
<211> LENGTH: 16
<212> TYPE: PRT
<213> ORGANISM: Artificial sequence
<220> FEATURE:
<223> OTHER INFORMATION: synthetic sequence

<400> SEQUENCE: 39

Cys Ala Ser Ser Ile Leu Gly Ala Ala Asn Thr Gly Glu Leu Phe Phe
1               5                   10                  15

<210> SEQ ID NO 40
<211> LENGTH: 11
<212> TYPE: PRT
<213> ORGANISM: Artificial sequence
<220> FEATURE:
<223> OTHER INFORMATION: synthetic sequence

<400> SEQUENCE: 40

Cys Ser Ala Thr Ser Gly His Glu Gln Phe Phe
1               5                   10

<210> SEQ ID NO 41
<211> LENGTH: 14
<212> TYPE: PRT
<213> ORGANISM: Artificial sequence
<220> FEATURE:
<223> OTHER INFORMATION: synthetic sequence

<400> SEQUENCE: 41

Cys Ala Ser Ser Leu Lys Gly Ser Thr Asp Thr Gln Tyr Phe
1               5                   10

<210> SEQ ID NO 42
<211> LENGTH: 18
<212> TYPE: PRT
<213> ORGANISM: Artificial sequence
<220> FEATURE:
<223> OTHER INFORMATION: synthetic sequence

<400> SEQUENCE: 42

Cys Ala Ser Ser Arg Thr Gly Thr Gly Ser Ser Tyr Asn Ser Pro Leu
1               5                   10                  15

His Phe

```
<210> SEQ ID NO 43
<211> LENGTH: 16
<212> TYPE: PRT
<213> ORGANISM: Artificial sequence
<220> FEATURE:
<223> OTHER INFORMATION: synthetic sequence

<400> SEQUENCE: 43

Cys Ser Ala Arg Pro Gly Gly Val Tyr Ser Asn Gln Pro Gln His Phe
1               5                   10                  15

<210> SEQ ID NO 44
<211> LENGTH: 16
<212> TYPE: PRT
<213> ORGANISM: Artificial sequence
<220> FEATURE:
<223> OTHER INFORMATION: synthetic sequence

<400> SEQUENCE: 44

Cys Ser Ala Arg Ala Gly Gly Val Tyr Ser Asn Gln Pro Gln His Phe
1               5                   10                  15

<210> SEQ ID NO 45
<211> LENGTH: 16
<212> TYPE: PRT
<213> ORGANISM: Artificial sequence
<220> FEATURE:
<223> OTHER INFORMATION: synthetic sequence

<400> SEQUENCE: 45

Cys Ala Ser Ser Thr Pro Asp Arg Gly Asn Asn Gln Pro Gln His Phe
1               5                   10                  15

<210> SEQ ID NO 46
<211> LENGTH: 13
<212> TYPE: PRT
<213> ORGANISM: Artificial sequence
<220> FEATURE:
<223> OTHER INFORMATION: synthetic sequence

<400> SEQUENCE: 46

Cys Ser Ala Gln Thr Gly Val Asn Gln Pro Gln His Phe
1               5                   10

<210> SEQ ID NO 47
<211> LENGTH: 13
<212> TYPE: PRT
<213> ORGANISM: Artificial sequence
<220> FEATURE:
<223> OTHER INFORMATION: synthetic sequence

<400> SEQUENCE: 47

Cys Ala Ser Ser Leu Lys Gln Asp Thr Glu Ala Phe Phe
1               5                   10

<210> SEQ ID NO 48
<211> LENGTH: 14
<212> TYPE: PRT
<213> ORGANISM: Artificial sequence
<220> FEATURE:
<223> OTHER INFORMATION: synthetic sequence

<400> SEQUENCE: 48

Cys Ala Ser Ser Tyr Thr Gly Gln Gly Gln Pro Gln His Phe
1               5                   10
```

<210> SEQ ID NO 49
<211> LENGTH: 14
<212> TYPE: PRT
<213> ORGANISM: Artificial sequence
<220> FEATURE:
<223> OTHER INFORMATION: synthetic sequence

<400> SEQUENCE: 49

Cys Ala Ser Ser Asp Arg Gly Pro Asn Asn Glu Gln Phe Phe
1               5                   10

<210> SEQ ID NO 50
<211> LENGTH: 15
<212> TYPE: PRT
<213> ORGANISM: Artificial sequence
<220> FEATURE:
<223> OTHER INFORMATION: synthetic sequence

<400> SEQUENCE: 50

Cys Ala Ser Ser Gln Glu Arg Gly Gly Asn Gln Pro Gln His Phe
1               5                   10                  15

<210> SEQ ID NO 51
<211> LENGTH: 13
<212> TYPE: PRT
<213> ORGANISM: Artificial sequence
<220> FEATURE:
<223> OTHER INFORMATION: synthetic sequence

<400> SEQUENCE: 51

Cys Ala Ser Ser Pro Pro Gly Leu Tyr Gly Tyr Thr Phe
1               5                   10

<210> SEQ ID NO 52
<211> LENGTH: 15
<212> TYPE: PRT
<213> ORGANISM: Artificial sequence
<220> FEATURE:
<223> OTHER INFORMATION: synthetic sequence

<400> SEQUENCE: 52

Cys Ser Ala Arg Glu Gly Thr Ala Ser Thr Asp Thr Gln Tyr Phe
1               5                   10                  15

<210> SEQ ID NO 53
<211> LENGTH: 14
<212> TYPE: PRT
<213> ORGANISM: Artificial sequence
<220> FEATURE:
<223> OTHER INFORMATION: synthetic sequence

<400> SEQUENCE: 53

Cys Ala Ser Ser Tyr Pro Glu Met Asn Thr Glu Ala Phe Phe
1               5                   10

<210> SEQ ID NO 54
<211> LENGTH: 15
<212> TYPE: PRT
<213> ORGANISM: Artificial sequence
<220> FEATURE:
<223> OTHER INFORMATION: synthetic sequence

<400> SEQUENCE: 54

Cys Ser Val Arg Thr Gly Thr Gly Asn Thr Gly Glu Leu Phe Phe
1               5                   10                  15

<210> SEQ ID NO 55
<211> LENGTH: 15
<212> TYPE: PRT
<213> ORGANISM: Artificial sequence
<220> FEATURE:
<223> OTHER INFORMATION: synthetic sequence

<400> SEQUENCE: 55

Cys Ala Ser Ser Glu Ser Arg Thr Glu Asn Ser Pro Leu His Phe
1               5                   10                  15

<210> SEQ ID NO 56
<211> LENGTH: 14
<212> TYPE: PRT
<213> ORGANISM: Artificial sequence
<220> FEATURE:
<223> OTHER INFORMATION: synthetic sequence

<400> SEQUENCE: 56

Cys Ala Ser Ser Leu Gly Ala Pro Gln Glu Thr Gln Tyr Phe
1               5                   10

<210> SEQ ID NO 57
<211> LENGTH: 14
<212> TYPE: PRT
<213> ORGANISM: Artificial sequence
<220> FEATURE:
<223> OTHER INFORMATION: synthetic sequence

<400> SEQUENCE: 57

Cys Ser Ala Arg Arg Asp Ser Arg Ala Asp Thr Gln Tyr Phe
1               5                   10

<210> SEQ ID NO 58
<211> LENGTH: 15
<212> TYPE: PRT
<213> ORGANISM: Artificial sequence
<220> FEATURE:
<223> OTHER INFORMATION: synthetic sequence

<400> SEQUENCE: 58

Cys Ala Thr Ser Asp Pro Arg Asp Arg Thr Tyr Glu Gln Tyr Phe
1               5                   10                  15

<210> SEQ ID NO 59
<211> LENGTH: 14
<212> TYPE: PRT
<213> ORGANISM: Artificial sequence
<220> FEATURE:
<223> OTHER INFORMATION: synthetic sequence

<400> SEQUENCE: 59

Cys Ser Ala Lys Ser Gly Gly Arg Gly Glu Thr Gln Tyr Phe
1               5                   10

<210> SEQ ID NO 60
<211> LENGTH: 14
<212> TYPE: PRT
<213> ORGANISM: Artificial sequence
<220> FEATURE:
<223> OTHER INFORMATION: synthetic sequence

<400> SEQUENCE: 60

Cys Ala Ser Ser Leu Val Trp Gly Asn Gln Pro Gln His Phe
1               5                   10

<210> SEQ ID NO 61

```
<211> LENGTH: 14
<212> TYPE: PRT
<213> ORGANISM: Artificial sequence
<220> FEATURE:
<223> OTHER INFORMATION: synthetic sequence

<400> SEQUENCE: 61

Cys Ala Ser Ser Leu Glu Gly Gly Ser Tyr Gly Tyr Thr Phe
1               5                   10

<210> SEQ ID NO 62
<211> LENGTH: 15
<212> TYPE: PRT
<213> ORGANISM: Artificial sequence
<220> FEATURE:
<223> OTHER INFORMATION: synthetic sequence

<400> SEQUENCE: 62

Cys Ala Ser Ser Leu Asp Gln Gly Ala Lys Glu Thr Gln Tyr Phe
1               5                   10                  15

<210> SEQ ID NO 63
<211> LENGTH: 14
<212> TYPE: PRT
<213> ORGANISM: Artificial sequence
<220> FEATURE:
<223> OTHER INFORMATION: synthetic sequence

<400> SEQUENCE: 63

Cys Ala Thr Ser Gly Thr Gly Ser Thr Asp Thr Gln Tyr Phe
1               5                   10

<210> SEQ ID NO 64
<211> LENGTH: 14
<212> TYPE: PRT
<213> ORGANISM: Artificial sequence
<220> FEATURE:
<223> OTHER INFORMATION: synthetic sequence

<400> SEQUENCE: 64

Cys Ala Ser Thr Gly Gln Gly Ser Thr Asp Thr Gln Tyr Phe
1               5                   10

<210> SEQ ID NO 65
<211> LENGTH: 11
<212> TYPE: PRT
<213> ORGANISM: Artificial sequence
<220> FEATURE:
<223> OTHER INFORMATION: synthetic sequence

<400> SEQUENCE: 65

Cys Ser Ala Lys Ser Gly His Glu Gln Tyr Phe
1               5                   10

<210> SEQ ID NO 66
<211> LENGTH: 13
<212> TYPE: PRT
<213> ORGANISM: Artificial sequence
<220> FEATURE:
<223> OTHER INFORMATION: synthetic sequence

<400> SEQUENCE: 66

Cys Ala Ser Ser Tyr Arg Gly Ala Asn Gly Tyr Thr Phe
1               5                   10

<210> SEQ ID NO 67
<211> LENGTH: 15
```

```
<212> TYPE: PRT
<213> ORGANISM: Artificial sequence
<220> FEATURE:
<223> OTHER INFORMATION: synthetic sequence

<400> SEQUENCE: 67

Cys Ser Ala Arg Arg Gly Gly Pro Thr Asn Thr Glu Ala Phe Phe
1               5                   10                  15

<210> SEQ ID NO 68
<211> LENGTH: 16
<212> TYPE: PRT
<213> ORGANISM: Artificial sequence
<220> FEATURE:
<223> OTHER INFORMATION: synthetic sequence

<400> SEQUENCE: 68

Cys Ala Ser Ser Pro Ser Ser Gly Gly Asn Thr Gly Glu Leu Phe Phe
1               5                   10                  15

<210> SEQ ID NO 69
<211> LENGTH: 15
<212> TYPE: PRT
<213> ORGANISM: Artificial sequence
<220> FEATURE:
<223> OTHER INFORMATION: synthetic sequence

<400> SEQUENCE: 69

Cys Ser Ala Leu Pro Gly Gly Val Ser Asn Gln Pro Gln His Phe
1               5                   10                  15

<210> SEQ ID NO 70
<211> LENGTH: 14
<212> TYPE: PRT
<213> ORGANISM: Artificial sequence
<220> FEATURE:
<223> OTHER INFORMATION: synthetic sequence

<400> SEQUENCE: 70

Cys Ser Ala Arg Trp Gly Gly Arg Gly Glu Thr Gln Tyr Phe
1               5                   10

<210> SEQ ID NO 71
<211> LENGTH: 13
<212> TYPE: PRT
<213> ORGANISM: Artificial sequence
<220> FEATURE:
<223> OTHER INFORMATION: synthetic sequence

<400> SEQUENCE: 71

Cys Ser Val Ala Leu Gly Val Asn Gln Pro Gln His Phe
1               5                   10

<210> SEQ ID NO 72
<211> LENGTH: 16
<212> TYPE: PRT
<213> ORGANISM: Artificial sequence
<220> FEATURE:
<223> OTHER INFORMATION: synthetic sequence

<400> SEQUENCE: 72

Cys Ala Ser Ser Leu Val Thr Gly Ala Ser Thr Asp Thr Gln Tyr Phe
1               5                   10                  15

<210> SEQ ID NO 73
<211> LENGTH: 16
<212> TYPE: PRT
```

```
<213> ORGANISM: Artificial sequence
<220> FEATURE:
<223> OTHER INFORMATION: synthetic sequence

<400> SEQUENCE: 73

Cys Ala Ser Ser Arg Gly Thr Ser Gly Phe Gln Glu Thr Gln Tyr Phe
1               5                   10                  15

<210> SEQ ID NO 74
<211> LENGTH: 14
<212> TYPE: PRT
<213> ORGANISM: Artificial sequence
<220> FEATURE:
<223> OTHER INFORMATION: synthetic sequence

<400> SEQUENCE: 74

Cys Ala Ser Ser Tyr Thr Gly Gln Gly Ser Gly Tyr Thr Phe
1               5                   10

<210> SEQ ID NO 75
<211> LENGTH: 14
<212> TYPE: PRT
<213> ORGANISM: Artificial sequence
<220> FEATURE:
<223> OTHER INFORMATION: synthetic sequence

<400> SEQUENCE: 75

Cys Ser Ala Lys Gln Gly Ala Asn Thr Gly Glu Leu Phe Phe
1               5                   10

<210> SEQ ID NO 76
<211> LENGTH: 14
<212> TYPE: PRT
<213> ORGANISM: Artificial sequence
<220> FEATURE:
<223> OTHER INFORMATION: synthetic sequence

<400> SEQUENCE: 76

Cys Ala Thr Thr Gly Thr Gly Ser Thr Asp Thr Gln Tyr Phe
1               5                   10

<210> SEQ ID NO 77
<211> LENGTH: 17
<212> TYPE: PRT
<213> ORGANISM: Artificial sequence
<220> FEATURE:
<223> OTHER INFORMATION: synthetic sequence

<400> SEQUENCE: 77

Cys Ala Ser Ser Ile Gly Leu Ala Gly Leu Thr Gln Glu Thr Gln Tyr
1               5                   10                  15

Phe

<210> SEQ ID NO 78
<211> LENGTH: 14
<212> TYPE: PRT
<213> ORGANISM: Artificial sequence
<220> FEATURE:
<223> OTHER INFORMATION: synthetic sequence

<400> SEQUENCE: 78

Cys Ala Ser Ser Glu Gly Ala Ser Asn Gln Pro Gln His Phe
1               5                   10

<210> SEQ ID NO 79
<211> LENGTH: 13
```

```
<212> TYPE: PRT
<213> ORGANISM: Artificial sequence
<220> FEATURE:
<223> OTHER INFORMATION: synthetic sequence

<400> SEQUENCE: 79

Cys Ser Ala Arg Asp Trp Arg Gly Glu Thr Gln Tyr Phe
1               5                   10

<210> SEQ ID NO 80
<211> LENGTH: 13
<212> TYPE: PRT
<213> ORGANISM: Artificial sequence
<220> FEATURE:
<223> OTHER INFORMATION: synthetic sequence

<400> SEQUENCE: 80

Cys Ser Ala Arg Asp Trp Lys Glu Glu Thr Gln Tyr Phe
1               5                   10

<210> SEQ ID NO 81
<211> LENGTH: 15
<212> TYPE: PRT
<213> ORGANISM: Artificial sequence
<220> FEATURE:
<223> OTHER INFORMATION: synthetic sequence

<400> SEQUENCE: 81

Cys Ala Ser Arg Arg Gln Val Tyr Gly Ala Asn Val Leu Thr Phe
1               5                   10                  15

<210> SEQ ID NO 82
<211> LENGTH: 14
<212> TYPE: PRT
<213> ORGANISM: Artificial sequence
<220> FEATURE:
<223> OTHER INFORMATION: synthetic sequence

<400> SEQUENCE: 82

Cys Ala Ser Ser Thr Gly Gly Arg Leu Tyr Gly Tyr Thr Phe
1               5                   10

<210> SEQ ID NO 83
<211> LENGTH: 18
<212> TYPE: PRT
<213> ORGANISM: Artificial sequence
<220> FEATURE:
<223> OTHER INFORMATION: synthetic sequence

<400> SEQUENCE: 83

Cys Ala Ser Ser Arg Thr Gly Leu Arg Ser Ser Tyr Asn Ser Pro Leu
1               5                   10                  15
His Phe

<210> SEQ ID NO 84
<211> LENGTH: 17
<212> TYPE: PRT
<213> ORGANISM: Artificial sequence
<220> FEATURE:
<223> OTHER INFORMATION: synthetic sequence

<400> SEQUENCE: 84

Cys Ala Ser Ser Pro Arg Leu Ala Gly Gly Ser Tyr Asn Glu Gln Phe
1               5                   10                  15
Phe
```

<210> SEQ ID NO 85
<211> LENGTH: 13
<212> TYPE: PRT
<213> ORGANISM: Artificial sequence
<220> FEATURE:
<223> OTHER INFORMATION: synthetic sequence

<400> SEQUENCE: 85

Cys Ala Ser Ser Leu Arg Tyr Gln Glu Thr Gln Tyr Phe
1               5                  10

<210> SEQ ID NO 86
<211> LENGTH: 14
<212> TYPE: PRT
<213> ORGANISM: Artificial sequence
<220> FEATURE:
<223> OTHER INFORMATION: synthetic sequence

<400> SEQUENCE: 86

Cys Ser Ala Arg Trp Gly Gly Arg Gly Asp Thr Gln Tyr Phe
1               5                  10

<210> SEQ ID NO 87
<211> LENGTH: 16
<212> TYPE: PRT
<213> ORGANISM: Artificial sequence
<220> FEATURE:
<223> OTHER INFORMATION: synthetic sequence

<400> SEQUENCE: 87

Cys Ser Ala Pro Pro Gly Gly Gln Tyr Ser Asn Gln Pro Gln His Phe
1               5                  10                  15

<210> SEQ ID NO 88
<211> LENGTH: 16
<212> TYPE: PRT
<213> ORGANISM: Artificial sequence
<220> FEATURE:
<223> OTHER INFORMATION: synthetic sequence

<400> SEQUENCE: 88

Cys Ala Ser Ser Val Arg Asp Arg Val Asn Thr Gly Glu Leu Phe Phe
1               5                  10                  15

<210> SEQ ID NO 89
<211> LENGTH: 16
<212> TYPE: PRT
<213> ORGANISM: Artificial sequence
<220> FEATURE:
<223> OTHER INFORMATION: synthetic sequence

<400> SEQUENCE: 89

Cys Ser Ala Arg Glu Gly Gly Ala Tyr Ser Asn Gln Pro Gln His Phe
1               5                  10                  15

<210> SEQ ID NO 90
<211> LENGTH: 14
<212> TYPE: PRT
<213> ORGANISM: Artificial sequence
<220> FEATURE:
<223> OTHER INFORMATION: synthetic sequence

<400> SEQUENCE: 90

Cys Ser Ala Lys Arg Gly Gly Arg Gly Glu Thr Gln Tyr Phe
1               5                  10

```
<210> SEQ ID NO 91
<211> LENGTH: 14
<212> TYPE: PRT
<213> ORGANISM: Artificial sequence
<220> FEATURE:
<223> OTHER INFORMATION: synthetic sequence

<400> SEQUENCE: 91

Cys Ala Ser Ser Tyr Pro Glu Asp Asn Ser Pro Leu His Phe
1               5                   10

<210> SEQ ID NO 92
<211> LENGTH: 11
<212> TYPE: PRT
<213> ORGANISM: Artificial sequence
<220> FEATURE:
<223> OTHER INFORMATION: synthetic sequence

<400> SEQUENCE: 92

Cys Ala Ser Ser Pro Asp Ile Glu Ala Phe Phe
1               5                   10

<210> SEQ ID NO 93
<211> LENGTH: 15
<212> TYPE: PRT
<213> ORGANISM: Artificial sequence
<220> FEATURE:
<223> OTHER INFORMATION: synthetic sequence

<400> SEQUENCE: 93

Cys Ala Ser Ser Gln Ala Gly Gly Ser Thr Asp Thr Gln Tyr Phe
1               5                   10                  15

<210> SEQ ID NO 94
<211> LENGTH: 16
<212> TYPE: PRT
<213> ORGANISM: Artificial sequence
<220> FEATURE:
<223> OTHER INFORMATION: synthetic sequence

<400> SEQUENCE: 94

Cys Ala Ser Ser Val Glu Gly Gly Asp Tyr Gln Glu Thr Gln Tyr Phe
1               5                   10                  15

<210> SEQ ID NO 95
<211> LENGTH: 15
<212> TYPE: PRT
<213> ORGANISM: Artificial sequence
<220> FEATURE:
<223> OTHER INFORMATION: synthetic sequence

<400> SEQUENCE: 95

Cys Ala Ser Ser Arg Ala Gly Gly Ser Thr Asp Thr Gln Tyr Phe
1               5                   10                  15

<210> SEQ ID NO 96
<211> LENGTH: 16
<212> TYPE: PRT
<213> ORGANISM: Artificial sequence
<220> FEATURE:
<223> OTHER INFORMATION: synthetic sequence

<400> SEQUENCE: 96

Cys Ala Ser Ser Leu Leu Ser Thr Ala Asn Thr Gly Glu Leu Phe Phe
1               5                   10                  15

<210> SEQ ID NO 97
```

```
<211> LENGTH: 14
<212> TYPE: PRT
<213> ORGANISM: Artificial sequence
<220> FEATURE:
<223> OTHER INFORMATION: synthetic sequence

<400> SEQUENCE: 97

Cys Ala Ser Ser Tyr Ala Glu Met Asn Thr Glu Ala Phe Phe
1               5                   10

<210> SEQ ID NO 98
<211> LENGTH: 11
<212> TYPE: PRT
<213> ORGANISM: Artificial sequence
<220> FEATURE:
<223> OTHER INFORMATION: synthetic sequence

<400> SEQUENCE: 98

Cys Ser Ala Ser Ser Gly His Glu Gln Phe Phe
1               5                   10

<210> SEQ ID NO 99
<211> LENGTH: 11
<212> TYPE: PRT
<213> ORGANISM: Artificial sequence
<220> FEATURE:
<223> OTHER INFORMATION: synthetic sequence

<400> SEQUENCE: 99

Cys Ser Ala Arg Ser Gly His Glu Gln Phe Phe
1               5                   10

<210> SEQ ID NO 100
<211> LENGTH: 15
<212> TYPE: PRT
<213> ORGANISM: Artificial sequence
<220> FEATURE:
<223> OTHER INFORMATION: synthetic sequence

<400> SEQUENCE: 100

Cys Ala Ser Ser Leu Gly Leu Ala Tyr Thr Asp Thr Gln Tyr Phe
1               5                   10                  15

<210> SEQ ID NO 101
<211> LENGTH: 18
<212> TYPE: PRT
<213> ORGANISM: Artificial sequence
<220> FEATURE:
<223> OTHER INFORMATION: synthetic sequence

<400> SEQUENCE: 101

Cys Ala Ser Ser Arg Thr Gly Leu Gly Ser Ser Tyr Asn Ser Pro Leu
1               5                   10                  15

His Phe

<210> SEQ ID NO 102
<211> LENGTH: 18
<212> TYPE: PRT
<213> ORGANISM: Artificial sequence
<220> FEATURE:
<223> OTHER INFORMATION: synthetic sequence

<400> SEQUENCE: 102

Cys Ala Ser Ser Arg Thr Gly Ala Arg Ser Ser Tyr Asn Ser Pro Leu
1               5                   10                  15

His Phe
```

```
<210> SEQ ID NO 103
<211> LENGTH: 18
<212> TYPE: PRT
<213> ORGANISM: Artificial sequence
<220> FEATURE:
<223> OTHER INFORMATION: synthetic sequence

<400> SEQUENCE: 103

Cys Ala Ser Ser Arg Thr Gly Val Arg Ser Ser Tyr Asn Ser Pro Leu
1               5                   10                  15

His Phe

<210> SEQ ID NO 104
<211> LENGTH: 14
<212> TYPE: PRT
<213> ORGANISM: Artificial sequence
<220> FEATURE:
<223> OTHER INFORMATION: synthetic sequence

<400> SEQUENCE: 104

Cys Ala Ser Thr Arg Glu Gly Ser Thr Asp Thr Gln Tyr Phe
1               5                   10

<210> SEQ ID NO 105
<211> LENGTH: 14
<212> TYPE: PRT
<213> ORGANISM: Artificial sequence
<220> FEATURE:
<223> OTHER INFORMATION: synthetic sequence

<400> SEQUENCE: 105

Cys Ala Thr Gln Pro Gly Gln Gly Asn Thr Glu Ala Phe Phe
1               5                   10

<210> SEQ ID NO 106
<211> LENGTH: 14
<212> TYPE: PRT
<213> ORGANISM: Artificial sequence
<220> FEATURE:
<223> OTHER INFORMATION: synthetic sequence

<400> SEQUENCE: 106

Cys Ala Ser Ser Asp Arg Gly Pro Asn Gln Pro Gln His Phe
1               5                   10

<210> SEQ ID NO 107
<211> LENGTH: 14
<212> TYPE: PRT
<213> ORGANISM: Artificial sequence
<220> FEATURE:
<223> OTHER INFORMATION: synthetic sequence

<400> SEQUENCE: 107

Cys Ala Ser Ser Leu Gln Gly Ser Thr Asp Thr Gln Tyr Phe
1               5                   10

<210> SEQ ID NO 108
<211> LENGTH: 16
<212> TYPE: PRT
<213> ORGANISM: Artificial sequence
<220> FEATURE:
<223> OTHER INFORMATION: synthetic sequence

<400> SEQUENCE: 108

Cys Ala Thr Ser Asp Leu Pro Ser Gly Pro Tyr Asn Glu Gln Phe Phe
```

<210> SEQ ID NO 109
<211> LENGTH: 14
<212> TYPE: PRT
<213> ORGANISM: Artificial sequence
<220> FEATURE:
<223> OTHER INFORMATION: synthetic sequence

<400> SEQUENCE: 109

Cys Ser Ala Leu Pro Gly Leu Asp Thr Asp Thr Gln Tyr Phe
1               5                   10

<210> SEQ ID NO 110
<211> LENGTH: 18
<212> TYPE: PRT
<213> ORGANISM: Artificial sequence
<220> FEATURE:
<223> OTHER INFORMATION: synthetic sequence

<400> SEQUENCE: 110

Cys Ala Ser Ser Arg Thr Gly Phe Arg Ser Ser Tyr Asn Ser Pro Leu
1               5                   10                  15

His Phe

<210> SEQ ID NO 111
<211> LENGTH: 16
<212> TYPE: PRT
<213> ORGANISM: Artificial sequence
<220> FEATURE:
<223> OTHER INFORMATION: synthetic sequence

<400> SEQUENCE: 111

Cys Ala Trp Ser Asp Lys Ser Ser Ser Tyr Asn Ser Pro Leu His Phe
1               5                   10                  15

<210> SEQ ID NO 112
<211> LENGTH: 15
<212> TYPE: PRT
<213> ORGANISM: Artificial sequence
<220> FEATURE:
<223> OTHER INFORMATION: synthetic sequence

<400> SEQUENCE: 112

Cys Ala Ser Ser Leu Leu Ala Gly Asp Lys Asn Ile Gln Tyr Phe
1               5                   10                  15

<210> SEQ ID NO 113
<211> LENGTH: 14
<212> TYPE: PRT
<213> ORGANISM: Artificial sequence
<220> FEATURE:
<223> OTHER INFORMATION: synthetic sequence

<400> SEQUENCE: 113

Cys Ala Ser Ser Pro Thr Gly Ala Val Gln Pro Gln His Phe
1               5                   10

<210> SEQ ID NO 114
<211> LENGTH: 14
<212> TYPE: PRT
<213> ORGANISM: Artificial sequence
<220> FEATURE:
<223> OTHER INFORMATION: synthetic sequence

<400> SEQUENCE: 114

```
Cys Ala Ser Ser Tyr Thr Gly Gln Gly Val Gly Tyr Thr Phe
1               5                   10
```

<210> SEQ ID NO 115
<211> LENGTH: 14
<212> TYPE: PRT
<213> ORGANISM: Artificial sequence
<220> FEATURE:
<223> OTHER INFORMATION: synthetic sequence

<400> SEQUENCE: 115

```
Cys Ala Ser Ser Tyr Ser Glu Asp Asn Gln Pro Gln His Phe
1               5                   10
```

<210> SEQ ID NO 116
<211> LENGTH: 14
<212> TYPE: PRT
<213> ORGANISM: Artificial sequence
<220> FEATURE:
<223> OTHER INFORMATION: synthetic sequence

<400> SEQUENCE: 116

```
Cys Ala Ser Ser Gln Asp Ser Pro Asn Thr Glu Ala Phe Phe
1               5                   10
```

<210> SEQ ID NO 117
<211> LENGTH: 16
<212> TYPE: PRT
<213> ORGANISM: Artificial sequence
<220> FEATURE:
<223> OTHER INFORMATION: synthetic sequence

<400> SEQUENCE: 117

```
Cys Ser Ala Arg Asp Arg Gly Val Tyr Ser Asn Gln Pro Gln His Phe
1               5                   10                  15
```

<210> SEQ ID NO 118
<211> LENGTH: 13
<212> TYPE: PRT
<213> ORGANISM: Artificial sequence
<220> FEATURE:
<223> OTHER INFORMATION: synthetic sequence

<400> SEQUENCE: 118

```
Cys Ala Trp Ser Thr Arg Glu Asn Gln Pro Gln His Phe
1               5                   10
```

<210> SEQ ID NO 119
<211> LENGTH: 14
<212> TYPE: PRT
<213> ORGANISM: Artificial sequence
<220> FEATURE:
<223> OTHER INFORMATION: synthetic sequence

<400> SEQUENCE: 119

```
Cys Ala Ser Ser Leu Ala Pro Asn Thr Asp Thr Gln Tyr Phe
1               5                   10
```

<210> SEQ ID NO 120
<211> LENGTH: 14
<212> TYPE: PRT
<213> ORGANISM: Artificial sequence
<220> FEATURE:
<223> OTHER INFORMATION: synthetic sequence

<400> SEQUENCE: 120

```
Cys Ala Ser Ser Gly Glu Gly Ser Thr Asp Thr Gln Tyr Phe
```

```
1               5                   10
```

<210> SEQ ID NO 121
<211> LENGTH: 14
<212> TYPE: PRT
<213> ORGANISM: Artificial sequence
<220> FEATURE:
<223> OTHER INFORMATION: synthetic sequence

<400> SEQUENCE: 121

```
Cys Ala Ser Ser Tyr Ser Glu Asp Asn Ser Pro Leu His Phe
1               5                   10
```

<210> SEQ ID NO 122
<211> LENGTH: 11
<212> TYPE: PRT
<213> ORGANISM: Artificial sequence
<220> FEATURE:
<223> OTHER INFORMATION: synthetic sequence

<400> SEQUENCE: 122

```
Cys Ser Val Arg Ser Gly His Glu Gln Tyr Phe
1               5                   10
```

<210> SEQ ID NO 123
<211> LENGTH: 13
<212> TYPE: PRT
<213> ORGANISM: Artificial sequence
<220> FEATURE:
<223> OTHER INFORMATION: synthetic sequence

<400> SEQUENCE: 123

```
Cys Ala Ile Ser Asp Arg Gly Gln Asp Thr Gln Tyr Phe
1               5                   10
```

<210> SEQ ID NO 124
<211> LENGTH: 18
<212> TYPE: PRT
<213> ORGANISM: Artificial sequence
<220> FEATURE:
<223> OTHER INFORMATION: synthetic sequence

<400> SEQUENCE: 124

```
Cys Ala Ser Ser Arg Thr Gly Val Gly Ser Ser Tyr Asn Ser Pro Leu
1               5                   10                  15

His Phe
```

<210> SEQ ID NO 125
<211> LENGTH: 16
<212> TYPE: PRT
<213> ORGANISM: Artificial sequence
<220> FEATURE:
<223> OTHER INFORMATION: synthetic sequence

<400> SEQUENCE: 125

```
Cys Ala Ser Ser Leu Gly Gln Gly Ala Phe Thr Asp Thr Gln Tyr Phe
1               5                   10                  15
```

<210> SEQ ID NO 126
<211> LENGTH: 15
<212> TYPE: PRT
<213> ORGANISM: Artificial sequence
<220> FEATURE:
<223> OTHER INFORMATION: synthetic sequence

<400> SEQUENCE: 126

Cys Ala Ser Ser Leu Asn Arg Gly Arg Ser Gly Glu Leu Phe Phe
1               5                   10                  15

<210> SEQ ID NO 127
<211> LENGTH: 18
<212> TYPE: PRT
<213> ORGANISM: Artificial sequence
<220> FEATURE:
<223> OTHER INFORMATION: synthetic sequence

<400> SEQUENCE: 127

Cys Ala Ser Ser Arg Thr Gly Gly Gly Ser Ser Tyr Asn Ser Pro Leu
1               5                   10                  15

His Phe

<210> SEQ ID NO 128
<211> LENGTH: 14
<212> TYPE: PRT
<213> ORGANISM: Artificial sequence
<220> FEATURE:
<223> OTHER INFORMATION: synthetic sequence

<400> SEQUENCE: 128

Cys Ala Ser Ser Asp Arg Gly Pro Ala Asp Thr Gln Tyr Phe
1               5                   10

<210> SEQ ID NO 129
<211> LENGTH: 14
<212> TYPE: PRT
<213> ORGANISM: Artificial sequence
<220> FEATURE:
<223> OTHER INFORMATION: synthetic sequence

<400> SEQUENCE: 129

Cys Ala Ser Ser Leu Ser Ile Ser Gly Asn Thr Ile Tyr Phe
1               5                   10

<210> SEQ ID NO 130
<211> LENGTH: 14
<212> TYPE: PRT
<213> ORGANISM: Artificial sequence
<220> FEATURE:
<223> OTHER INFORMATION: synthetic sequence

<400> SEQUENCE: 130

Cys Ala Ser Ser Tyr Pro Glu Asp Asn Gln Pro Gln His Phe
1               5                   10

<210> SEQ ID NO 131
<211> LENGTH: 11
<212> TYPE: PRT
<213> ORGANISM: Artificial sequence
<220> FEATURE:
<223> OTHER INFORMATION: synthetic sequence

<400> SEQUENCE: 131

Cys Ala Ser Ser Gln Gly Val Gly Tyr Thr Phe
1               5                   10

<210> SEQ ID NO 132
<211> LENGTH: 15
<212> TYPE: PRT
<213> ORGANISM: Artificial sequence
<220> FEATURE:
<223> OTHER INFORMATION: synthetic sequence

<400> SEQUENCE: 132

Cys Ala Ser Arg Thr Ser Gly Pro Ser Tyr Asn Glu Gln Phe Phe
1               5                   10                  15

<210> SEQ ID NO 133
<211> LENGTH: 14
<212> TYPE: PRT
<213> ORGANISM: Artificial sequence
<220> FEATURE:
<223> OTHER INFORMATION: synthetic sequence

<400> SEQUENCE: 133

Cys Ala Ser Ser Tyr Ala Glu Asp Asn Ser Pro Leu His Phe
1               5                   10

<210> SEQ ID NO 134
<211> LENGTH: 15
<212> TYPE: PRT
<213> ORGANISM: Artificial sequence
<220> FEATURE:
<223> OTHER INFORMATION: synthetic sequence

<400> SEQUENCE: 134

Cys Ala Ser Arg Glu Ser Pro Thr Ser Thr Asp Thr Gln Tyr Phe
1               5                   10                  15

<210> SEQ ID NO 135
<211> LENGTH: 18
<212> TYPE: PRT
<213> ORGANISM: Artificial sequence
<220> FEATURE:
<223> OTHER INFORMATION: synthetic sequence

<400> SEQUENCE: 135

Cys Ala Ser Ser Arg Thr Gly Gln Gly Ser Ser Tyr Asn Ser Pro Leu
1               5                   10                  15

His Phe

<210> SEQ ID NO 136
<211> LENGTH: 16
<212> TYPE: PRT
<213> ORGANISM: Artificial sequence
<220> FEATURE:
<223> OTHER INFORMATION: synthetic sequence

<400> SEQUENCE: 136

Cys Ser Ala Leu Gly Gly Leu Ala Gly Val Ser Asp Thr Gln Tyr Phe
1               5                   10                  15

<210> SEQ ID NO 137
<211> LENGTH: 14
<212> TYPE: PRT
<213> ORGANISM: Artificial sequence
<220> FEATURE:
<223> OTHER INFORMATION: synthetic sequence

<400> SEQUENCE: 137

Cys Ala Ser Ser Tyr Pro Glu Leu Asn Thr Glu Ala Phe Phe
1               5                   10

<210> SEQ ID NO 138
<211> LENGTH: 18
<212> TYPE: PRT
<213> ORGANISM: Artificial sequence
<220> FEATURE:
<223> OTHER INFORMATION: synthetic sequence -continued

```
<400> SEQUENCE: 138

Cys Ala Ser Ser Arg Thr Gly Leu Lys Ser Ser Tyr Asn Ser Pro Leu
1               5                   10                  15

His Phe

<210> SEQ ID NO 139
<211> LENGTH: 15
<212> TYPE: PRT
<213> ORGANISM: Artificial sequence
<220> FEATURE:
<223> OTHER INFORMATION: synthetic sequence

<400> SEQUENCE: 139

Cys Ala Ser Ser Val Gly Gly Gly Glu Ile Tyr Gly Tyr Thr Phe
1               5                   10                  15

<210> SEQ ID NO 140
<211> LENGTH: 11
<212> TYPE: PRT
<213> ORGANISM: Artificial sequence
<220> FEATURE:
<223> OTHER INFORMATION: synthetic sequence

<400> SEQUENCE: 140

Cys Ala Ser Ser Glu Ser Leu Gly Tyr Thr Phe
1               5                   10

<210> SEQ ID NO 141
<211> LENGTH: 11
<212> TYPE: PRT
<213> ORGANISM: Artificial sequence
<220> FEATURE:
<223> OTHER INFORMATION: synthetic sequence

<400> SEQUENCE: 141

Cys Ala Ser Arg Gly Ala Asn Glu Gln Phe Phe
1               5                   10

<210> SEQ ID NO 142
<211> LENGTH: 16
<212> TYPE: PRT
<213> ORGANISM: Artificial sequence
<220> FEATURE:
<223> OTHER INFORMATION: synthetic sequence

<400> SEQUENCE: 142

Cys Ala Ser Ser Ile Arg Ser Gly Thr Ser Thr Asp Thr Gln Tyr Phe
1               5                   10                  15

<210> SEQ ID NO 143
<211> LENGTH: 13
<212> TYPE: PRT
<213> ORGANISM: Artificial sequence
<220> FEATURE:
<223> OTHER INFORMATION: synthetic sequence

<400> SEQUENCE: 143

Cys Ala Ser Ser Leu Lys Ser Asp Ser Pro Leu His Phe
1               5                   10

<210> SEQ ID NO 144
<211> LENGTH: 11
<212> TYPE: PRT
<213> ORGANISM: Artificial sequence
<220> FEATURE:
<223> OTHER INFORMATION: synthetic sequence
```

<400> SEQUENCE: 144

Cys Ser Ala Arg Ala Gly His Glu Gln Tyr Phe
1               5                   10

<210> SEQ ID NO 145
<211> LENGTH: 14
<212> TYPE: PRT
<213> ORGANISM: Artificial sequence
<220> FEATURE:
<223> OTHER INFORMATION: synthetic sequence

<400> SEQUENCE: 145

Cys Ala Ser Ser Tyr Ala Glu Pro Asn Thr Glu Ala Phe Phe
1               5                   10

<210> SEQ ID NO 146
<211> LENGTH: 13
<212> TYPE: PRT
<213> ORGANISM: Artificial sequence
<220> FEATURE:
<223> OTHER INFORMATION: synthetic sequence

<400> SEQUENCE: 146

Cys Ser Ala Arg Ala Gly Val Gln Glu Thr Gln Tyr Phe
1               5                   10

<210> SEQ ID NO 147
<211> LENGTH: 16
<212> TYPE: PRT
<213> ORGANISM: Artificial sequence
<220> FEATURE:
<223> OTHER INFORMATION: synthetic sequence

<400> SEQUENCE: 147

Cys Ala Ser Ser Leu Val Thr Gly His Ser Thr Asp Thr Gln Tyr Phe
1               5                   10                  15

<210> SEQ ID NO 148
<211> LENGTH: 18
<212> TYPE: PRT
<213> ORGANISM: Artificial sequence
<220> FEATURE:
<223> OTHER INFORMATION: synthetic sequence

<400> SEQUENCE: 148

Cys Ala Ser Ser Arg Thr Gly Arg Gly Ser Ser Tyr Asn Ser Pro Leu
1               5                   10                  15

His Phe

<210> SEQ ID NO 149
<211> LENGTH: 16
<212> TYPE: PRT
<213> ORGANISM: Artificial sequence
<220> FEATURE:
<223> OTHER INFORMATION: synthetic sequence

<400> SEQUENCE: 149

Cys Ser Ala Arg Asp Gly Gly Val Tyr Ser Asn Gln Pro Gln His Phe
1               5                   10                  15

<210> SEQ ID NO 150
<211> LENGTH: 15
<212> TYPE: PRT
<213> ORGANISM: Artificial sequence
<220> FEATURE:

```
<223> OTHER INFORMATION: synthetic sequence

<400> SEQUENCE: 150

Cys Ala Ser Ser Pro Arg Gly Gly Gly Asn Thr Glu Ala Phe Phe
1               5                   10                  15

<210> SEQ ID NO 151
<211> LENGTH: 14
<212> TYPE: PRT
<213> ORGANISM: Artificial sequence
<220> FEATURE:
<223> OTHER INFORMATION: synthetic sequence

<400> SEQUENCE: 151

Cys Ala Ser Ser Tyr Met Glu Ser Asn Gln Pro Gln His Phe
1               5                   10

<210> SEQ ID NO 152
<211> LENGTH: 14
<212> TYPE: PRT
<213> ORGANISM: Artificial sequence
<220> FEATURE:
<223> OTHER INFORMATION: synthetic sequence

<400> SEQUENCE: 152

Cys Ala Ser Ser Gly Gln Gly Ser Thr Asp Thr Gln Tyr Phe
1               5                   10

<210> SEQ ID NO 153
<211> LENGTH: 14
<212> TYPE: PRT
<213> ORGANISM: Artificial sequence
<220> FEATURE:
<223> OTHER INFORMATION: synthetic sequence

<400> SEQUENCE: 153

Cys Ala Ser Ser Tyr Pro Glu Ser Asn Thr Glu Ala Phe Phe
1               5                   10

<210> SEQ ID NO 154
<211> LENGTH: 15
<212> TYPE: PRT
<213> ORGANISM: Artificial sequence
<220> FEATURE:
<223> OTHER INFORMATION: synthetic sequence

<400> SEQUENCE: 154

Cys Ala Ser Ser Gln Ala Gly Gly Leu Thr Asp Thr Gln Tyr Phe
1               5                   10                  15

<210> SEQ ID NO 155
<211> LENGTH: 12
<212> TYPE: PRT
<213> ORGANISM: Artificial sequence
<220> FEATURE:
<223> OTHER INFORMATION: synthetic sequence

<400> SEQUENCE: 155

Cys Ala Ser Arg Gln Gly Ala Lys Thr Gln Tyr Phe
1               5                   10

<210> SEQ ID NO 156
<211> LENGTH: 15
<212> TYPE: PRT
<213> ORGANISM: Artificial sequence
<220> FEATURE:
<223> OTHER INFORMATION: synthetic sequence
```

<400> SEQUENCE: 156

Cys Ser Ala Arg Ile Gly Thr Ala Thr Asn Glu Lys Leu Phe Phe
1               5                   10                  15

<210> SEQ ID NO 157
<211> LENGTH: 14
<212> TYPE: PRT
<213> ORGANISM: Artificial sequence
<220> FEATURE:
<223> OTHER INFORMATION: synthetic sequence

<400> SEQUENCE: 157

Cys Ala Ser Ser Phe Ser Gly Gly Leu Ser Pro Leu His Phe
1               5                   10

<210> SEQ ID NO 158
<211> LENGTH: 15
<212> TYPE: PRT
<213> ORGANISM: Artificial sequence
<220> FEATURE:
<223> OTHER INFORMATION: synthetic sequence

<400> SEQUENCE: 158

Cys Ser Ala Arg Val Gly Thr Ala Ser Thr Asp Thr Gln Tyr Phe
1               5                   10                  15

<210> SEQ ID NO 159
<211> LENGTH: 18
<212> TYPE: PRT
<213> ORGANISM: Artificial sequence
<220> FEATURE:
<223> OTHER INFORMATION: synthetic sequence

<400> SEQUENCE: 159

Cys Ala Ser Ser Arg Thr Gly Phe Gly Ser Ser Tyr Asn Ser Pro Leu
1               5                   10                  15

His Phe

<210> SEQ ID NO 160
<211> LENGTH: 14
<212> TYPE: PRT
<213> ORGANISM: Artificial sequence
<220> FEATURE:
<223> OTHER INFORMATION: synthetic sequence

<400> SEQUENCE: 160

Cys Ala Ser Ser Ile Asp Pro Asp Arg Glu Lys Leu Phe Phe
1               5                   10

<210> SEQ ID NO 161
<211> LENGTH: 14
<212> TYPE: PRT
<213> ORGANISM: Artificial sequence
<220> FEATURE:
<223> OTHER INFORMATION: synthetic sequence

<400> SEQUENCE: 161

Cys Ala Ser Ser Gln Glu Gln Gly Arg Ala Glu Ala Phe Phe
1               5                   10

<210> SEQ ID NO 162
<211> LENGTH: 11
<212> TYPE: PRT
<213> ORGANISM: Artificial sequence
<220> FEATURE:

-continued

<223> OTHER INFORMATION: synthetic sequence

<400> SEQUENCE: 162

Cys Ser Ala Asn Ser Gly His Glu Gln Tyr Phe
1               5                   10

<210> SEQ ID NO 163
<211> LENGTH: 15
<212> TYPE: PRT
<213> ORGANISM: Artificial sequence
<220> FEATURE:
<223> OTHER INFORMATION: synthetic sequence

<400> SEQUENCE: 163

Cys Ser Ala Arg Glu Gly Ser Ala Ser Thr Asp Thr Gln Tyr Phe
1               5                   10                  15

<210> SEQ ID NO 164
<211> LENGTH: 13
<212> TYPE: PRT
<213> ORGANISM: Artificial sequence
<220> FEATURE:
<223> OTHER INFORMATION: synthetic sequence

<400> SEQUENCE: 164

Cys Ser Val Gly Leu Gly Val Asn Gln Pro Gln His Phe
1               5                   10

<210> SEQ ID NO 165
<211> LENGTH: 14
<212> TYPE: PRT
<213> ORGANISM: Artificial sequence
<220> FEATURE:
<223> OTHER INFORMATION: synthetic sequence

<400> SEQUENCE: 165

Cys Ser Ala Lys Thr Ser Gly Arg Gly Glu Thr Gln Tyr Phe
1               5                   10

<210> SEQ ID NO 166
<211> LENGTH: 15
<212> TYPE: PRT
<213> ORGANISM: Artificial sequence
<220> FEATURE:
<223> OTHER INFORMATION: synthetic sequence

<400> SEQUENCE: 166

Cys Ala Ser Ser Leu Ala Leu Gly Glu Gly Ser Pro Leu His Phe
1               5                   10                  15

<210> SEQ ID NO 167
<211> LENGTH: 14
<212> TYPE: PRT
<213> ORGANISM: Artificial sequence
<220> FEATURE:
<223> OTHER INFORMATION: synthetic sequence

<400> SEQUENCE: 167

Cys Ala Ser Arg Thr Gln Gln Gly Asn Gln Pro Gln His Phe
1               5                   10

<210> SEQ ID NO 168
<211> LENGTH: 13
<212> TYPE: PRT
<213> ORGANISM: Artificial sequence
<220> FEATURE:
<223> OTHER INFORMATION: synthetic sequence

```
<400> SEQUENCE: 168

Cys Ala Ser Ser Ala Gly Arg Gly Asp Gly Tyr Thr Phe
1               5                   10

<210> SEQ ID NO 169
<211> LENGTH: 16
<212> TYPE: PRT
<213> ORGANISM: Artificial sequence
<220> FEATURE:
<223> OTHER INFORMATION: synthetic sequence

<400> SEQUENCE: 169

Cys Ser Ala Arg Glu Gly Gln Phe Ser Gly Ala Asn Val Leu Thr Phe
1               5                   10                  15

<210> SEQ ID NO 170
<211> LENGTH: 16
<212> TYPE: PRT
<213> ORGANISM: Artificial sequence
<220> FEATURE:
<223> OTHER INFORMATION: synthetic sequence

<400> SEQUENCE: 170

Cys Ala Ser Ser Leu Gly Thr Gly Gly Ser Tyr Asn Glu Gln Phe Phe
1               5                   10                  15

<210> SEQ ID NO 171
<211> LENGTH: 15
<212> TYPE: PRT
<213> ORGANISM: Artificial sequence
<220> FEATURE:
<223> OTHER INFORMATION: synthetic sequence

<400> SEQUENCE: 171

Cys Ser Ala Thr Arg Asp Arg Arg Thr Tyr Asn Glu Gln Phe Phe
1               5                   10                  15

<210> SEQ ID NO 172
<211> LENGTH: 16
<212> TYPE: PRT
<213> ORGANISM: Artificial sequence
<220> FEATURE:
<223> OTHER INFORMATION: synthetic sequence

<400> SEQUENCE: 172

Cys Ala Ser Ser Pro Arg Asp Arg Val Asn Thr Gly Glu Leu Phe Phe
1               5                   10                  15

<210> SEQ ID NO 173
<211> LENGTH: 15
<212> TYPE: PRT
<213> ORGANISM: Artificial sequence
<220> FEATURE:
<223> OTHER INFORMATION: synthetic sequence

<400> SEQUENCE: 173

Cys Ser Ala Arg Thr Gly Thr Ala Ser Thr Asp Thr Gln Tyr Phe
1               5                   10                  15

<210> SEQ ID NO 174
<211> LENGTH: 15
<212> TYPE: PRT
<213> ORGANISM: Artificial sequence
<220> FEATURE:
<223> OTHER INFORMATION: synthetic sequence
```

```
<400> SEQUENCE: 174

Cys Ala Ser Ser Pro Asp Arg Gly Lys Thr Asp Thr Gln Tyr Phe
1               5                   10                  15

<210> SEQ ID NO 175
<211> LENGTH: 14
<212> TYPE: PRT
<213> ORGANISM: Artificial sequence
<220> FEATURE:
<223> OTHER INFORMATION: synthetic sequence

<400> SEQUENCE: 175

Cys Ala Ser Ser Tyr Met Glu Asp Asn Gln Pro Gln His Phe
1               5                   10

<210> SEQ ID NO 176
<211> LENGTH: 16
<212> TYPE: PRT
<213> ORGANISM: Artificial sequence
<220> FEATURE:
<223> OTHER INFORMATION: synthetic sequence

<400> SEQUENCE: 176

Cys Ala Ser Ser Leu Val Thr Gly Trp Asp Thr Asp Thr Gln Tyr Phe
1               5                   10                  15

<210> SEQ ID NO 177
<211> LENGTH: 15
<212> TYPE: PRT
<213> ORGANISM: Artificial sequence
<220> FEATURE:
<223> OTHER INFORMATION: synthetic sequence

<400> SEQUENCE: 177

Cys Ser Ala Thr Arg Asp Arg Arg Asn Thr Gly Glu Leu Phe Phe
1               5                   10                  15

<210> SEQ ID NO 178
<211> LENGTH: 15
<212> TYPE: PRT
<213> ORGANISM: Artificial sequence
<220> FEATURE:
<223> OTHER INFORMATION: synthetic sequence

<400> SEQUENCE: 178

Cys Ser Ala Thr Leu Asp Arg Arg Ser Tyr Asn Glu Gln Phe Phe
1               5                   10                  15

<210> SEQ ID NO 179
<211> LENGTH: 12
<212> TYPE: PRT
<213> ORGANISM: Artificial sequence
<220> FEATURE:
<223> OTHER INFORMATION: synthetic sequence

<400> SEQUENCE: 179

Cys Ala Ser Met Asn Arg Glu Asp Gly Tyr Thr Phe
1               5                   10

<210> SEQ ID NO 180
<211> LENGTH: 14
<212> TYPE: PRT
<213> ORGANISM: Artificial sequence
<220> FEATURE:
<223> OTHER INFORMATION: synthetic sequence

<400> SEQUENCE: 180
```

```
Cys Ala Ser Ser Leu Ser Ser Pro Gln Glu Thr Gln Tyr Phe
1               5                   10

<210> SEQ ID NO 181
<211> LENGTH: 14
<212> TYPE: PRT
<213> ORGANISM: Artificial sequence
<220> FEATURE:
<223> OTHER INFORMATION: synthetic sequence

<400> SEQUENCE: 181

Cys Ala Ser Ser Tyr Ala Glu Ser Asn Gln Pro Gln His Phe
1               5                   10

<210> SEQ ID NO 182
<211> LENGTH: 14
<212> TYPE: PRT
<213> ORGANISM: Artificial sequence
<220> FEATURE:
<223> OTHER INFORMATION: synthetic sequence

<400> SEQUENCE: 182

Cys Ser Ala Arg Lys Asp Ser Arg Thr Asp Thr Gln Tyr Phe
1               5                   10

<210> SEQ ID NO 183
<211> LENGTH: 14
<212> TYPE: PRT
<213> ORGANISM: Artificial sequence
<220> FEATURE:
<223> OTHER INFORMATION: synthetic sequence

<400> SEQUENCE: 183

Cys Ala Ile Ser Leu Ser Gly Gly Asp Tyr Glu Gln Tyr Phe
1               5                   10

<210> SEQ ID NO 184
<211> LENGTH: 14
<212> TYPE: PRT
<213> ORGANISM: Artificial sequence
<220> FEATURE:
<223> OTHER INFORMATION: synthetic sequence

<400> SEQUENCE: 184

Cys Ser Ala Lys Trp Gly Gly Arg Gly Glu Thr Gln Tyr Phe
1               5                   10

<210> SEQ ID NO 185
<211> LENGTH: 15
<212> TYPE: PRT
<213> ORGANISM: Artificial sequence
<220> FEATURE:
<223> OTHER INFORMATION: synthetic sequence

<400> SEQUENCE: 185

Cys Ala Ser Ser Ser Gly Asp Ser Tyr Asn Ser Pro Leu His Phe
1               5                   10                  15

<210> SEQ ID NO 186
<211> LENGTH: 14
<212> TYPE: PRT
<213> ORGANISM: Artificial sequence
<220> FEATURE:
<223> OTHER INFORMATION: synthetic sequence

<400> SEQUENCE: 186
```

Cys Ala Ser Ser Tyr Ser Glu Gly Asn Ser Pro Leu His Phe
1               5                   10

<210> SEQ ID NO 187
<211> LENGTH: 15
<212> TYPE: PRT
<213> ORGANISM: Artificial sequence
<220> FEATURE:
<223> OTHER INFORMATION: synthetic sequence

<400> SEQUENCE: 187

Cys Ser Ala Leu Glu Gly Gly Thr Gly Asn Gln Pro Gln His Phe
1               5                   10                  15

<210> SEQ ID NO 188
<211> LENGTH: 19
<212> TYPE: PRT
<213> ORGANISM: Artificial sequence
<220> FEATURE:
<223> OTHER INFORMATION: synthetic sequence

<400> SEQUENCE: 188

Cys Ala Ser Ser Ile Arg Gly Gln Gly Ala Ile Ser Ser Tyr Asn Glu
1               5                   10                  15

Gln Phe Phe

<210> SEQ ID NO 189
<211> LENGTH: 14
<212> TYPE: PRT
<213> ORGANISM: Artificial sequence
<220> FEATURE:
<223> OTHER INFORMATION: synthetic sequence

<400> SEQUENCE: 189

Cys Ala Ser Arg Glu Gly Gly Ser Asn Gln Pro Gln His Phe
1               5                   10

<210> SEQ ID NO 190
<211> LENGTH: 14
<212> TYPE: PRT
<213> ORGANISM: Artificial sequence
<220> FEATURE:
<223> OTHER INFORMATION: synthetic sequence

<400> SEQUENCE: 190

Cys Ala Ser Ser Leu Gly Ser Pro Gln Glu Thr Gln Tyr Phe
1               5                   10

<210> SEQ ID NO 191
<211> LENGTH: 16
<212> TYPE: PRT
<213> ORGANISM: Artificial sequence
<220> FEATURE:
<223> OTHER INFORMATION: synthetic sequence

<400> SEQUENCE: 191

Cys Ala Trp Ser Gly Leu Ala Gly Gly Ala Gln Glu Thr Gln Tyr Phe
1               5                   10                  15

<210> SEQ ID NO 192
<211> LENGTH: 14
<212> TYPE: PRT
<213> ORGANISM: Artificial sequence
<220> FEATURE:
<223> OTHER INFORMATION: synthetic sequence

<400> SEQUENCE: 192

```
Cys Ala Ser Ser Tyr Thr Gly Gln Gly Gln Gly Tyr Thr Phe
1               5                   10
```

<210> SEQ ID NO 193
<211> LENGTH: 14
<212> TYPE: PRT
<213> ORGANISM: Artificial sequence
<220> FEATURE:
<223> OTHER INFORMATION: synthetic sequence

<400> SEQUENCE: 193

```
Cys Ala Ser Ser Trp Thr Glu Gly Ser Tyr Glu Gln Tyr Phe
1               5                   10
```

<210> SEQ ID NO 194
<211> LENGTH: 15
<212> TYPE: PRT
<213> ORGANISM: Artificial sequence
<220> FEATURE:
<223> OTHER INFORMATION: synthetic sequence

<400> SEQUENCE: 194

```
Cys Ala Ser Ser Leu Glu Gln Gly Arg Asn Thr Glu Ala Phe Phe
1               5                   10                  15
```

<210> SEQ ID NO 195
<211> LENGTH: 13
<212> TYPE: PRT
<213> ORGANISM: Artificial sequence
<220> FEATURE:
<223> OTHER INFORMATION: synthetic sequence

<400> SEQUENCE: 195

```
Cys Ser Ala Arg Asp Trp Arg Gln Glu Thr Gln Tyr Phe
1               5                   10
```

<210> SEQ ID NO 196
<211> LENGTH: 16
<212> TYPE: PRT
<213> ORGANISM: Artificial sequence
<220> FEATURE:
<223> OTHER INFORMATION: synthetic sequence

<400> SEQUENCE: 196

```
Cys Ala Ser Ser Pro Arg Ser Ala Gly Pro Gln Glu Thr Gln Tyr Phe
1               5                   10                  15
```

<210> SEQ ID NO 197
<211> LENGTH: 13
<212> TYPE: PRT
<213> ORGANISM: Artificial sequence
<220> FEATURE:
<223> OTHER INFORMATION: synthetic sequence

<400> SEQUENCE: 197

```
Cys Ala Ile Ser Ser Arg Gly Gln Asp Glu Gln Tyr Phe
1               5                   10
```

<210> SEQ ID NO 198
<211> LENGTH: 17
<212> TYPE: PRT
<213> ORGANISM: Artificial sequence
<220> FEATURE:
<223> OTHER INFORMATION: synthetic sequence

<400> SEQUENCE: 198

Cys Ala Ser Ser Leu Lys Ala Ser Gly Arg Gly Thr Asp Thr Gln Tyr
1               5                   10                  15

Phe

<210> SEQ ID NO 199
<211> LENGTH: 15
<212> TYPE: PRT
<213> ORGANISM: Artificial sequence
<220> FEATURE:
<223> OTHER INFORMATION: synthetic sequence

<400> SEQUENCE: 199

Cys Ser Ala Arg Thr Gly Thr Gly Asn Ala Gly Glu Leu Phe Phe
1               5                   10                  15

<210> SEQ ID NO 200
<211> LENGTH: 11
<212> TYPE: PRT
<213> ORGANISM: SARS-CoV-2

<400> SEQUENCE: 200

His Thr Thr Asp Pro Ser Phe Leu Gly Arg Tyr
1               5                   10

<210> SEQ ID NO 201
<211> LENGTH: 9
<212> TYPE: PRT
<213> ORGANISM: SARS-CoV-2

<400> SEQUENCE: 201

Tyr Leu Gln Pro Arg Thr Phe Leu Leu
1               5

<210> SEQ ID NO 202
<211> LENGTH: 8
<212> TYPE: PRT
<213> ORGANISM: SARS-CoV-2

<400> SEQUENCE: 202

Ala Pro His Gly Val Val Phe Leu
1               5

<210> SEQ ID NO 203
<211> LENGTH: 9
<212> TYPE: PRT
<213> ORGANISM: SARS-CoV-2

<400> SEQUENCE: 203

Tyr Ala Asn Arg Asn Arg Phe Leu Tyr
1               5

<210> SEQ ID NO 204
<211> LENGTH: 9
<212> TYPE: PRT
<213> ORGANISM: SARS-CoV-2

<400> SEQUENCE: 204

Ser Pro Arg Trp Tyr Phe Tyr Tyr Leu
1               5

<210> SEQ ID NO 205
<211> LENGTH: 10
<212> TYPE: PRT
<213> ORGANISM: SARS-CoV-2

```
<400> SEQUENCE: 205

Gln Glu Leu Ile Arg Gln Gly Thr Asp Tyr
1               5                   10

<210> SEQ ID NO 206
<211> LENGTH: 10
<212> TYPE: PRT
<213> ORGANISM: SARS-CoV-2

<400> SEQUENCE: 206

Tyr Phe Thr Ser Asp Tyr Tyr Gln Leu Tyr
1               5                   10
```